United States Patent
Pelletier et al.

(10) Patent No.: US 11,071,744 B2
(45) Date of Patent: Jul. 27, 2021

(54) PRODRUG SALTS

(71) Applicant: AEROMICS, INC., New Haven, CT (US)

(72) Inventors: Marc F. Pelletier, Shaker Heights, OH (US); Paul Robert McGuirk, Spring Hill, FL (US); George William Farr, Rocky River, OH (US); Robert Zamboni, Beaconsfield (CA); John Colucci, Kirkland (CA); Helmi Zaghdane, Pincourt (CA)

(73) Assignee: AEROMICS, INC., New Haven, CT (US)

(*) Notice: Subject to any disclaimer, the term of this patent is extended or adjusted under 35 U.S.C. 154(b) by 0 days.

(21) Appl. No.: 16/665,333

(22) Filed: Oct. 28, 2019

(65) Prior Publication Data

US 2020/0297740 A1 Sep. 24, 2020

Related U.S. Application Data

(60) Continuation of application No. 16/296,663, filed on Mar. 8, 2019, now abandoned, which is a continuation of application No. 15/792,707, filed on Oct. 24, 2017, now Pat. No. 10,258,636, which is a division of application No. 15/034,274, filed as application No. PCT/US2014/064447 on Nov. 6, 2014, now Pat. No. 9,827,253.

(60) Provisional application No. 61/900,878, filed on Nov. 6, 2013, provisional application No. 61/900,919, filed on Nov. 6, 2013, provisional application No. 61/900,946, filed on Nov. 6, 2013.

(51) Int. Cl.
| | |
|---|---|
| A61K 31/661 | (2006.01) |
| A61K 31/167 | (2006.01) |
| A61K 47/18 | (2017.01) |
| A61K 31/222 | (2006.01) |
| A61K 31/5375 | (2006.01) |
| C07F 9/09 | (2006.01) |
| A61K 9/00 | (2006.01) |

(52) U.S. Cl.
CPC .......... *A61K 31/661* (2013.01); *A61K 9/0019* (2013.01); *A61K 31/167* (2013.01); *A61K 31/222* (2013.01); *A61K 31/5375* (2013.01); *A61K 47/18* (2013.01); *C07F 9/09* (2013.01)

(58) Field of Classification Search
CPC .. A61K 31/661; A61K 9/0019; A61K 31/167; A61K 31/222; A61K 31/5375; A61K 47/18; C07F 9/09

See application file for complete search history.

(56) References Cited

U.S. PATENT DOCUMENTS

| | | |
|---|---|---|
| 3,331,874 A | 7/1967 | Stecker |
| 3,332,996 A | 7/1967 | Zerweck et al. |
| 5,137,871 A | 8/1992 | Wei |
| 5,324,749 A | 6/1994 | Woog et al. |
| 5,486,530 A | 1/1996 | Boelke et al. |
| 5,519,035 A | 5/1996 | Maiese et al. |
| 5,741,671 A | 4/1998 | Agre |
| 5,858,702 A | 1/1999 | Agre |
| 5,905,090 A | 5/1999 | Bertolini et al. |
| 6,255,298 B1 | 7/2001 | Lysko et al. |
| 6,500,809 B1 | 12/2002 | Frazer |
| 7,601,745 B2 | 10/2009 | Leban et al. |
| 7,626,042 B2 | 12/2009 | Muto et al. |
| 7,659,312 B2 | 2/2010 | Nakada et al. |
| 7,671,058 B2 | 3/2010 | Tokuyama et al. |
| 7,700,655 B2 | 4/2010 | Muto et al. |
| 7,872,048 B2 | 1/2011 | Simard |
| 7,906,555 B2 | 3/2011 | Flynn et al. |
| 8,003,610 B2 | 8/2011 | Shaw et al. |
| 8,097,759 B2 | 1/2012 | Muto et al. |
| 8,263,657 B2 | 9/2012 | Muto et al. |
| 8,277,845 B2 | 10/2012 | Jacobson et al. |
| 8,946,293 B2 | 2/2015 | Jacobson et al. |
| 8,980,952 B2 | 3/2015 | Simard et al. |
| 9,573,885 B2 | 2/2017 | Pelletier et al. |
| 9,827,253 B2 | 11/2017 | Pelletier et al. |

(Continued)

FOREIGN PATENT DOCUMENTS

| | | |
|---|---|---|
| CA | 2 108 794 C | 6/2003 |
| EP | 0 338 415 A2 | 10/1989 |

(Continued)

OTHER PUBLICATIONS

U.S. Appl. No. 12/381,086, filed Mar. 6, 2009, Wood et al.

(Continued)

*Primary Examiner* — Anna Pagonakis
(74) *Attorney, Agent, or Firm* — Hoxie & Associates LLC

(57) ABSTRACT

Provided are novel prodrug salts of selective aquaporin inhibitors, their use as pharmaceuticals, and pharmaceutical compositions comprising them, and novel processes for their synthesis and novel intermediates for use in their synthesis. Also provided is use of a compound for the prophylaxis, treatment, and control of aquaporin-mediated conditions. Aquaporin inhibitors, e.g., inhibitors of AQP4 and/or AQP2, may be of utility in the treatment or control of diseases of water imbalance, for example edema (particularly edema of the brain and spinal cord), hyponatremia, and excess fluid retention, as well as diseases such as epilepsy, retinal ischemia and other diseases of the eye, myocardial ischemia, myocardial ischemia/reperfusion injury, myocardial infarction, myocardial hypoxia, congestive heart failure, sepsis, and neuromyelitis optica, as well as migraines.

20 Claims, 13 Drawing Sheets

(56) References Cited

U.S. PATENT DOCUMENTS

| | | | |
|---|---|---|---|
| 9,949,991 B2 | 4/2018 | Pelletier et al. |
| 9,994,514 B2 | 6/2018 | Pelletier et al. |
| 10,004,703 B2 | 6/2018 | Jacobson et al. |
| 10,258,636 B2 | 4/2019 | Pelletier et al. |
| 2001/0046993 A1 | 11/2001 | Ikeda et al. |
| 2002/0061311 A1 | 5/2002 | Haas et al. |
| 2003/0215889 A1 | 11/2003 | Simard et al. |
| 2004/0259877 A1 | 12/2004 | Muto et al. |
| 2005/0085734 A1 | 4/2005 | Tehrani |
| 2005/0182012 A1 | 8/2005 | McEvoy et al. |
| 2006/0014811 A1 | 1/2006 | Muto et al. |
| 2006/0019958 A1 | 1/2006 | Muto et al. |
| 2006/0035944 A1 | 2/2006 | Muto et al. |
| 2006/0094718 A1 | 5/2006 | Muto et al. |
| 2006/0100257 A1 | 5/2006 | Muto et al. |
| 2006/0111409 A1 | 5/2006 | Muto et al. |
| 2006/0167110 A1 | 7/2006 | Blume et al. |
| 2007/0254956 A1 | 11/2007 | Shudo et al. |
| 2007/0281978 A1 | 12/2007 | Nakada et al. |
| 2008/0125488 A1 | 5/2008 | Leverve et al. |
| 2008/0171719 A1 | 7/2008 | Chatterton et al. |
| 2008/0176822 A1 | 7/2008 | Chen |
| 2008/0214486 A1 | 9/2008 | Chatterton et al. |
| 2008/0221169 A1 | 9/2008 | Flynn et al. |
| 2008/0234233 A1 | 9/2008 | Muto et al. |
| 2009/0163545 A1 | 6/2009 | Goldfarb |
| 2009/0239868 A1 | 9/2009 | Muto et al. |
| 2009/0239919 A1 | 9/2009 | Wood et al. |
| 2010/0016381 A1 | 1/2010 | Asakawa et al. |
| 2010/0113770 A1 | 5/2010 | Muto et al. |
| 2010/0125090 A1 | 5/2010 | Hadida Ruah et al. |
| 2010/0184856 A1 | 7/2010 | Lau et al. |
| 2010/0190796 A1 | 7/2010 | Verkman et al. |
| 2010/0274051 A1 | 10/2010 | Muto et al. |
| 2011/0052678 A1 | 3/2011 | Shantha et al. |
| 2011/0172195 A1 | 7/2011 | Flynn et al. |
| 2012/0183600 A1 | 7/2012 | Chen |
| 2012/0196875 A1 | 8/2012 | Bouyssou et al. |
| 2012/0238623 A1 | 9/2012 | Chandraratna et al. |
| 2012/0245094 A1 | 9/2012 | Jacobsen et al. |
| 2012/0282591 A1 | 11/2012 | Thatte et al. |
| 2015/0133405 A1 | 5/2015 | Pelletier et al. |
| 2015/0166589 A1 | 6/2015 | Anderson et al. |
| 2015/0342967 A1 | 12/2015 | Pelletier et al. |
| 2016/0220680 A1 | 8/2016 | Itai et al. |
| 2016/0264604 A1 | 9/2016 | Pelletier et al. |
| 2016/0279155 A1 | 9/2016 | Pelletier et al. |
| 2016/0346302 A1 | 12/2016 | Pelletier et al. |
| 2017/0216321 A1 | 8/2017 | Jacobson et al. |
| 2018/0042873 A1 | 2/2018 | Pelletier et al. |
| 2018/0155727 A1 | 6/2018 | Simard et al. |
| 2018/0334424 A1 | 11/2018 | Pelletier et al. |
| 2019/0185496 A1 | 6/2019 | McGuirk et al. |
| 2019/0307779 A1 | 10/2019 | Pelletier et al. |

FOREIGN PATENT DOCUMENTS

| | | |
|---|---|---|
| EP | 1 352 650 A1 | 10/2003 |
| EP | 1 510 210 A1 | 3/2005 |
| EP | 1 512 397 A1 | 3/2005 |
| EP | 1 514 544 A1 | 3/2005 |
| EP | 1 535 609 A1 | 6/2005 |
| EP | 1 555 018 A1 | 7/2005 |
| EP | 1 649 852 A1 | 4/2006 |
| EP | 2 201 946 A1 | 6/2010 |
| RU | 2 461 375 C1 | 9/2012 |
| WO | WO 99/07382 A1 | 2/1999 |
| WO | WO 01/23399 A1 | 4/2001 |
| WO | WO 02/49632 A1 | 6/2002 |
| WO | WO 2006/036278 A2 | 4/2006 |
| WO | WO 2006/074127 A2 | 7/2006 |
| WO | WO 2007/084464 A2 | 7/2007 |
| WO | WO 2007/143689 A2 | 12/2007 |
| WO | WO 2008/046014 A1 | 4/2008 |
| WO | WO 2008/052190 A2 | 5/2008 |
| WO | WO 2008/060705 A2 | 5/2008 |
| WO | WO 2008/089103 A2 | 7/2008 |
| WO | WO 2008/089212 A1 | 7/2008 |
| WO | WO 2008/098160 A1 | 8/2008 |
| WO | WO 2008/100636 A2 | 8/2008 |
| WO | WO 2008/133884 A2 | 11/2008 |
| WO | WO 2009/002832 A2 | 12/2008 |
| WO | WO 2009/006555 A2 | 1/2009 |
| WO | WO 2009/054439 A1 | 4/2009 |
| WO | WO 2009/073711 A1 | 6/2009 |
| WO | WO 2009/074809 A1 | 6/2009 |
| WO | WO 2009/097443 A2 | 8/2009 |
| WO | WO 2009/139925 A1 | 11/2009 |
| WO | WO 2010/033560 A2 | 3/2010 |
| WO | WO 2010/048273 A2 | 4/2010 |
| WO | WO 2010/101648 A1 | 9/2010 |
| WO | WO 2011/112791 A1 | 9/2011 |
| WO | WO 2012/012347 A2 | 1/2012 |
| WO | WO 2012/150857 A1 | 11/2012 |
| WO | WO 2013/152313 A1 | 10/2013 |
| WO | WO 2013/165606 A1 | 11/2013 |
| WO | WO 2013/169939 A2 | 11/2013 |
| WO | WO 2015/037659 A1 | 3/2015 |
| WO | WO 2015/069948 A1 | 5/2015 |
| WO | WO 2015/069956 A2 | 5/2015 |
| WO | WO 2016/077787 A1 | 5/2016 |
| WO | WO 2016/196113 A1 | 12/2016 |
| WO | WO 2017/062765 A1 | 4/2017 |
| WO | WO 2017/197371 A1 | 11/2017 |
| WO | WO 2018/023035 A1 | 2/2018 |

OTHER PUBLICATIONS

U.S. Appl. No. 14/398,947, filed Nov. 4, 2014, Pelletier et al.
U.S. Appl. No. 14/752,839, filed Jun. 27, 2015, Pelletier et al.
U.S. Appl. No. 15/034,543m filed May 4, 2016, Pelletier et al.
U.S. Appl. No. 15/035,006, filed May 6, 2016, Pelletier et al.
U.S. Appl. No. 15/982,644, filed May 17, 2018, Pelletier et al.
Alexander, J. et al., "Administration of the Soluble Complement Inhibitor, Crry-Ig, Reduces Inflammation and Aquaporin 4 Expression in Lupus Cerebritis," Biochimica et Biophysica Acta, 2003, 169-176.
Amiry-Moghaddam, M. et al., "Alpha-Syntrophin Deletion Removes the Perivascular But Not Endothelial Pool of Aquaporin-4 at the Blood-Brain Barrier and Delays the Development of Brain Edema in an Experimental Model of Acute Hyponatremia," The FASEB Journal, 2004, 18, 542-544.
Amiry-Moghaddam, M. et al. "Anchoring of Aquaporin-4 in Brain: Molecular Mechanisms and Implications for the Physiology and Pathophysiology of Water Transport," Neuroscience, 2004, 129, 999-1010.
Aoki, K. et al., "Enhanced Expression of Aquaporin 4 in Human Brain with Infarction," Acta Neuropathologica, 2003, 106, 121-124.
Aoki-Yoshino, K. et al., "Enhanced Expression of Aquaporin 4 in Human Brain with Inflammatory Diseases," Acta Neuropathologica, 2005, 110, 281-288.
Ayasoufi, K. et al., "Aquaporin 4 Blockade Improves Survival of Murine Heart Allografts Subjected to Prolonged Cold Ischemia," American Journal of Transplantation, 2018, 18, 1238-1246.
Banamine (Flunixin Meglumine), retrieved from https://web.archive.org/web/20110711140225/http://www.banamine.com/research/FlunixinMeglumine.asp, 1 page, face of article states: Jul. 11, 2011.
Bao, W. et al., "Selective mGluR5 Receptor Antagonist or Agonist Provides Neuroprotection in a Rat Model of Focal Cerebral Ischemia," Brain Research, 2001, 922, 173-179.
Bardutzky, J. et al., "Antiedema Therapy in Ischemic Stroke," Stroke, 2007, 38, 3084-3094.
Beeton, C. et al., "Induction and Monitoring of Active Delayed Type Hypersensitivity (DTH) in Rats," JoVE. 6. http://www.jove.com/index/Details.stp?ID=237, doi:10.3791/237, 2007, 2 pages.
Benga, O. et al., "Brain Water Channel Proteins in Health and Disease," Molecular Aspects of Medicine, 2012, 33, 562-578.
Bereczki, D. et al., "Cochrane Report: A Systematic Review of Mannitol Therapy for Acute Ischemic Stroke and Cerebral Parenchymal Hemorrhage," Stroke, 2000, 31, 2719-2722.

(56) References Cited

OTHER PUBLICATIONS

Bhattacharyya, S. et al., "Specific Effects of BCL10 Serine Mutations on Phosphorylations in Canonical and Noncanonical Pathways of NF-κB Activation Following Carrageenan," The American Journal of Physiology—Gastrointesintal and Liver Physiology, 2011, 301, G475-G486.
Binder, D. et al., "Increased Seizure Threshold in Mice Lacking Aquaporin-4 Water Channels," NeuroReport, 2004, 15 (2), 259-262.
Binder, D. et al., "Increased Seizure Duration and Slowed Potassium Kinetics in Mice Lacking Aquaporin-4 Water Channels," GLIA, 2006, 53, 631-636.
Binder, D. et al., "Aquaporin-4 and Epilepsy," GLIA, 2012, 60, 1203-1214.
Bloch, O. et al., "Aquaporin-4 Gene Deletion in Mice Increases Focal Edema Associated with Staphylococcal Brain Abscess," Journal of Neurochemistry, 2005, 95, 254-262.
Brown, L. et al., "In Vitro and In Vivo Hydrolysis of Salicylanilide N-Methylcarbamate and 4-Biphenylyl N-Methylcarbamate," Journal of Pharmaceutical Sciences, 1972, 61 (6), 858-860.
Caraci, F. et al., "Metabotropic Glutamate Receptors in Neurodegeneration/Neuroprotection: Still a Hot Topic?," Neurochemistry International, 2012, 61, 559-565.
Cernak, I., "Animal Models of Head Trauma," NeuroRx, 2005, 2, 410-422.
Chen, C. et al., "Animal Models of Nervous System Diseases," Jilin Science and Technology Press, 2007, pp. 252-254.
Chiamulera, C. et al., "Activation of Metabotropic Receptors has a Neuroprotective Effect in a Rodent Model of Focal Ischaemia," European Journal of Pharmacology, 1992, 216, 335-336.
Cooper, G. et al., "Transport of Volatile Solutes Through AQP1," Journal of Physiology, 2002, 542.1, 17-29.
Crash Trial, "Effect of Intravenous Corticosteroids on Death within 14 Days in 10008 Adults with Clinically Significant Head Injury (MRC CRASH Trial): Randomised Placebo Controlled Trial," Lancet, 2004, 264, 1321-1328.
Da, T. et al., "Aquaporin-4 Gene Disruption in Mice Protects Against Impaired Retinal Function and Cell Death after Ischemia," Investigative Ophthalmology & Visual Science, 2004, 45 (12), 4477-4483.
Dearden, N. et al., "Effect of High-Dose Dexamethasone on Outcome from Severe Head Injury," Journal of Neurosurgery, 1986, 64, 81-88.
Di Renzo, G. et al., "Why have Ionotropic and Metabotropic Glutamate Antagonists Failed in Stroke Therapy?," in New Strategies in Stroke Intervention, L. Annunziato, Ed., Humana Press, 2009, pp. 13-25.
Dibas, A. et al., "Changes in Ocular Aquaporin-4 (AQP4) Expression Following Retinal Injury," Molecular Vision, 2008, 14, 1770-1783.
Ding, F., Neurobiology, Science Press, 2007, pp. 421-423.
Ding, T. et al., "Knockdown a Water Channel Protein, Aquaporin-4, Induced Glioblastoma Cell Apoptosis," PLOS ONE, 2013, 8 (8), e66751, 9 pages, doi:10.1371/journal.pone.0066751.
Dixon, C. et al., "A Controlled Cortical Impact Model of Traumatic Brain Injury in the Rat," Journal of Neuroscience Methods, 1991, 39, 253-262.
Dudek, F. et al., "Regulation of Brain Water: Is there a Role for Aquaporins in Epilepsy?," Epilepsy Currents, 2005, 5 (3), 104-106, retrieved on Jul. 22, 2015, from http://www.ncbi.nlm.nih.gov/pmc/articles/PMC1198631/.
Eid, T. et al., "Loss of Perivascular Aquaporin 4 May Underlie Deficient Water and $K^+$ Homeostasis in the Human Epileptogenic Hippocampus," Proceedings of the National Academy of Sciences, 2005, 102 (4), 1193-1198.
Eisenberg, H. et al., "High-Dose Barbiturate Control of Elevated Intracranial Pressure in Patients with Severe Head Injury," Journal of Neurosurgery, 1988, 69, 15-23.
Elati, C. et al., "Novel Synthesis of Fosphenytoin: Anti-Convulsant Prodrug," Synthetic Communications, 2008, 38, 2950-2957.
Engel, O. et al., "Modeling Stroke in Mice—Middle Cerebral Artery Occlusion with the Filament Model," Journal of Visualized Experiments, 2011, 47, e2423, 5 pages, doi:10.3791/2423.
Esteva-Font, C. et al., "Experimental Evaluation of Proposed Small-Molecule Inhibitors of Water Channel Aquaporin-1," Molecular Pharmacology, 2016, 89, 686-693.
Farinas, J. et al., "Plasma Membrane Water Permeability of Cultured Cells and Epithelia Measured by Light Microscopy with Spatial Filtering," The Journal of General Physiology, 1997, 110, 283-296.
Fei, Z. et al., "Metabotropic Glutamate Receptor Antagonists and Agonists: Potential Neuroprotectors in Diffuse Brain Injury," Journal of Clinical Neuroscience, 2006, 13, 1023-1027.
Frigeri, A. et al., "Localization of Miwc and Glip Water Channel Homologs in Neuromuscular, Epithelial and Glandular Tissues," Journal of Cell Science, 1995, 108, 2993-3002.
Frigeri, A et al., "Immunolocalization of the Mercurial-Insensitive Water Channel and Glycerol Intrinsic Protein in Epithelial Cell Plasma Membranes," Proceedings of the National Academy of Sciences, 1995, 92, 4328-4331.
Gerber, J. et al., "Mechanisms of Injury in Bacterial Meningitis," Current Opinion in Neurology, 2010, 23, 312-318.
Gotoh, O. et al., "Ischemic Brain Edema Following Occlusion of the Middle Cerebral Artery in the Rat. I: The Time Courses of the Brain Water, Sodium and Potassium Contents and Blood Brain Barrier Permeability to $^{125}$I-Albumin," Stroke, 1985, 16 (1), 101-109.
Gullans, S., "Control of Brain Volume During Hyperosmolar and Hypoosmolar Conditions," Annual Review of Medicine, 1993, 44, 289-301.
Gunnarson, E. et al., "Identification of a Molecular Target for Glutamate Regulation of Astrocyte Water Permeability," Glia, 2008, 56, 587-596.
Guo, Q. et al., "Progesterone Administration Modulates AQP4 Expression and Edema After Traumatic Brain Injury in Male Rats," Experimental Neurology, 2006, 198, 469-478.
Hall, G. et al., "Inhibitor-kB Kinase-β regulates LPS-Induced TNF-α Production in Cardiac Myocytes Through Modulation of NF-κB p65 Subunit Phosphorylation," American Journal of Heart Physiology—Heart and Circulatory Physiology, 2005, 289, H2103-H2111.
Himadri, P. et al., "Role of Oxidative Stress and Inflammation in Hypoxia-Induced Cerebral Edema: A Molecular Approach," High Altitude Medicine & Biology, 2010, 11 (3), 231-244.
Hiroaki, Y. et al., "Implications of the Aquaporin-4 Structure on Array Formation and Cell Adhesion," Journal of Molecular Biology, 2006, 355, 628-639.
Ho, J. et al., "Crystal Structure of Human Aquaporin 4 at 1.8 Å and Its Mechanism of Conductance," Proceedings of the National Academy of Sciences, 2009, 106 (18), 7437-7442.
Hsu, M. et al., "Potential Role of the Glial Water Channel Aquaporin-4 in Epilepsy," Neuron Glia Biology, 2008, doi: 10.1017/S1740925X08000112, 11 pages.
Huber, V. et al., "Identification of Arylsulfonamides as Aquaporin 4 Inhibitors," Bioorganic and Medicinal Chemistry Letters, 2007, 17, 1270-1273.
Huber, V. et al., "Identification of Aquaporin 4 Inhibitors Using in vitro and in silico Methods," Bioorganic & Medicinal Chemistry, 2009, 17, 411-417.
Huber, V. et al., "Inhibition of Aquaporin 4 by Antiepileptic Drugs," Bioorganic & Medicinal Chemistry, 2009, 17, 418-424.
Igarashi,H. et al., "Pretreatment with a Novel Aquaporin 4 Inhibitor, TGN-020, Significantly Reduces Ischemic Cerebral Edema," Neurological Sciences, 2011, 32, 113-116.
Ikeshima-Kataoka, H., "Neuroimmunological Implications of AQP4 in Astrocytes," International Journal of Molecular Sciences, 2016, 17, 1306, 16 pages, doi:10.3390/ijms17081306.
International Preliminary Report on Patentability for International Application No. PCT/US2013/040194, dated Nov. 11, 2014, 8 pages.
International Search Report for International Application No. PCT/US2013/040194, dated Dec. 20, 2013, 5 pages.
International Search Report for International Application No. PCT/US2014/064432, dated Apr. 13, 2015, 5 pages.

(56) References Cited

OTHER PUBLICATIONS

International Search Report for International Application No. PCT/US2014/064441, dated Feb. 13, 2015, 4 pages.
International Search Report for International Application No. PCT/US2014/064447, dated Apr. 6, 2015, 5 pages.
International Search Report for International Application No. PCT/US2015/060731, dated Jan. 29, 2016, 4 pages.
International Search Report for International Application No. PCT/US2017/032563, dated Aug. 24, 2017, 3 pages.
Ito, J. et al., "Characterization of Edema by Diffusion-Weighted Imaging in Experimental Traumatic Brain Injury," Journal of Neurosurgery, 1996, 84, 97-103.
Jeyaseelan, K. et al., "Aquaporins: A Promising Target for Drug Development," Expert Opinion on Therapeutic Targets, 2006, 10 (6), 889-909.
Jung, J. et al., "Molecular Characterization of an Aquaporin cDNA from Brain: Candidate Osmoreceptor and Regulator of Water Balance," Proceedings of the National Academy of Sciences, 1994, 91, 13052-13056.
Jüttler, E. et al., "Clinical Review: Therapy for Refractory Intracranial Hypertension in Ischaemic Stroke," Critical Care, 2007, 11, 231, 14 pages, doi:10.1186/cc6087.
Kalita, J. et al., "Current Status of Osmotherapy in Intracerebral Hemorrhage," Neurology India, 2003, 51 (1), 104-109.
Kamegawa, A. et al., "Two-dimensional Crystal Structure of Aquaporin-4 Bound to the Inhibitor Acetazolamide," Microscopy, 2016, 65 (2), 177-184.
Kamon, J. et al., "A Novel IKKβ Inhibitor Stimulates Adiponectin Levels and Ameliorates Obesity-Linked Insulin Resistance," Biochemical and Biophysical Research Communications, 2004, 323, 242-248.
Katada, R. et al., "Greatly Improved Survival and Neuroprotection in Aquaporin-4-Knockout Mice Following Global Cerebral Ischemia," The FASEB Journal, 2014, 28, 10 pages, face of article states: published online Nov. 1, 2013, doi: 10.1096/fj.13-231274.
Kaufmann, A. et al., "Ischemic Core and Penumbra in Human Stroke," Stroke, 1999, 30, 93-99.
Ke, C. et al., "Heterogeneous Responses of Aquaporin-4 in Oedema Formation in a Replicated Severe Traumatic Brain Injury Model in Rats," Neuroscience Letters, 2001, 301, 21-24.
Kiening, K. et al., "Decreased Hemispheric Aquaporin-4 is Linked to Evolving Brain Edema Following Controlled Cortical Impact Injury in Rats," Neuroscience Letters, 2002, 324, 105-108.
Krave, U. et al., "Transient, Powerful Pressures are Generated in the Brain by a Rotational Acceleration Impulse to the Head," European Journal of Neuroscience, 2005, 21, 2876-2882.
Lea, P. et al., "Neuroprotective Activity of the mGluR5 Antagonists MPEP and MTEP Against Acute Excitotoxicity Differs and Does Not Reflect Actions at mGluR5 Receptors," British Journal of Pharmacology, 2005, 145 (4), 527-534.
Lee, D. et al., "Decreased Expression of the Glial Water Channel Aquaporin-4 in the Intrahippocampal Kainic Acid Model of Epileptogenesis," Experimental Neurology, 2012, doi:10.1016/j.expneurolo.2012.02.002, 10 pages.
Lennon, V. et al., "IgG Marker of Optic-Spinal Multiple Sclerosis Binds to the Aquaporin-4 Water Channel," The Journal of Experimental Medicine, 2005, 202 (4), 473-477.
Li, L. et al., "Synthesis and Biological Evaluation of a Water Soluble Phosphate Prodrug of 3-Aminopyridine-2-carboxaldehyde Thiosemicarbazone (3-AP)," Bioorganic & Medicinal Chemistry Letters, 1998, 8, 3159-3164.
Li, L. et al., "Greatly Attenuated Experimental Autoimmune Encephalomyelitis in Aquaporin-4 Knockout Mice," BMC Neuroscience, 2009, 10, 94, 5 pages, doi:10.1186/1471-2202-10-94.
Li, L. et al., "Proinflammatory Role of Aquaporin-4 in Autoimmune Neuroinflammation," The FASEB Journal, 2011, 25, 1556-1566.
Loane, D. et al., "Activation of Metabotropic Glutamate Receptor 5 Modulates Microglial Reactivity and Neurotoxicity by Inhibiting NADPH Oxidase," The Journal of Biological Chemistry, 2009, 284 (23), 15629-15639.

Longa, E. et al., "Reversible Middle Cerebral Artery Occlusion Without Craniectomy in Rats," Stroke, 1989, 20, 84-91.
Ma, T. et al., "Generation and Phenotype of a Transgenic Knockout Mouse Lacking the Mercurial-Insensitive Water Channel Aquaporin-4," Journal of Clinical Investigation, 1997, 100 (5), 957-962.
Manley, G. et al., "Aquaporin-4 Deletion in Mice Reduces Brain Edema After Acute Water Intoxication and Ischemic Stroke," Nature Medicine, 2000, 6 (2), 159-163.
Manley, G. et al., "New Insights into Water Transport and Edema in the Central Nervous System from Phenotype Analysis of Aquaporin-4 Null Mice," Neuroscience, 2004, 129, 983-991.
Marmarou, A. et al., "Traumatic Brain Edema in Diffuse and Focal Injury: Cellular or Vasogenic?," Acta Neurochimrgica, 2006 [Supplement], 96, 24-29.
Mehlhorn, U. et al., "Myocardial Fluid Balance," European Journal of Cardio-throacic Surgery, 2001, 20, 1220-1230.
Meli, E. et al., "Activation of mGlul but not mGlu5 Metabotropic Glutamate Receptors Contributes to Postischemic Neuronal Injury In Vitro and In Vivo," Pharmacology, Biochemistry and Behavior, 2002, 73, 439-446.
Migliati, E. et al., "Inhibition of Aquaporin-1 and Aquaporin-4 Water Permeability by a Derivative of the Loop Diuretic Bumetanide Acting at an Internal Pore-Occluding Binding Site," Molecular Pharmacology, 2009, 76 (1), 105-112.
Mola, M. et al., "Automated Cell-Based Assay for Screening of Aquaporin Inhibitors," Analytical Chemistry, 2009, 81, 8219-8229.
Mola, M. et al., "Automated Cell-Based Assay for Screening of Aquaporin Inhibitors," Author Manuscript, available in PMC 2010, 24 pages, face of article states: Published in final edited form as: Anal Chem. Oct. 1, 2009; 81(19): 8219-8229. doi:10.1021/ac901526k.
Morimoto, Y. et al., "Acute Brain Swelling After Out-of-Hospital Cardiac Arrest: Pathogenesis and Outcome," Critical Care Medicine, 1993, 21 (1), 104-110.
Neely, J. et al., "Syntrophin-Dependent Expression and Localization of Aquaporin-4 Water Channel Protein," Proceedings of the National Academy of Sciences, 2001, 98 (24), 14108-14113.
Nishikawa, S. et al., "A Molecular Targeting Against Nuclear Factor-kB, as a Chemotherapeutic Approach for Human Malignant Mesothelioma," Cancer Medicine, 2014, 3(2), 416-425.
Ogawa, M. et al., "The Mechanism of Anti-Inflammatory Effects of Prostaglandin $E_2$ Receptor Activation in Murine Cardiac Transplantation," Transplantation, 2009, 87, 1645-1653.
Onai, Y. et al., "Inhibition of IκB Phosphorylation in Cardiomyoctyes Attenuates Myocardial Ischemia/Reperfusion Injury," Cardiovascular Research, 2004, 63, 51-59.
Onai, Y. et al., "Inhibition of NF-κB Improves Left Ventricular Remodeling and Cardiac Dysfunction after Myocardial Infarction," American Journal of Heart Physiology—Heart and Circulatory Physiology, 2007, 292, H530-H538.
Papadopoulos, M. et al., "Aquaporin-4 Facilitates Reabsorption of Excess Fluid in Vasogenic Brain Edema," The FASEB Journal, published online Jun. 18, 2004, doi: 10.1096/fj.04-1723jfe, 18 pages.
Papadopoulos, M. et al., "Aquaporin-4 Facilitates Reabsorption of Excess Fluid in Vasogenic Brain Edema," The FASEB Journal, 2004, 18, 1291-1293.
Papadopoulos, M. et al., "Aquaporin-4 Gene Disruption in Mice Reduces Brain Swelling and Mortality in Pneumococcal Meningitis," The Journal of Biological Chemistry, 2005, 280 (14), 13906-13912.
Papadopoulos, M. et al., "Potential Utility of Aquaporin Modulators for Therapy of Brain Disorders," NIH Public Access, Author Manuscript, available in PMC 2013, 17 pages, face of article states: Published in final edited form as Prog Brain Res. 2008; 170: 589-601. doi:10.1016/S0079-6123(08)00446-9.
Papadopoulos, M. et al., "Aquaporin Water Channels in the Nervous System," NIH Public Access, Author Manuscript, available in PMC 2014, 28 pages, face of article states: Published in final edited form as Nat Rev Neurosci. Apr. 2013; 14(4): 265-277. doi:10.1038/nrn3468.

(56) References Cited

OTHER PUBLICATIONS

Quick, A. et al., "Pregnancy-Induced Up-Regulation of Aquaporin-4 Protein in Brain and Its Role in Eclampsia," The FASEB Journal, 2005, 19, 170-175.
Rabinstein, A., "Treatment of Cerebral Edema," The Neurologist, 2006, 12 (2), 59-73.
Rao, K. et al., "Marked Potentiation of Cell Swelling by Cytokines in Ammonia-Sensitized Cultured Astrocytes," Journal of Neuroinflammation, 2010, 7 (66), 8 pages.
Raslan, A. et al., "Medical Management of Cerebral Edema," Neurosurgical Focus, 2007, 22 (5), E12, 12 pages.
Raslan, A. et al., "Medical Management of Cerebral Edema," retrieved on Jan. 2, 2015, from http://www.medscape.com/viewarticle559004_6, 17 pages, face of article states: Neurosurgery Focus, 2007, 22 (5), E12.
Restrepo, D. et al., "Essential Activation of $Na^+$ -$H^+$ Exchange by $[H^+]_i$ in HL-60 Cells," American Journal of Physiology, 1990, 259, C490-0502.
Restrepo, L. et al., "Osmotherapy: A Call to Arms," and Response, Stroke, 2001, 32, 811-812.
Rutkovskiy, A. et al., "Aquaporin-4 in the Heart: Expression, Regulation and Functional Role in Ischemia," Basic Research in Cardiology, 2012, doi: 10.1007/s00395-012-0280-6, 13 pages.
Saadoun, S. et al., "Involvement of Aquaporin-4 in Astroglial Cell Migration and Glial Scar Formation," Journal of Cell Science, 2005, 118, 5691-5698.
Saadoun, S. et al., "Greatly Improved Neurological Outcome After Spinal Cord Compression Injury in AQP4-Deficient Mice," Brain, 2008, 131, 1087-1098.
Saadoun, S. et al., "AQP4 Gene Deletion in Mice Does Not Alter Blood-Brain Barrier Integrity or Brain Morphology," Neuroscience, 2009, 161, 764-772.
Saadoun, S. et al., "Aquaporin-4 in Brain and Spinal Cord Oedema," Neuroscience, 2010, 168, 1036-1046.
Schwartz, M. et al., "The University of Toronto Head Injury Treatment Study: A Prospective, Randomized Comparison of Pentobarbital and Mannitol," The Canadian Journal of Neurological Sciences, 1984, 11, 434-440.
Second Office Action issued in Chinese Patent Application No. 201380033198.7 dated Dec. 13, 2016, and English-language translation, 13 pages (8 pages Second Office Action, 5 pages translation).
Sepramaniam, S. et al. "MicroRNA 320a Functions as a Novel Endogenous Modulator of Aquaporins 1 and 4 as Well as a Potential Therapeutic Target in Cerebral Ischemia," The Journal of Biological Chemistry, 2010, 285 (38), 29223-29230.
Silberstein, C. et al., "Membrane Organization and Function of M1 and M23 Isoforms of Aquaporin-4 in Epithelial Cells," American Journal of Physiology, Renal Physiology, 2004, 287, F501-F511.
Slater, J. et al., "Discriminating Between Preservation and Reperfusion Injury in Human Cardiac Allografts Using Heart Weight and Left Ventricular Mass," retrieved on Jul. 23, 2015, from https://circ.ahajournals.org/content/92/9/223.full, 8 pages, face of article states: Circulation, 1995, 92, 223-227.
Slivka, A. et al., "High Dose Methylprednisolone Treatment in Experimental Focal Cerebral Ischemia," Experimental Neurology, 2001, 167, 166-172.
Sodium Phosphate, Cold Spring Harbor Protocols, doi:10.1101/pdb.rec8303, face of document states: copyright 2006, 1 page, retrieved Aug. 31, 2017 from: http://cshprotocols.cshlp.org/content/2006/1/pdb.rec8303.full?text_only =true.
Solenov, E. et al., "Sevenfold-Reduced Osmotic Water Permeability in Primary Astrocyte Cultures from AQP-4-Deficient Mice, Measured by a Fluorescence Quenching Method," American Journal of Physiology, Cell Physiology, 2004, 286, C426-C432.
Steiner, T. et al., "Treatment Options for Large Hemispheric Stroke," Neurology, 2001, 57 (Supplement 2), S61-68.
Stella, V. et al., Eds., Biotechnology: Pharmaceutical Aspects; Prodrugs: Challenges and Rewards, Part 2, Springer, New York, New York, 2007, p. 161.
Stroop, R. et al., "Magnetic Resonance Imaging Studies with Cluster Algorithm for Characterization of Brain Edema after Controlled Cortical Impact Injury (CCII)," Acta Neurochirurgica, 1998 [Supplement], 71, 303-305.
Su, C. et al., "Endogenous Memory CD8 T Cells Directly Mediate Cardiac Allograft Rejection," American Journal of Transplantation, 2014, 14, 568-579.
Sui, H. et al., "Structural Basis of Water-Specific Transport Through the AQP1 Water Channel," Nature, 2001, 414 (20/27), 872-878.
Sun, M. et al., "Regulation of Aquaporin-4 in a Traumatic Brain Injury Model in Rats," Journal of Neurosurgery, 2003, 98, 565-569.
Szabó, G. et al., "Systolic and Diastolic Properties and Myocardial Blood Flow in the Heterotopically Transplanted Rat Heart during Acute Cardiac Rejection," World Journal of Surgery, 2001, 25, 545-552.
Tait, M. et al. "Increased Brain Edema in AQP4-Null Mice in an Experimental Model of Subarachnoid Hemorrhage," Neuroscience, 2010, 167, 60-67.
Tajkhorshid, E. et al., "Control of the Selectivity of the Aquaporin Water Channel Family by Global Orientational Tuning," Science, 2002, 296, 525-530.
Taniguchi, M. et al., "Induction of Aquaporin-4 Water Channel mRNA After Focal Cerebral Ischemia in Rat," Molecular Brain Research, 2000, 78, 131-137.
Tanimura, Y. et al., "Acetazolamide Reversibly Inhibits Water Conduction by Aquaporin-4," Journal of Structural Biology, 2009, 166, 16-21.
Unterberg, A. et al., "Characterisation of Brain Edema Following 'Controlled Cortical Impact Injury' in Rats," Acta Neurochimrgica, 1997 [Supplement], 70, 106-108.
Unterberg, A. et al., "Edema and Brain Trauma," Neuroscience, 2004, 129, 1021-1029.
Van Hoek, A. et al., "Freeze-Fracture Analysis of Plasma Membranes of CHO Cells Stably Expressing Aquaporins 1-5," The Journal of Membrane Biology, 1998, 165, 243-254.
Verkman, A. et al., "Three Distinct Roles of Aquaporin-4 in Brain Function Revealed by Knockout Mice," Biochmica et Biophysica Acta, 2006, doi: 10.1016/j.bbamem.2006.02.018, 9 pages.
Verkman, A., "Aquaporins at a Glance," Journal of Cell Science, 2011, 124, 2107-2112.
Verkman, A. et al., "Aquaporin-4: Orthogonal Array Assembly, CNS Functions, and Role in Neuromyelitis Optica," Author Manuscript, available in PMC 2013, 16 pages, face of article states: Published in final edited form as: Acta Pharmacol Sin. 2011, 32(6), 702-710. doi:10.1038/aps.2011.27.
Verkman, A., "Aquaporins in Clinical Medicine," NIH Public Access, Author Manuscript, available in PMC 2013, 16 pages, face of article states: Published in final edited form as Annu Rev Med. 2012 63: 303-316. doi:10.1146/annurev-med-043010-193843.
Verkman, A. et al., "Aquaporins: Important But Elusive Drug Targets," Nature Reviews Drug Discovery, published online 2014, 19 pages, doi:10.1038/nrd4426.
Vizuete, M. et al., "Differential Upregulation of Aquaporin-4 mRNA Expression in Reactive Astrocytes After Brain Injury: Potential Role in Brain Edema," Neurobiology of Disease, 1999, 6, 245-258.
Wakatsuki, S. et al., "A Novel IKK Inhibitor Suppresses Heart Failure and Chronic Remodeling After Myocardial Ischemia Via MMP Alteration," Expert Opinion on Therapeutic Targets, 2008, 12 (12), 1469-1476.
Wang, F. et al., "Aquaporins as Potential Drug Targets," Acta Pharmacologica Sinica, 2006, 27 (4), 395-401.
Wang, J-W. et al., "Activation of Metabotropic Glutamate Receptor 5 Reduces the Secondary Brain Injury After Traumatic Brain Injury in Rats," Biochemical and Biophysical Research Communications, 2013, 430, 1016-1021.
Wang, X. et al., "Pre-Ischemic Treadmill Training Alleviates Brain Damage Via GLT-1-Mediated Signal Pathway After Ischemic Stroke in Rats," Neuroscience, 2014, 274, 393-402.
Wick, W. et al., "Brain Edema in Neurooncology: Radiological Assessment and Management," Onkologie, 2004, 27, 261-266.
Wilson, M. et al., "The Cerebral Effects of Ascent to High Altitudes," Lancet Neurology, 2009, 8, 175-191.

(56) References Cited

OTHER PUBLICATIONS

Wong, L. et al., "Vasoporessin V2 Receptor Antagonists," Cardiovascular Research, 2001, 51, 391-402.
Written Opinion of the International Searching Authority for International Application No. PCT/US2014/064432, dated Apr. 13, 2015, 7 pages.
Written Opinion of the International Searching Authority for International Application No. PCT/US2014/064441, dated Feb. 13, 2015, 8 pages.
Written Opinion of the International Searching Authority for International Application No. PCT/US2014/064447, dated Apr. 6, 2015, 6 pages.
Written Opinion of the International Searching Authority for International Application No. PCT/US2015/060731, dated Jan. 29, 2016, 8 pages.
Written Opinion of the International Searching Authority for International Application No. PCT/US2017/032563, dated Aug. 24, 2017, 5 pages.
Yang, B. et al., "The Mercurial Insensitive Water Channel (AQP-4) Forms Orthogonal Arrays in Stably Transfected Chinese Hamster Ovary Cells," The Journal of Biological Chemistry, 1996, 271 (9), 4577-4580.
Yang, B. et al., "Lack of Aquaporin-4 Water Transport Inhibition by Antiepileptics and Arylsulfonamides," Bioorganic & Medicinal Chemistry, 2008, 16, 7489-7493.
Yang, N. et al., "Effect of (S)-4C3HPG on Brain Damage in the Acute Stage of Moderate Traumatic Brain Injury Model of Mice and Underlying Mechanism," Acta Physiologica Sinica, 2010, 62 (6), 555-559.
Young, E., Chapter 9 entitled "IKK$\beta$ as a Therapeutic Intervention Point for Diseases Related to Inflammation," pp. 255-296, in Anti-Inflammatory Drug Discovery, Levin, J. et al., Eds., Royal Society of Chemistry, 2012.
Zador, Z et al., "Aquaporins: Role in Cerebral Edema and Brain Water Balance," Progress in Brain Research, 2007, 161, Chapter 12, 185-194.
Zeidel, M. et al., "Ultrastructure, Pharmacologic Inhibition, and Transport Selectivity of Aquaporin Channel-Forming Integral Protein in Proteoliposomes," Biochemistry, 1994, 33, 1606-1615.
Zelenina, M. et al., "Water Permeability of Aquaporin-4 is Decreased by Protein Kinase C and Dopamine," American Journal of Physiology, Renal Physiology, 2002, 283, F309-F318.
Zhang, D. et al., "Aquaporin Deletion in Mice Reduces Intraocular Pressure and Aqueous Fluid Production," The Journal of General Physiology, 2002, 119, 561-569.
Zhang, F. et al., "The Effect of Treadmill Training Pre-Exercise on Glutamate Receptor Expression in Rats After Cerebral Ischemia," International Journal of Molecular Sciences, 2010, 11, 2658-2669.
Zhang, Z-Y. et al., "Activation of mGluR5 Attenuates Microglial Activation and Neuronal Apoptosis in Early Brain Injury After Experimental Subarachnoid Hemorrhage in Rats," Neurochemical Research, 2015, 40, 1121-1132.
Zhao, F. et al., "Aquaporin-4 Deletion Ameliorates Hypoglycemia-induced BBB Permeability by Inhibiting Inflammatory Responses," Journal of Neuroinflammation, 2018, 15:157, 13 pages, https://doi.org/10.1186/s12974-018-1203-8.
Requirement for Restriction/Election dated Aug. 13, 2015, issued in U.S. Appl. No. 14/398,947, 10 pages.
Non-Final Office Action dated Dec. 18, 2015, issued in U.S. Appl. No. 14/398,947, 31 pages.
Final Office Action dated Sep. 20, 2016, issued in U.S. Appl. No. 14/398,947, 41 pages.
Advisory Action dated Dec. 16, 2016, issued in U.S. Appl. No. 14/398,947, 3 pages.
Non-Final Office Action dated Aug. 16, 2017, issued in U.S. Appl. No. 14/398,947, 24 pages.
Notice of Allowance dated Feb. 2, 2018, in U.S. Appl. No. 14/398,947, 10 pages.
Notice of Allowability and Examiner-Initiated Interview Summary dated Feb. 15, 2018, in U.S. Appl. No. 14/398,947, 7 pages.
Requirement for Restriction/Election dated Sep. 22, 2015, issued in U.S. Appl. No. 14/752,839, 6 pages.
Non-Final Office Action dated Mar. 8, 2016, issued in U.S. Appl. No. 14/752,839, 23 pages.
Final Office Action dated Aug. 30, 2016, issued in U.S. Appl. No. 14/752,839, 17 pages.
Notice of Allowance dated Oct. 7, 2016, in U.S. Appl. No. 14/752,839, 10 pages.
Aeromics, Anti-Edema Therapy for Patients Affected by Disabling and Life-Threatening Severe Ischemic Stroke, 6 pages, retrieved on Jul. 10, 2019, from: https://www.aeromics.com/.
Aeromics, "Aeromics Initiates Phase 1 Clinical Trial of CNS Edema Inhibitor AER-271 in Healthy Human Volunteers," dated Jul. 9, 2018, 4 pages, retrieved on Jul. 10, 2019, from: https://www.aeromics.com/press-releases/aeromics-inc-initiates-phase-1-trial-of-aer-271-in-healthy-human-volunteers.
Aeromics, "Aeromics, Inc. Appoints Pharmaceutical and Biotech Veterans Mark Day, Ph.D. and Thomas Zindrick, J.D. to Its Board of Directors," dated Aug. 16, 2018, 7 pages, retrieved on Jul. 10, 2019, from: https://www.aeromics.com/press-releases/aeromics-inc-appoints-pharmaceutical-and-biotech-veterans-mark-day-phd-and-thomas-zinclrick-jd-to-its-board-of-directors.
Farr, G. et al., "Aquaporin-4 Inhibitor AER-270 and Its Prodrug AER-271 Reduce Cerebral Edema and Improve Outcomes in Two Models of CNS Injury," Abstract M1905, Annals of Neurology, 2014, 76 (Supplement 18), S126-S127.
Farr, G. et al., "Phenylbenzamide Derivatives AER-270/271 Inhibit Aquaporin-4 Reducing Cerebral Edema and Improving Outcome in Two Models of CNS Injury," Poster presented at 2014 American Neurological Association Annual Meeting, 1 page.
Farr, G. et al., "Functionalized Phenylbenzamides Inhibit Aquaporin-4 Reducing Cerebral Edema and Improving Outcome in Two Models of CNS Injury," Neuroscience, 2019, accepted manuscript, https://doi.org/10.1016/j.neuroscience.2019.01.034, 46 pages.
Gomez-Cabrero, A. et al., "IMD-0354 Targets Breast Cancer Stem Cells: A Novel Approach for an Adjuvant to Chemotherapy to Prevent Multidrug Resistance in a Murine Model," PLoS One, 2013, 8 (8), e73607, 14 pages, doi:10.1371/journal.pone.0073607.
Kirby, A. et al., "The Reactivity of Phosphate Esters. Monoester Hydrolysis," Journal of the American Chemical Society, 1967, 89 (2), 415-423.
Kochanek, P. et al., "Operation Brain Trauma Therapy: 2016 Update," Military Medicine, 2018, 183, 303-312.
Maddahi, A. et al., "The Role of Tumor Necrosis Factor-$\alpha$ and TNF-$\alpha$ Receptors in Cerebral Arteries Following Cerebral Ischemia in Rat," Journal of Neuroinflammation, 2011, 8:107, 13 pages, doi:10.1186/1742-2094-8-107.
Monai, H. et al., "Adrenergic Receptor Antagonism Induces Neuroprotection and Facilitates Recovery from Acute Ischemic Stroke," Proceedings of the National Academy of Sciences, 2019, 116 (22), 11010-11019.
Nicosia, M. et al., "Aquaporin 4 Blockade Alters T Cell Trafficking Through a Novel Mechanism of S1PR1 Regulation," The Journal of Immunology, 2018, 200 (1 Supplement) 55.33, abstract only, 4 pages, retrieved on Oct. 10, 2018, from: http://www.jimmunol.org/content/200/1_Supplement/55.33.
Nicosia, M. et al., "Aquaporin 4 Inhibition Alters Chemokine Receptor Expression and T Cell Trafficking," Scientific Reports, 2019, 9:7417, 11 pages, https://doi.org/10.1038/s41598-019-43884-2.
Pippione, A. et al., "4-Hydroxy-N-4[3,5-bis(trifluoromethyl)phenyl]-1,2,5-thiadiazole-3-carboxamide: A Novel Inhibitor of the Canonical NF-$\kappa$B Cascade," Medicinal Chemistry Communications, 2017, 8, 1850-1855.
Sandhu, H. et al., "Upregulation of Contractile Endothelin Type B Receptors by Lipid-soluble Cigarette Smoking Particles in Rat Cerebral Arteries via Activation of MAPK," Toxicology and Applied Pharmacology, 2010, 249, 25-32.
Stokum, J. et al., "Molecular Pathophysiology of Cerebral Edema," Journal of Cerebral Blood Flow & Metabolism, 2016, 36 (3), 513-538.

(56) References Cited

OTHER PUBLICATIONS

Suzuki, J. et al., "Novel IκB Kinase Inhibitors for Treatment of Nuclear Factor-κB-related Diseases," Expert Opinion on Investiagional Drugs, 2011, 20 (3), 395-405.
Tanaka, A. et al., "Topical Application with a New NF-κB Inhibitor Improves Atopic Dermatitis in NC/NgaTnd Mice," Journal of Investigative Dermatology, 2007, 127, 855-863.
Verkman, A. et al., "The Aquaporin-4 Water Channel as a Potential Drug Target in Neurological Disorders," HHS Public Access, Author Manuscript, available in PMC 2019, 21 pages, face of article states: Published in final edited form as: *Expert Opin Ther Targets*. Dec. 2017; 21(12): 1161-1170. doi:10.1080/14728222.2017.1398236.
Wallisch, J. et al., "Effect of the Novel Aquaporin-4 Antagonist AER-271 in Combined TBI Plus Hemorrhagic Shock in Mice," Critical Care Medicine, 2015, 43 (12, Supplement), Abstract 23.
Wallisch, J. et al., "Aquaporin-4 Inhibitor AER-271 Blocks Early Cerebral Edema in Pediatric Rat Asphyxial Cardiac Arrest," Critical Care Medicine, 2016, 44 (12, Supplement), Abstract 718.
Wallisch, J. et al., "Evaluation of AER-271 in the Controlled Cortical Impact Model of Traumatic Brain Injury: An OBTT Consortium Study," Journal of Neurotrauma, 2016, 33, A-61, Abstract PSA-137.
Wallisch, J. et al., "Aquaporin-4 Inhibitor AER-271 Blocks Edema and Improves Outcome in Pediatric Rat Cardiac Arrest," Critical Care Medicine, 2017, 46 (1, Supplement), Abstract 49.
Wallisch, J. et al., "The Aquaporin-4 Inhibitor AER-271 Blocks Acute Cerebral Edema and Improves Early Outcome in a Pediatric Model of Asphyxial Cardiac Arrest," Pediatric Research, 2018, https://doi.org/10.1038/s41390-018-0215-5, 7 pages.
Yao, X. et al., "Mildly Reduced Brain Swelling and Improved Neurological Outcome in Aquaporin-4 Knockout Mice following Controlled Cortical Impact Brain Injury," Journal of Neurotrauma, 2015, 32, 1458-1464.

PRODRUG SALTS

CROSS REFERENCE TO RELATED APPLICATIONS

This application is a continuation of U.S. patent application Ser. No. 16/296,663 filed Mar. 8, 2019, now abandoned, which is a continuation of U.S. patent application Ser. No. 15/792,707 filed Oct. 24, 2017, now issued as U.S. Pat. No. 10,258,636, which is a divisional of U.S. patent application Ser. No. 15/034,274 filed May 4, 2016, now issued as U.S. Pat. No. 9,827,253, which is the National Stage Entry under 35 U.S.C. § 371 of International Application No. PCT/US2014/064447 filed Nov. 6, 2014, which claims priority to U.S. Provisional Application No. 61/900,878 filed Nov. 6, 2013, U.S. Provisional Application No. 61/900,919 filed Nov. 6, 2013, and U.S. Provisional Application No. 61/900,946 filed Nov. 6, 2013, the contents of each of which are incorporated herein by reference.

TECHNICAL FIELD

Provided are novel prodrug salts of selective aquaporin inhibitors, e.g., of aquaporin-4 and/or aquaporin-2, of Formula I as described below, their use as pharmaceuticals and pharmaceutical compositions comprising them, and novel intermediates used in and novel processes for their synthesis. These novel prodrug salts are useful e.g., in the prophylaxis, treatment, and control of aquaporin-mediated conditions, e.g., diseases of water imbalance, for example edema (particularly edema of the brain and spinal cord, e.g., following trauma or ischemic stroke, as well as edema associated with glioma, meningitis, acute mountain sickness, epileptic seizure, infection, metabolic disorder, hypoxia, water intoxication, hepatic failure, hepatic encephalopathy, diabetic ketoacidosis, abscess, eclampsia, Creutzfeldt-Jakob disease, and lupus cerebritis, as well as edema consequent to microgravity and/or radiation exposure, as well as optic nerve edema, e.g., optic nerve edema consequent to microgravity and/or radiation exposure, as well as edema consequent to an invasive central nervous system procedure, e.g., neurosurgery, endovascular clot removal, spinal tap, aneurysm repair, or deep brain stimulation, as well as retinal edema, as well as pulmonary edema, as well as brain swelling consequent to cardiac arrest, e.g., related to the development of the metabolic acidosis (e.g. lactic acidosis) due to hypoxia before the resuscitation period), as well as hyponatremia and excess fluid retention, ovarian hyperstimulation syndrome, and diseases such as epilepsy, retinal ischemia and other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, and glioblastoma, as well as fibromyalgia, multiple sclerosis, and migraines.

BACKGROUND

Aquaporins are cell membrane proteins that act as molecular water channels to mediate the flow of water in and out of the cells. While there is some degree of passive diffusion or osmosis of water across cell membranes, the rapid and selective transport of water in and out of cells involves aquaporins. These water channels selectively conduct water molecules in and out of the cell, while blocking the passage of ions and other solutes, thereby preserving the membrane potential of the cell. Aquaporins are found in virtually all life forms, from bacteria to plants to animals. In humans, they are found in cells throughout the body.

Aquaporin inhibitors, e.g., inhibitors of AQP4 and/or AQP2, may be of utility in the treatment or control of diseases of water imbalance, for example edema (particularly edema of the brain and spinal cord), hyponatremia, and excess fluid retention, as well as diseases such as epilepsy, retinal ischemia and other diseases of the eye, myocardial ischemia, myocardial ischemia/reperfusion injury, myocardial infarction, myocardial hypoxia, congestive heart failure, sepsis, and neuromyelitis optica, as well as migraines.

Prior to Applicants' filings, there have been no known specific, validated inhibitors of aquaporins, for example AQP4 or AQP2. Certain antiepileptic or sulfonamide drugs (e.g., acetylsulfanilamide, acetazolamide, 6-ethoxy-benzothiazole-2-sulfonamide, topiramate, zonisamide, phenytoin, lamotrigine, and sumatriptan) were at one point reported to be possible inhibitors of AQP4, but this later proved to be incorrect. Yang, et al., Bioorganic & Medicinal Chemistry (2008) 16: 7489-7493. No direct inhibitors of AQP2 have been reported.

Thus, there is a need for compounds that selectively inhibit aquaporins. In addition, there is a need for compounds that may be formulated to deliver compounds that selectively inhibit aquaporins, for example compounds which may be soluble in aqueous media and/or may be administered easily to patients.

BRIEF SUMMARY

Provided is a compound of Formula I

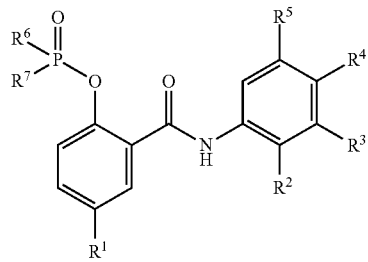

Formula I wherein:

$R^1$, $R^2$, $R^3$, $R^4$, and $R^5$ are independently H, halogen (e.g., Cl or Br), $C_{1-4}$-alkyl, $C_{1-4}$-haloalkyl (e.g., —$CF_3$), or cyano;

one of $R^6$ and $R^7$ is OH and the other is $O^-Q^+$ or both of $R^6$ and $R^7$ are $O^-Q^+$;

each Q+ is independently $Na^+$, $K^+$, $HOR^8NH_3^+$, $(HOR^8)_2NH_2^+$, or $(HOR^8)_3NH^+$; and each $R^8$ is independently $C_{1-4}$-alkylene (e.g., —$CH_2$—$CH_2$—).

Also provided is a compound of Formula I which is a compound of Formula II

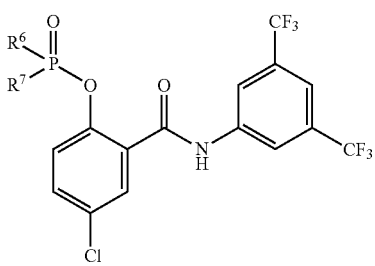

Formula II wherein:
one of $R^6$ and $R^7$ is OH and the other is $O^-Q^+$ or both of $R^6$ and $R^7$ are $O^-Q^+$;
each $Q^+$ is independently $K^+$, $HOR^8NH_3^+$, $(HOR^8)_2NH_2^+$, or $(HOR^8)_3NH^+$; and
each $R^8$ is independently $C_{1-4}$-alkylene (e.g., —$CH_2$—$CH_2$—).

Also provided is a pharmaceutical composition comprising a compound of Formula I, e.g., a compound of Formula II, and a pharmaceutically acceptable excipient.

Also provided is use of a compound of Formula I, e.g., a compound of Formula II, for the prophylaxis, treatment, and control of aquaporin-mediated conditions, e.g., diseases of water imbalance, for example edema (particularly edema of the brain and spinal cord, e.g., following trauma or ischemic stroke, as well as edema associated with glioma, meningitis, acute mountain sickness, epileptic seizure, infection, metabolic disorder, hypoxia, water intoxication, hepatic failure, hepatic encephalopathy, diabetic ketoacidosis, abscess, eclampsia, Creutzfeldt-Jakob disease, and lupus cerebritis, as well as edema consequent to microgravity and/or radiation exposure, as well as optic nerve edema, e.g., optic nerve edema consequent to microgravity and/or radiation exposure, as well as edema consequent to an invasive central nervous system procedure, e.g., neurosurgery, endovascular clot removal, spinal tap, aneurysm repair, or deep brain stimulation, as well as retinal edema, as well as brain swelling consequent to cardiac arrest, e.g., related to the development of the metabolic acidosis (e.g. lactic acidosis) due to hypoxia before the resuscitation period), as well as hyponatremia and excess fluid retention, ovarian hyperstimulation syndrome, as well as diseases such as epilepsy, retinal ischemia and other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, and glioblastoma, as well as migraines.

Also provided is a method of treating or controlling a disease or condition mediated by an aquaporin, e.g., diseases or conditions of water imbalance and other diseases, for example,
edema of the brain or spinal cord, e.g., cerebral edema, e.g. cerebral edema consequent to head trauma, ischemic stroke, glioma, meningitis, acute mountain sickness, epileptic seizure, infection, metabolic disorder, hypoxia (including general systemic hypoxia and hypoxia due to cardiac arrest), water intoxication, hepatic failure, hepatic encephalopathy, diabetic ketoacidosis, abscess, eclampsia, Creutzfeldt-Jakob disease, lupus cerebritis, cardiac arrest, microgravity and/or radiation exposure, or an invasive central nervous system procedure, e.g., neurosurgery, endovascular clot removal, spinal tap, aneurysm repair, or deep brain stimulation or, e.g., spinal cord edema consequent to spinal cord trauma, e.g., spinal cord compression; or
optic nerve edema, e.g., optic nerve edema consequent to microgravity and/or radiation exposure; or
retinal edema; or
hyponatremia or excessive fluid retention, e.g., consequent to heart failure (HF), liver cirrhosis, nephrotic disorder, syndrome of inappropriate antidiuretic hormone secretion (SIADH), or infertility treatment; or
ovarian hyperstimulation syndrome; or
epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or glioblastoma;
or migraines,
comprising administering to a patient in need thereof a therapeutically effective amount of a compound of Formula I, e.g., a compound of Formula II.

Also provided is a compound of Formula III

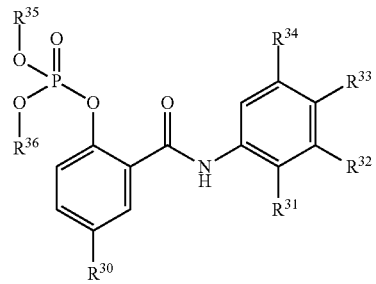

wherein:
$R^{30}$, $R^{31}$, $R^{32}$, $R^{33}$, and $R^{34}$ are independently H, halogen (e.g., Cl or Br), $C_{1-4}$-alkyl, $C_{1-4}$-haloalkyl (e.g., —$CF_3$), or cyano; and
$R^{35}$ and $R^{36}$ are independently protecting groups, e.g., wherein $R^{35}$ and $R^{36}$ are independently a protecting group comprising Si, S, N, and/or O, e.g., wherein $R^{35}$ and $R^{36}$ are independently a protecting group comprising an optionally substituted cyclic or acyclic ether, an optionally substituted silyl (e.g., —$Si(C_{1-6}$-alkyl$)_3$, e.g., —$Si(C_{1-4}$-alkyl$)_3$, e.g., —$Si(CH_3)_3$), an optionally substituted silyl ether, an optionally substituted ester, an optionally substituted ketone, or an optionally substituted thioether, e.g., wherein $R^{35}$ and $R^{36}$ are independently —$CH_2OR'$, —$CH_2SR'$,

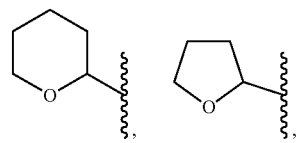

—$C(OC_{1-6}$-alkyl$)(R')_2$, —$CH(R')OR'$, —$C(R')_3$, —$Si(R'')_3$, —$C(O)R''$, or —$C(O)OR''$, wherein each $R'$ is independently H, $C_{1-6}$-alkyl (e.g., $C_{1-4}$-alkyl), —$CH_2Si(R'')_3$, —$CH_2$-Aryl (e.g., phenyl), —$C_{1-6}$-alkenyl, —$CH_2OSi(R'')_3$, alkoxyalkyl, or —$CH_2CH_2Si(R'')_3$ and each $R''$ is independently $C_{1-6}$-alkyl (e.g., $C_{1-4}$-alkyl) or aryl optionally substituted with alkoxy (e.g., —$C_{1-6}$-alkoxy, e.g., —$C_{1-4}$-alkoxy), halogen, cyano, or aryl (e.g., phenyl), wherein each $R'$ is optionally substituted with alkyl, alkoxyalkyl, or aryl, e.g., —(CH$_2$CH$_2$)$_n$—Si(R$^{37}$)$_3$), wherein each R$^{37}$ is independently C$_{1-6}$-alkyl, e.g., C$_{1-4}$-alkyl and n is 0 or 1, and wherein R$^{35}$ and R$^{36}$ are not both —CH$_2$—C$_6$H$_5$.

Also provided is a compound of Formula XX

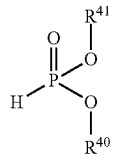

wherein:

R$^{40}$ and R$^{41}$ are independently protecting groups, e.g., wherein R$^{40}$ and R$^{41}$ are independently a protecting group comprising Si, S, N, and/or O, e.g., wherein R$^{40}$ and R$^{41}$ are independently a protecting group comprising an optionally substituted cyclic or acyclic ether, an optionally substituted silyl (e.g., —Si(C$_{1-6}$-alkyl)$_3$, e.g., —Si(C$_{1-4}$-alkyl)$_3$, e.g., —Si(CH$_3$)$_3$), an optionally substituted silyl ether, an optionally substituted ester, an optionally substituted ketone, or an optionally substituted thioether, e.g., wherein R$^{40}$ and R$^{41}$ are independently —CH$_2$OR', —CH$_2$SR',

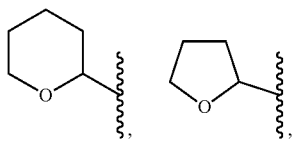

—C(OC$_{1-6}$-alkyl)(R')$_2$, —CH(R')OR', —C(R')$_3$, —Si(R")$_3$, —C(O)R", or —C(O)OR", wherein each R' is independently H, C$_{1-6}$-alkyl (e.g., C$_{1-4}$-alkyl), —CH$_2$Si(R")$_3$, —CH$_2$-Aryl (e.g., phenyl), —C$_{1-6}$-alkenyl, —CH$_2$OSi(R")$_3$, alkoxyalkyl, or —CH$_2$CH$_2$Si(R")$_3$ and each R" is independently C$_{1-6}$-alkyl (e.g., C$_{1-4}$-alkyl) or aryl optionally substituted with alkoxy (e.g., —C$_{1-6}$-alkoxy, e.g., —C$_{1-4}$-alkoxy), halogen, cyano, or aryl (e.g., phenyl), wherein each R' is optionally substituted with alkyl, alkoxyalkyl, or aryl, e.g., —(CH$_2$CH$_2$)$_n$—Si(R$^{37}$)$_3$), wherein each R$^{37}$ is independently C$_{1-6}$-alkyl, e.g., C$_{1-4}$-alkyl and n is 0 or 1, and wherein R$^{41}$ and R$^{341}$ are not both —CH$_2$—C$_6$H$_5$.

Also provided is a process for synthesizing a compound of Formula I, e.g., a compound of Formula II, comprising reacting a compound of Formula III and/or Formula XX.

Also provided is a process for synthesizing a compound of Formula III.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

$$V/V_0 = V_i + dV_{max}(1 - e^{(-kt)});$$

where $V/V_0$=relative brain volume, $V_i$=initial relative brain volume, $dV_{max}$=maximum change in relative brain volume, k=first order rate constant (min$^{-1}$), and t=time in minutes.

Figure 6:
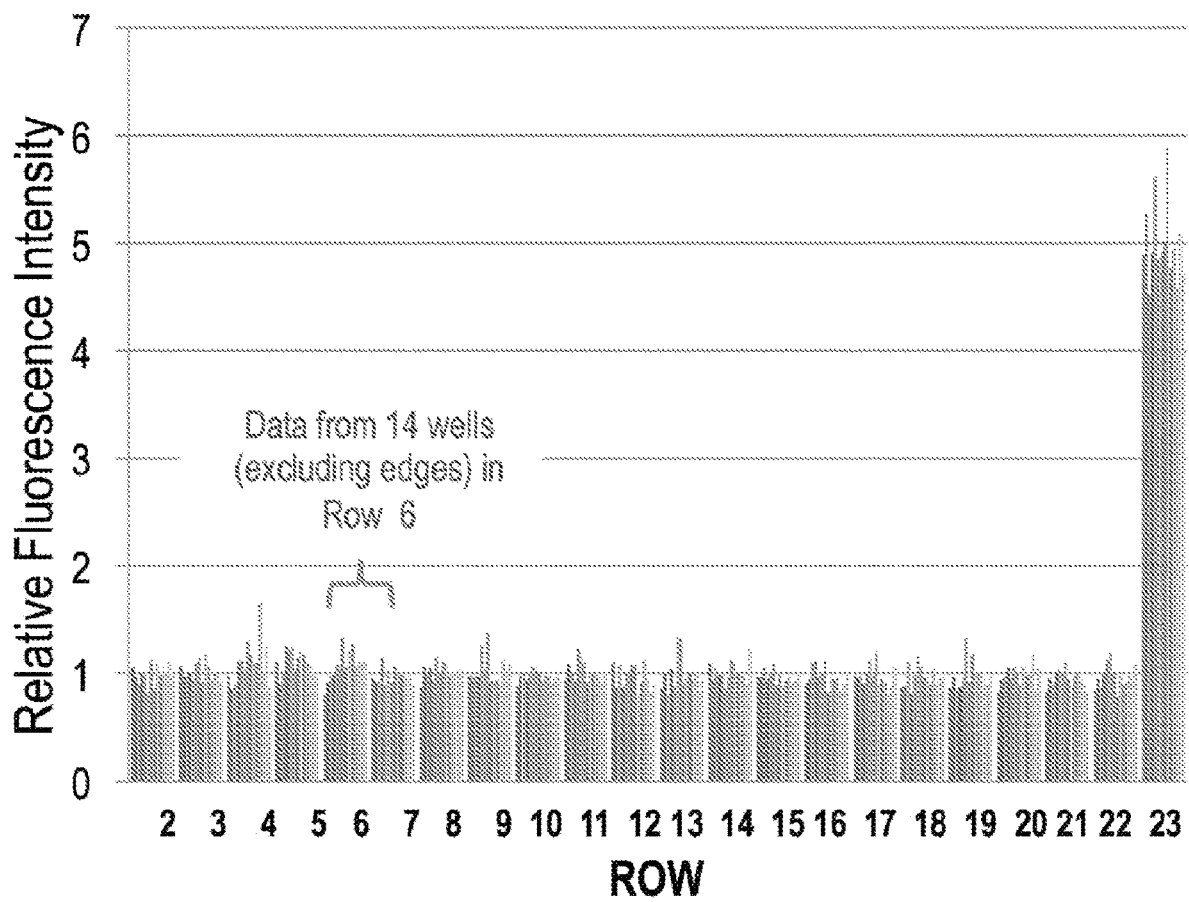

FIG. 6 depicts the calcein fluorescence end-point assay used for high throughput screening.

Figure 7:
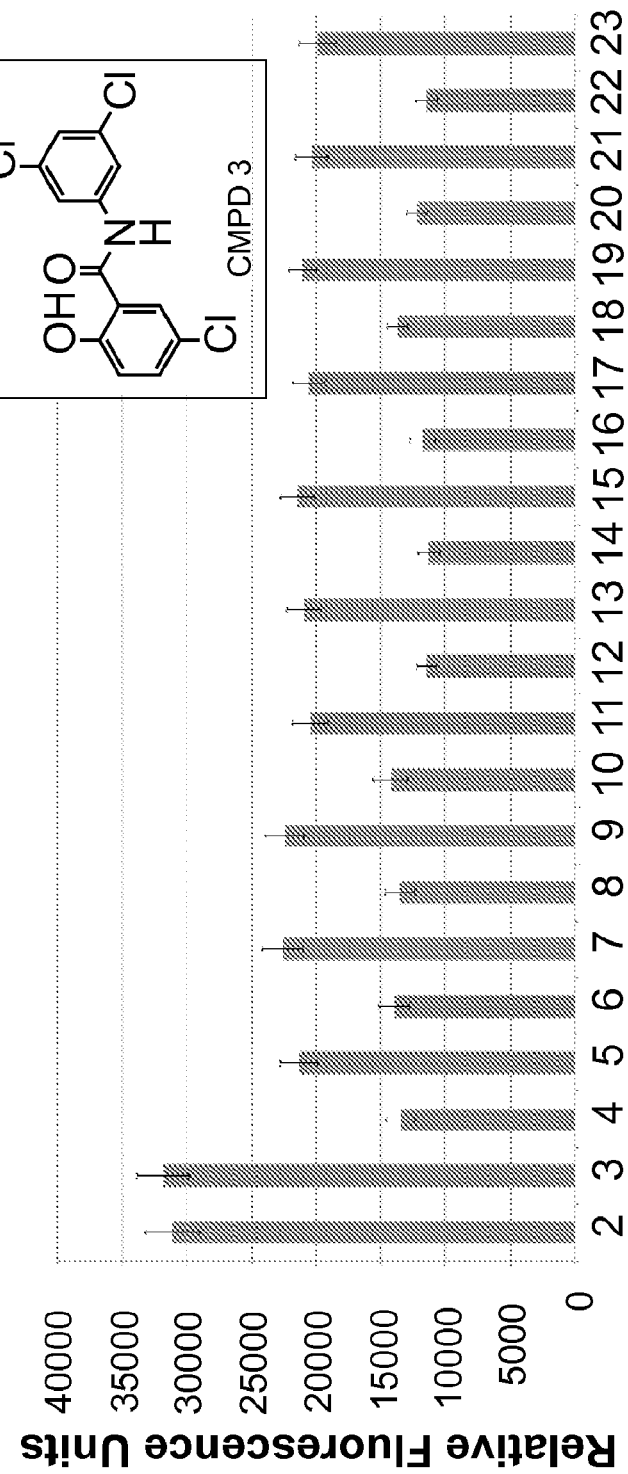

FIG. 7 depicts hit validation using the Cell Bursting Aquaporin Assay; inset shows the structure of 5-chloro-N-(3,5-dichlorophenyl)-2-hydroxybenzamide (Compound 3).

Figure 8:
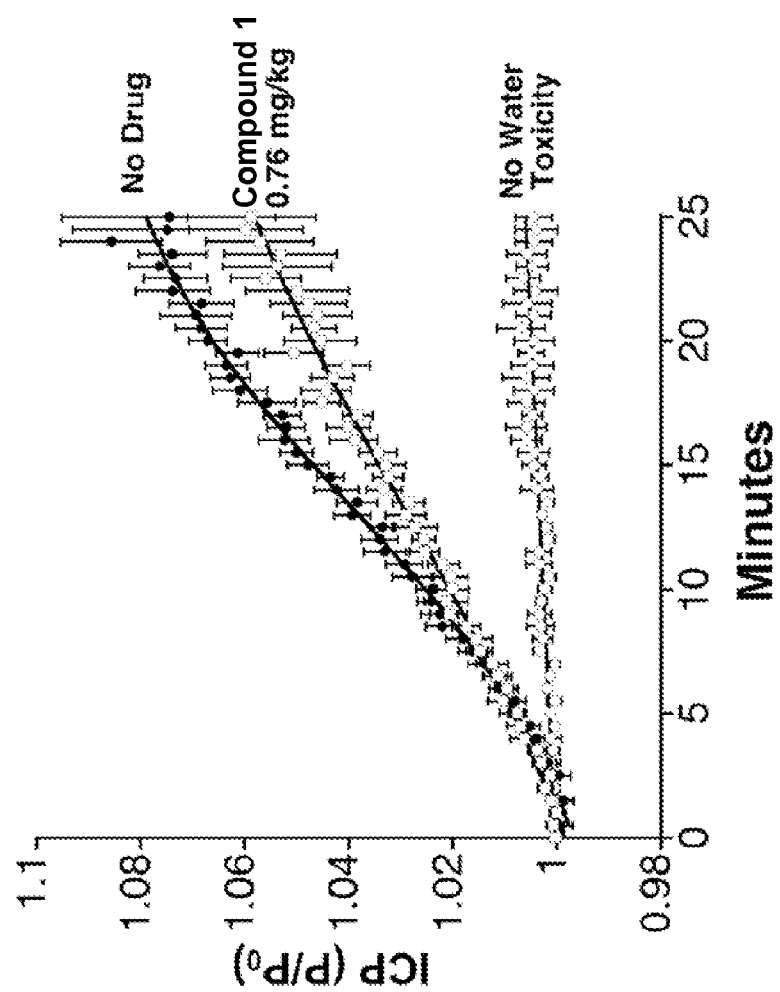

FIG. 8 depicts reduction in intracranial pressure (ICP) in the mouse water toxicity model with N-[3,5-bis(trifluoromethyl)phenyl]-5-chloro-2-hydroxybenzamide (Compound 1) at 0.76 mg/kg.

Figure 9:
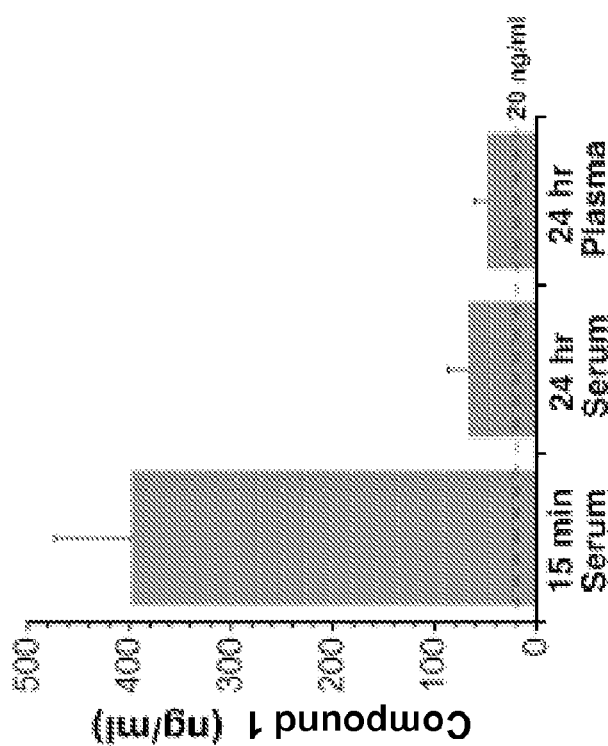

FIG. 9 depicts plasma and serum levels of N-[3,5-bis(trifluoromethyl)phenyl]-5-chloro-2-hydroxybenzamide (Compound 1) converted from 2-{[3,5-bis(trifluoromethyl)phenyl]carbamoyl}-4-chlorophenyl phosphate bis ethanolamine salt.

Figure 10:
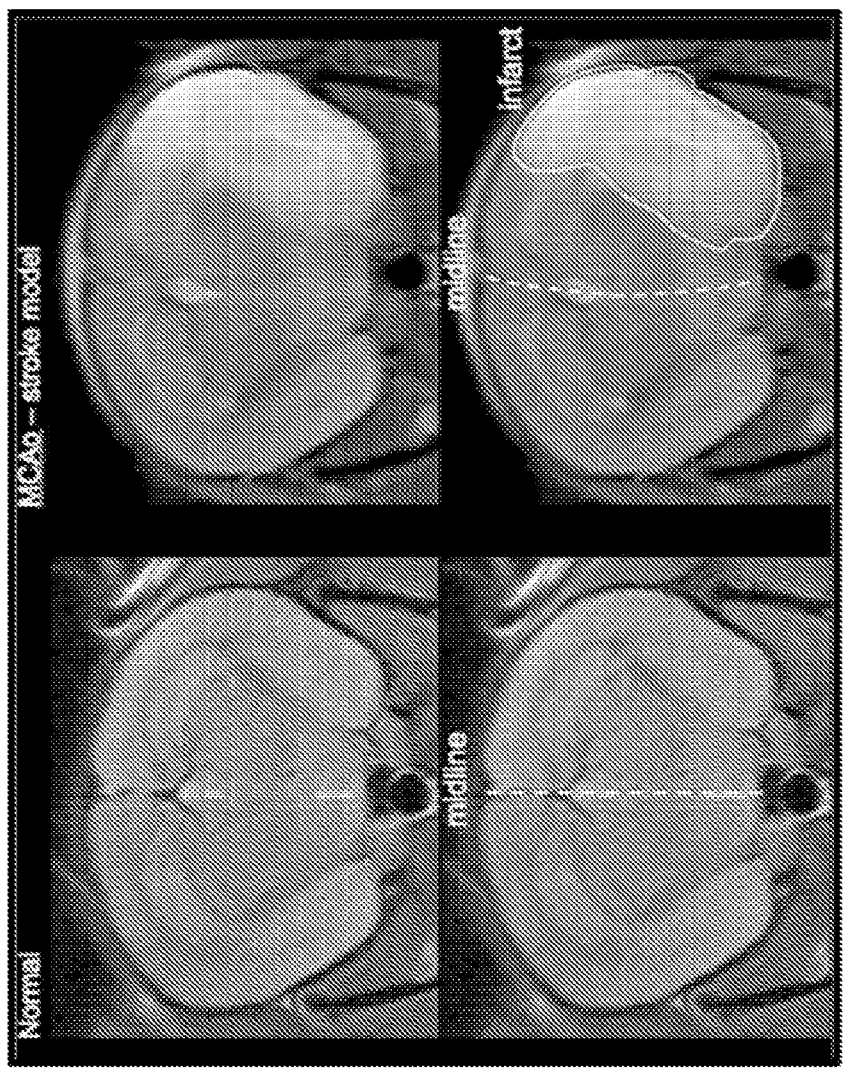

FIG. 10 depicts mouse middle cerebral artery occlusion (MCAo) model of ischemic stroke.

Figure 11:
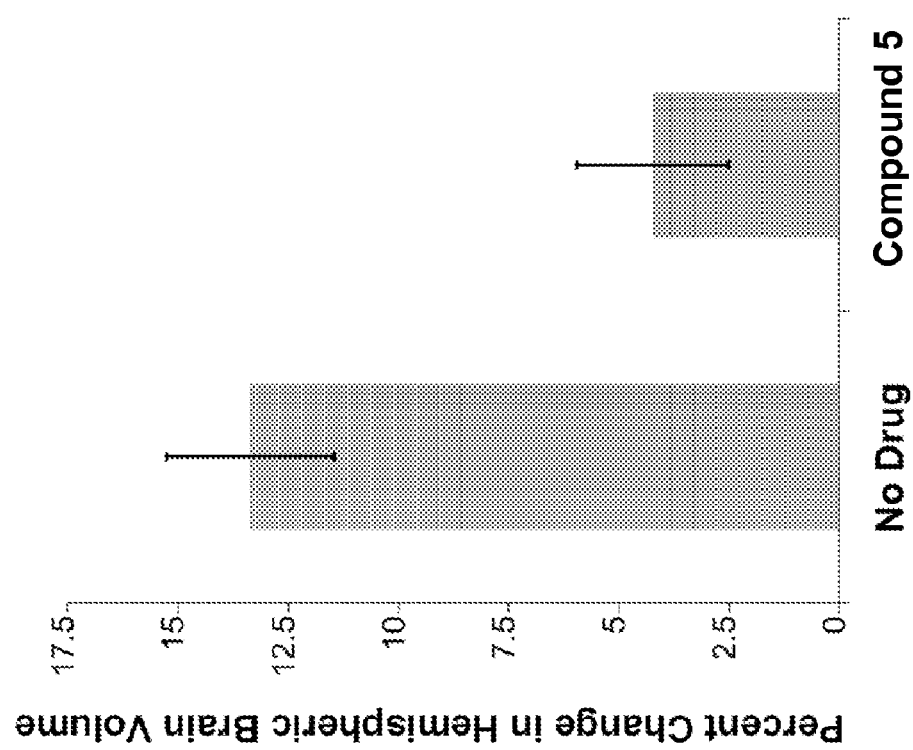

FIG. 11 depicts relative change in hemispheric brain volume in the mouse middle cerebral artery occlusion (MCAo) model.

Figure 12:
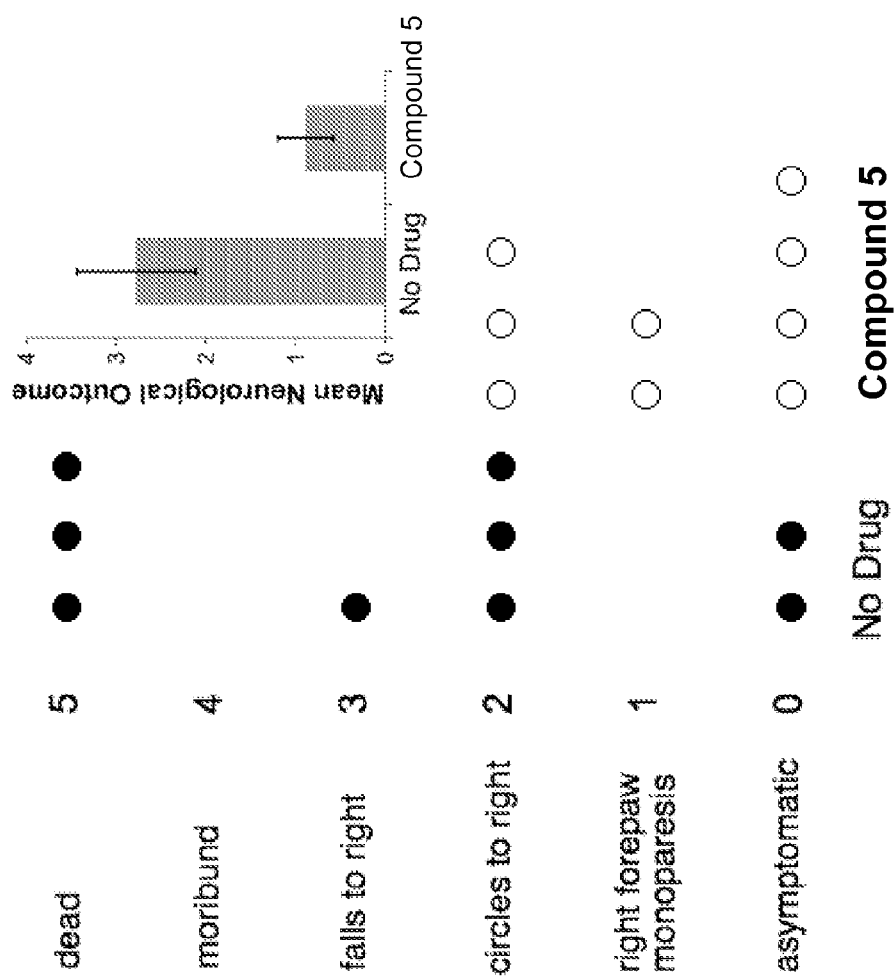

FIG. 12 depicts neurological outcome following MCAo in mice treated with saline (no drug, ●) or Compound 5 (o) (2-{[3,5-bis(trifluoromethyl)phenyl]carbamoyl}-4-chlorophenyl phosphate disodium salt).

DETAILED DESCRIPTION

The following description of the preferred embodiments is merely exemplary in nature and is in no way intended to limit the present disclosure, its application, or uses.

Expression of Aquaporin-4 (AQP4) is upregulated in animal models of trauma, stroke and water intoxication as well as around human malignant brain tumors. Aquaporin-4 (AQP4) has been shown to play a critical role in the development of cerebral and spinal cord edema. AQP4 provides the primary route for water movement across the blood-brain barrier (BBB) and glia limitans. AQP4 knockout mice, without the APQ4 gene, have improved survival compared to wild-type mice in models of ischemic stroke, water toxicity, bacterial meningitis, and spinal cord compression.

Cerebral edema (CE) may be generally divided into 2 major categories: vasogenic and cytotoxic. Vasogenic cerebral edema may occur when a breach in the BBB allows water and solutes to diffuse into the brain. It has been reported that AQP4-null mice have increased brain edema in a model of subarachnoid hemorrhage, suggesting that AQP4 may be required for the clearance of water collected in intercellular space. In contrast, cytotoxic cerebral edema may be initiated by ischemia which may result in reduced plasma osmolality rather than a disrupted BBB. Ischemia may lead to a drop in ATP levels, which is thought to slow the Na—K ATPase pump resulting in an uptake of $Na^+$ and $Cl^-$ through leakage pathways. The net effect may be a cellular osmotic imbalance, drawing $H_2O$ into cells—astrocytes more so than neurons—and leading to increased ICP. Mouse models for ischemic stroke, water toxicity, bacterial meningitis, and spinal-cord compression fall into this category. In these models, AQP4-null mice have been reported to have reduced CE pointing to AQP4 as the central pathway for water movement into the brain during the formation of cytotoxic CE. However, cytotoxic and vasogenic edema are not sharply divided categories; an injury that initially causes cytotoxic edema may be followed later, e.g., within the next hours to days, by vasogenic edema. This may suggest different treatments for cerebral edema at different times.

AQP4 inhibitors may be of further utility for certain ailments where control of AQP4-medited water movement may augment neuroexcitation (by alteration of neuronal potassium homeostasis) and prove beneficial by reducing neuronal excitation, for example ailments such as fibromyalgia, multiple sclerosis, migraines and seizures (in particular but not limited to seizures associated with epilepsy).

Glioblastoma is a common and aggressive malignant primary brain tumor. Inhibition of AQP4 in U87 human gliobastoma cell lines induces apoptosis.

Aquaporin-2 (AQP2) is the primary route of water movement at the collecting duct in the kidney. Blocking this water channel would lower water reabsorption without incurring electrolyte imbalances or interfering with vasopressin receptor-mediated signaling. Evidence that an AQP2 blocker would not produce electrolyte imbalances, and instead be an effective treatment for hyponatremia, comes from patients with diabetes insipidus who lack functional AQP2. They exhibit chronic aquaresis but—if normal hydration is maintained—do not demonstrate any other consequence of their long-term loss of AQP2 function.

Certain aquaporin inhibitors are described in International Patent Application No. PCT/US2013/040194, which is incorporated herein by reference in entirety.

In stroke or other severely debilitating diseases or conditions, for example where the patient may be unconscious or unable to swallow, an IV infusion or IV bolus may be preferred. In addition, when a patient has suffered a stroke, or traumatic brain or spinal cord injury, rapid achievement of therapeutically effective amounts of therapeutic agent may be important to a successful therapeutic outcome. However, a therapeutic agent with only a limited solubility in water and/or physiological media, may make IV administration of the therapeutic agent challenging.

Accordingly, in one embodiment, provided are novel prodrug salts of selective aquaporin inhibitors which may have improved solubility in aqueous and/or physiological media, e.g., novel prodrug salts of N-[3,5-bis(trifluoromethyl)phenyl]-5-chloro-2-hydroxybenzamide which may have improved solubility in aqueous and/or physiological media.

A prodrug form is a derivative of an active ingredient which converts in the body to the active ingredient, e.g., a prodrug of N-[3,5-bis(trifluoromethyl)phenyl]-5-chloro-2-hydroxybenzamide is a derivative of N-[3,5-bis(trifluoromethyl)phenyl]-5-chloro-2-hydroxybenzamide which converts in the body to N-[3,5-bis(trifluoromethyl)phenyl]-5-chloro-2-hydroxybenzamide.

As used herein, "alkyl" is a saturated hydrocarbon moiety, preferably having one to six carbon atoms, preferably having one to four carbon atoms, which may be linear or branched. A "$C_{1-4}$-alkyl" is an alkyl having one to four carbon atoms.

As used herein "alkylene" is a saturated hydrocarbon moiety, preferably having one to six carbon atoms, preferably having one to four carbon atoms, which may be linear or branched and which has two points of attachment. A $C_{1-4}$-alkylene is an alkylene having from one to four carbon atoms. For example, $C_1$-alkylene is methylene (—$CH_2$—).

As used herein, "halogen" is F, Cl, Br, or I.

As used herein, "haloalkyl" is a saturated hydrocarbon moiety, preferably having one to six carbon atoms, preferably having one to four carbon atoms, which may be linear or branched, and is mono-, di-, or tri-substituted with halogen. For di- or tri-substituted haloalkyl, the halogens may be the same (e.g., dichloromethyl) or different (e.g., chlorofluoromethyl). A $C_{1-4}$-haloalkyl is a haloalkyl having from one to four carbon atoms.

As used herein, "aryl" is a mono or polycyclic (e.g., bicyclic) aromatic hydrocarbon, preferably phenyl, which may be optionally substituted, e.g., optionally substituted with one or more groups independently selected from $C_{1-6}$ alkyl (e.g., methyl), halogen (e.g., Cl or F), $C_{1-6}$-haloalkyl (e.g., trifluoromethyl), hydroxy, and carboxy. In some embodiments, aryl, in addition to being substituted with the groups disclosed herein, is further substituted with an aryl or a heteroaryl to form, e.g., biphenyl or pyridylphenyl.

As used herein, "heteroaryl" is an mono or polycyclic (e.g., bicyclic) aromatic moiety wherein one or more of the atoms making up the aromatic ring is sulfur or nitrogen rather than carbon, e.g., pyridyl or thiadiazolyl, which may be optionally substituted, e.g., optionally substituted with one or more groups independently selected from $C_{1-6}$ alkyl (e.g., methyl), halogen (e.g., Cl or F), $C_{1-6}$-haloalkyl (e.g., trifluoromethyl), hydroxy, and carboxy.

As used herein, "hydroxy" is —OH.

As used herein, "carboxy" is —COOH.

As used herein, "patient" includes human or non-human (i.e., animal) patient. In a particular embodiment, the term encompasses both human and nonhuman. In another embodiment, the term encompasses nonhuman. In another embodiment, the term encompasses human.

As used herein, "therapeutically effective amount" refers to an amount effective, when administered to a human or non-human patient, to provide a therapeutic benefit such as amelioration of symptoms, slowing of disease progression, or prevention of disease. The specific dose of substance administered to obtain a therapeutic benefit will, of course, be determined by the particular circumstances surrounding the case, including, for example, the specific substance administered, the route of administration, the condition being treated, and the individual being treated.

As used herein, "fairly rapid" with respect to onset of action means that the time it takes after a compound is administered for a response to be observed is 30 minutes or less, for example 20 minutes or less, for example 15 minutes or less, for example 10 minutes or less, for example 5 minutes or less, for example 1 minute or less.

As used herein, "sodium phosphate" refers to sodium dihydrogen phosphate ($NaH_2PO_4$), disodium hydrogen phosphate ($Na_2HPO_4$), and trisodium phosphate ($Na_3PO_4$).

As used herein, "potassium phosphate" refers to potassium dihydrogen phosphate (KH$_2$PO$_4$), dipotassium hydrogen phosphate (K$_2$HPO$_4$), and tripotassium phosphate (K$_3$PO$_4$).

As used here, "bolus" refers to administration of a therapeutic agent in a single injection that lasts for a relatively short period of time, e.g., about 5 minutes or less, e.g., about 3 minutes or less. A bolus may rapidly deliver a therapeutically effective amount of the therapeutic agent to the blood.

In one embodiment, provided is a compound of Formula I

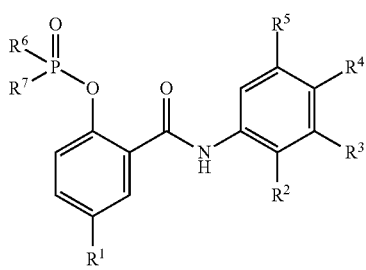

Formula I wherein:
$R^1$, $R^2$, $R^3$, $R^4$, and $R^5$ are independently H, halogen (e.g., Cl or Br), $C_{1-4}$-alkyl, $C_{1-4}$-haloalkyl (e.g., —CF$_3$), or cyano;
one of $R^6$ and $R^7$ is OH and the other is O$^-$Q$^+$ or both of $R^6$ and $R^7$ are O$^-$Q$^+$;
each Q$^-$ is independently Na$^-$, K$^-$, HOR$^8$NH$_3^-$, (HOR$^8$)$_2$NH$_2^-$, or (HOR$^8$)$_3$NH$^-$, e.g., K$^-$, HOR$^8$NH$_3^+$, (HOR$^8$)$_2$NH$_2^+$, or (HOR$^8$)$_3$NH$^+$, e.g., HOR$^8$NH$_3^+$, (HOR$^8$)$_2$NH$_2^+$, or (HOR$^8$)$_3$NH$^+$; and
each $R^8$ is independently $C_{1-4}$-alkylene (e.g., —CH$_2$—CH$_2$—).

Further provided is a compound of Formula I as follows:
1.1 Formula I wherein $R^1$, $R^2$, $R^3$, $R^4$, and $R^5$ are independently H, halogen (e.g., Cl or Br), $C_{1-4}$-haloalkyl (e.g., —CF$_3$), or cyano.
1.2 Formula I or 1.1 wherein $R^1$, $R^2$, $R^3$, $R^4$, and $R^5$ are independently H, halogen (e.g., Cl or Br), or $C_{1-4}$-haloalkyl (e.g., —CF$_3$).
1.3 Formula I, 1.1, or 1.2 wherein $R^1$, $R^3$, and $R^5$ are independently halogen (e.g., Cl or Br) or $C_{1-4}$-haloalkyl (e.g., —CF$_3$) and $R^2$ and $R^4$ are H.
1.4 Formula I or 1.1-1.3 wherein $R^1$, $R^3$, and $R^5$ are independently halogen (e.g., Cl or Br) and $R^2$ and $R^4$ are H.
1.5 Formula I or 1.1-1.4 wherein $R^1$, $R^3$, and $R^5$ are Cl and $R^2$ and $R^4$ are H.
1.6 Formula I or 1.1-1.3 wherein $R^1$, $R^3$, and $R^5$ are independently $C_{1-4}$-haloalkyl (e.g., —CF$_3$) and $R^2$ and $R^4$ are H.
1.7 Formula 1.6 wherein $R^1$, $R^3$, and $R^5$ are —CF$_3$.
1.8 Formula I or 1.1-1.3 wherein $R^1$, $R^3$, and $R^5$ are independently F, Cl, Br, or —CF$_3$ and $R^2$ and $R^4$ are H.
1.9 Formula I or 1.1-1.3 wherein $R^1$ is halogen (e.g., Cl or Br), $R^2$ and $R^4$ are H, and $R^3$ and $R^5$ are independently $C_{1-4}$-haloalkyl (e.g., —CF$_3$).
1.10 Formula 1.8 or 1.9 wherein $R^1$ is Cl or Br and $R^3$ and $R^5$ are —CF$_3$.
1.11 Formula 1.10 wherein $R^1$ is Cl.
1.12 Formula 1.10 wherein $R^1$ is Br.
1.13 Formula I or 1.1 wherein $R^1$, $R^2$, $R^3$, $R^4$, and $R^5$ are independently H, halogen (e.g., Cl or Br), or cyano.

1.14 Formula 1.13 wherein $R^1$ and $R^2$ are independently halogen (e.g., Cl or Br), $R^3$ and $R^5$ are H, and $R^4$ is cyano.
1.15 Formula 1.14 wherein $R^1$ and $R^2$ are Cl.
1.16 Formula I or 1.1-1.15 wherein $R^6$ is OH and $R^7$ is O$^-$Q$^+$.
1.17 Formula I or 1.1-1.15 wherein both $R^6$ and $R^7$ are O$^-$Q$^+$.
1.18 Formula I or 1.1-1.17 wherein each Q$^+$ is independently HOR$^8$NH$_3^+$, (HOR$^8$)$_2$NH$_2^+$, or (HOR$^8$)$_3$NH$^+$.
1.19 Formula I or 1.1-1.17 wherein each Q+ is independently HOR$^8$NH$_3^+$.
1.20 Formula I or 1.1-1.17 wherein each Q+ is independently (HOR$^8$)$_2$NH$_2^+$.
1.21 Formula I or 1.1-1.17 wherein each Q+ is independently (HOR$^8$)$_3$NH$^+$.
1.22 Formula I or 1.1-1.21 wherein each $R^8$ is —CH$_2$—CH$_2$—.
1.23 Formula I or 1.1-1.17 wherein each Q+ is Na$^+$.
1.24 Formula I or 1.1-1.17 wherein each Q+ is K$^+$.
1.25 Formula I wherein $R^1$ is halogen (e.g., Cl or Br), $R^2$ and $R^4$ are H, $R^3$ and $R^5$ are independently $C_{1-4}$-haloalkyl (e.g., —CF$_3$), $R^6$ is OH, and $R^7$ is O$^-$Q$^+$.
1.26 Formula 1.25 wherein $R^1$ is Cl or Br and $R^3$ and $R^5$ are —CF$_3$.
1.27 Formula 1.26 wherein $R^1$ is Cl.
1.28 Formula 1.25-1.27 wherein Q$^+$ is HOR$^8$NH$_3^+$.
1.29 Formula 1.28 wherein $R^8$ is —CH$_2$—CH$_2$—.
1.30 Formula 1.25-1.27 wherein Q$^+$ is (HOR$^8$)$_2$NH$_2^+$.
1.31 Formula 1.30 wherein $R^8$ is —CH$_2$—CH$_2$—.
1.32 Formula 1.25-1.27 wherein Q$^+$ is (HOR$^8$)$_3$NH$^+$.
1.33 Formula 1.32 wherein $R^8$ is —CH$_2$—CH$_2$—.
1.34 Formula 1.25-1.27 wherein Q$^+$ is K$^+$.
1.35 Formula I wherein $R^1$ is halogen (e.g., Cl or Br), $R^2$ and $R^4$ are H, $R^3$ and $R^5$ are independently $C_{1-4}$-haloalkyl (e.g., —CF$_3$), and both $R^6$ and $R^7$ are O$^-$QH$^+$.
1.36 Formula 1.35 wherein $R^1$ is Cl or Br and $R^3$ and $R^5$ are —CF$_3$.
1.37 Formula 1.36 wherein $R^1$ is Cl.
1.38 Formula 1.35-1.37 wherein each Q$^+$ is HOR$^8$NH$_3^+$.
1.39 Formula 1.38 wherein each $R^8$ is —CH$_2$—CH$_2$—.
1.40 Formula 1.35-1.37 wherein each Q$^+$ is (HOR$^8$)$_2$NH$_2^+$.
1.41 Formula 1.40 wherein each $R^8$ is —CH$_2$—CH$_2$—.
1.42 Formula 1.35-1.37 wherein each Q$^+$ is (HOR$^8$)$_3$NH$^+$.
1.43 Formula 1.42 wherein each $R^8$ is —CH$_2$—CH$_2$—.
1.44 Formula 1.35-1.37 wherein each Q$^+$ is K$^+$.
1.45 Formula I wherein the compound is:

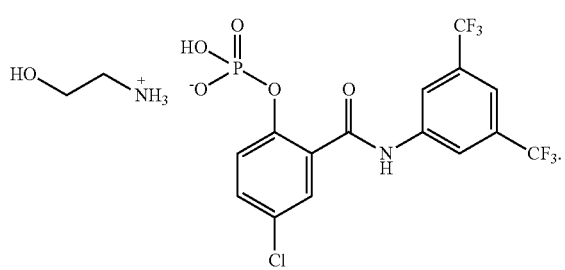

1.46 Formula I wherein the compound is:

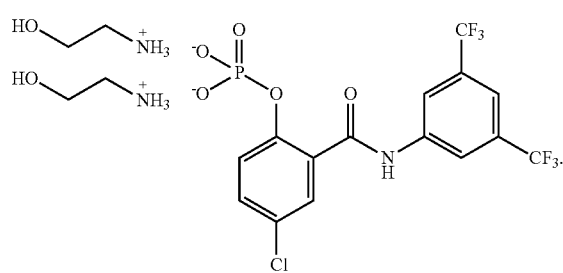

1.47 Formula I wherein the compound is:

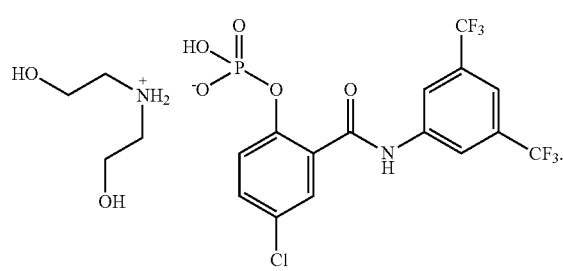

1.48 Formula I wherein the compound is:

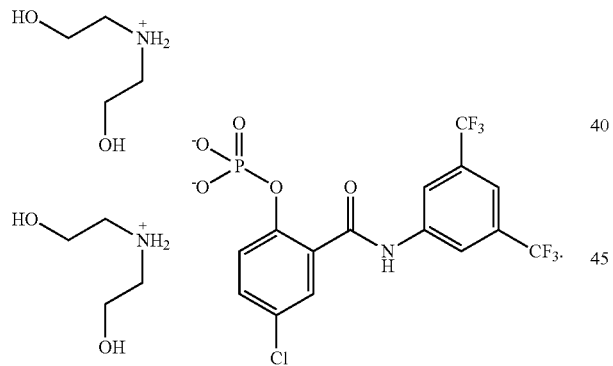

1.49 Formula I wherein the compound is:

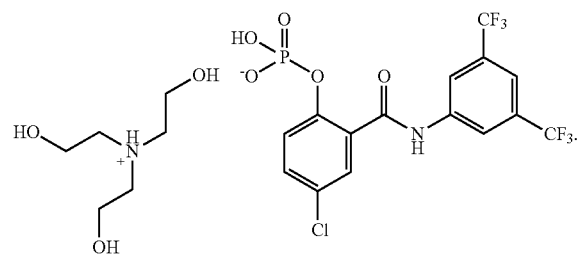

1.50 Formula I wherein the compound is

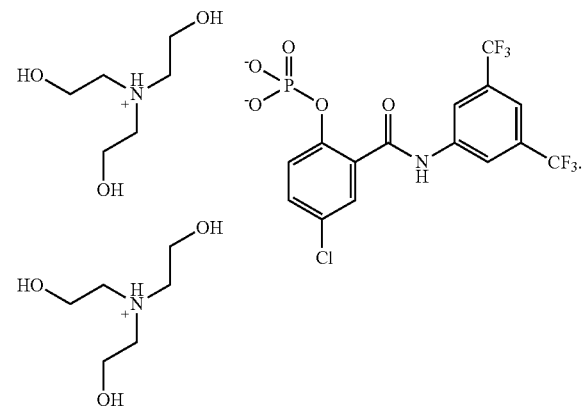

1.51 Formula I wherein the compound is

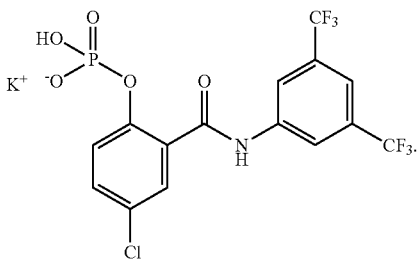

1.52 Formula I wherein the compound is

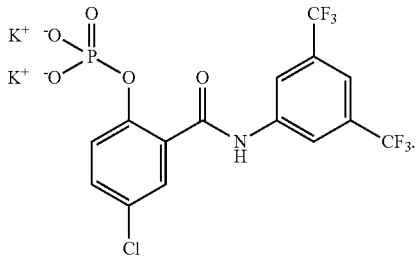

In another embodiment, provided is a compound of Formula I which is a compound of Formula II

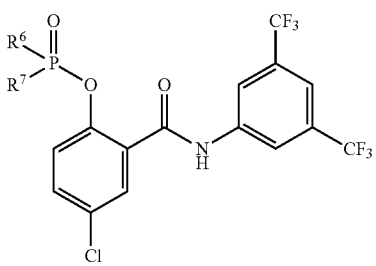

Formula II wherein:
one of $R^6$ and $R^7$ is OH and the other is $O^-Q^+$ or both of $R^6$ and $R^7$ are $O^-Q^+$;

each Q is independently K⁺, HOR⁸NH₃⁺, (HOR⁸)₂NH₂⁺, or (HOR⁸)₃NH⁺, e.g., HOR⁸NH₃⁺, (HOR⁸)₂NH₂⁺, or (HOR⁸)₃NH⁺; and each R⁸ is independently $C_{1-4}$-alkylene (e.g., —CH₂—CH₂—).

Further provided is a compound of Formula Ia as follows:

2.1 Formula II wherein R⁶ is OH and R⁷ is O⁻Q⁺.
2.2 Formula II or 2.1 wherein Q⁺ is HOR⁸NH₃⁺, (HOR⁸)₂NH₂⁺, or (HOR⁸)₃NH⁺.
2.3 Formula II, 2.1, or 2.2 wherein Q⁺ is HOR⁸NH₃⁺.
2.4 Formula 2.3 wherein R⁸ is —CH₂—CH₂—.
2.5 Formula II, 2.1, or 2.2 wherein Q⁺ is (HOR⁸)₂NH₂⁺.
2.6 Formula 2.5 wherein each R⁸ is —CH₂—CH₂—.
2.7 Formula II, 2.1, or 2.2 wherein Q⁺ is (HOR⁸)₃NH⁺.
2.8 Formula 2.7 wherein each R⁸ is —CH₂—CH₂—.
2.9 Formula II or 2.1 wherein Q⁺ is K⁺.
2.10 Formula II wherein both R⁶ and R⁷ are O⁻Q⁺.
2.11 Formula II or 2.10 wherein each Q⁺ is independently HOR⁸NH₃⁺, (HOR⁸)₂NH₂⁺, or (HOR⁸)₃NH⁺.
2.12 Formula II, 2.10, or 2.11 wherein each Q⁺ is independently HOR⁸NH₃⁺.
2.13 Formula 2.12 wherein each R⁸ is —CH₂—CH₂—.
2.14 Formula II, 2.10, or 2.11 wherein each Q⁺ is independently (HOR⁸)₂NH₂⁺.
2.15 Formula 2.14 wherein each R⁸ is —CH₂—CH₂—.
2.16 Formula II, 2.10, or 2.11 wherein each Q⁺ is independently (HOR⁸)₃NH⁺.
2.17 Formula 2.16 wherein each R⁸ is —CH₂—CH₂—.
2.18 Formula II or 2.10 wherein each Q⁺ is K⁺.
2.19 Formula II wherein the compound is:

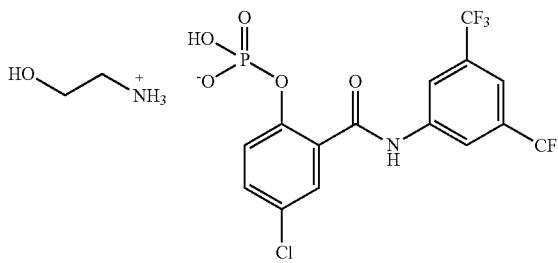

2.20 Formula II wherein the compound is:

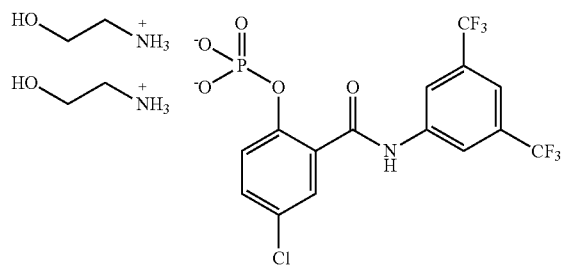

2.21 Formula II wherein the compound is:

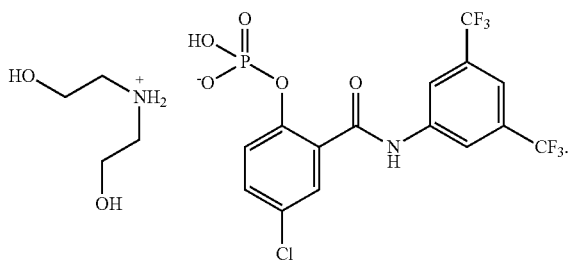

2.22 Formula II wherein the compound is:

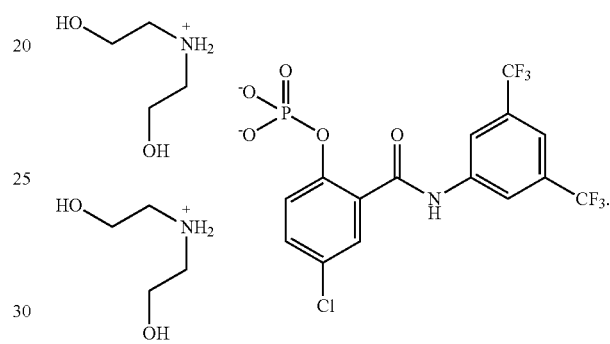

2.23 Formula II wherein the compound is:

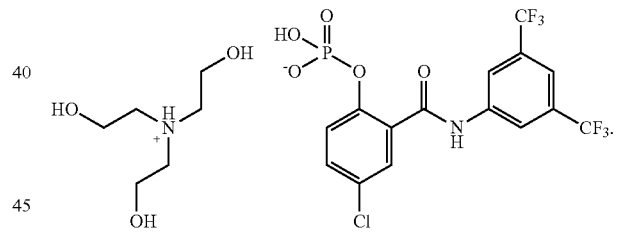

2.24 Formula II wherein the compound is

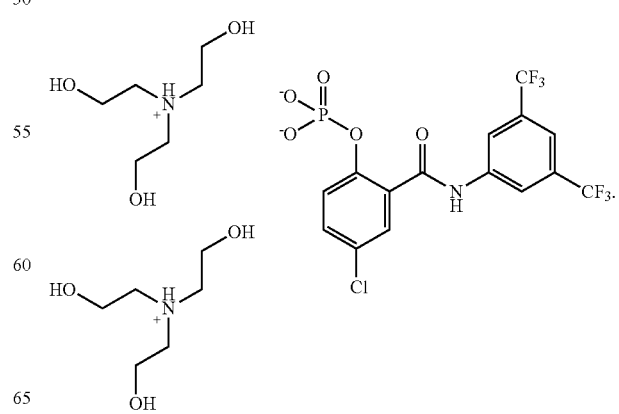

2.25 Formula II wherein the compound is

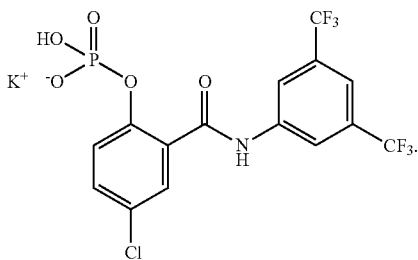

2.26 Formula II wherein the compound is

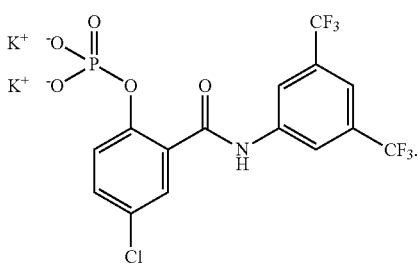

In yet another embodiment, provided is a pharmaceutical composition comprising a compound of Formula I, e.g., a compound of 1.1-1.52, and a pharmaceutically acceptable excipient.

In yet another embodiment, provided is a pharmaceutical composition comprising a compound of Formula II, e.g., a compound of 2.1-2.26, and a pharmaceutically acceptable excipient.

In yet another embodiment, provided is a method (Method A) of treating or controlling a disease or condition mediated by an aquaporin comprising administering to a patient in need thereof a therapeutically effective amount of a compound of Formula I, e.g., a compound of 1.1-1.52, or, e.g., a compound of Formula ITT, e.g., a compound of 2.1-2.26.

Further provided is Method A as follows:
A.1 Method A wherein the aquaporin is AQP4.
A.2 Method A or A.1 wherein the condition to be treated or controlled is edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, water intoxication, hepatic failure, hepatic encephalopathy, or diabetic ketoacidosis or, e.g., spinal cord edema, e.g., spinal cord edema consequent to spinal cord trauma, e.g., spinal cord compression.
A.3 Method A, A.1, or A.2 further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce cerebral metabolism ($CMO_2$); hemicraniectomy; administration of aspirin; administration of amantadine; intravenous thrombolysis (e.g. using rtPA); mechanical clot removal; angioplasty; and/or stents.
A.4 Method A.2 wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.
A.5 Method A.2 wherein the patient has suffered a stroke, head injury, or spinal injury.
A.6 Method A.5 wherein the patient has suffered a stroke, head injury or spinal injury within 12 hours, e.g. within 6 hours, preferably within 3 hours of commencing treatment.
A.7 Method A.2 wherein the patient is at elevated risk of suffering a stroke, head injury or spinal injury, e.g., in combat or in an athletic competition.
A.8 Method A or A.1-A.7 wherein the patient already has cerebral edema.
A.9 Method A or A.1-A.8 wherein the condition to be treated or controlled is cerebral edema consequent to a stroke or a traumatic brain injury.
A.10 Method A or A.1-A.9 wherein the condition to be treated or controlled is cerebral edema consequent to a middle cerebral artery stroke.
A.11 Method A or A.1-A.9 wherein the condition to be treated or controlled is cerebral edema consequent to closed head trauma.
A.12 Method A or A.1-A.4 wherein the condition to be treated or controlled is cerebral edema consequent to an epileptic seizure.
A.13 Method A or A.1-A.4 wherein the condition to be treated or controlled is cerebral edema consequent to an infection.
A.14 Method A or A.1-A.4 wherein the condition to be treated or controlled is cerebral edema consequent to a metabolic disorder.
A.15 Method A or A.1-A.4 wherein the condition to be treated or controlled is cerebral edema consequent to glioma.
A.16 Method A or A.1-A.4 wherein the condition to be treated or controlled is cerebral edema consequent to meningitis.
A.17 Method A or A.1-A.4 wherein the condition to be treated or controlled is cerebral edema consequent to acute mountain sickness.
A.18 Method A or A.1-A.4 wherein the condition to be treated or controlled is cerebral edema consequent to water intoxication.
A.19 Method A or A.1-A.4 wherein the condition to be treated or controlled is cerebral edema consequent to hepatic failure, hepatic encephalopathy, or diabetic ketoacidosis.
A.20 Method A or A.1-A.3 wherein the condition to be treated or controlled is cerebral edema consequent to an abscess.
A.21 Method A or A.1-A.3 wherein the condition to be treated or controlled is cerebral edema consequent to eclampsia.
A.22 Method A or A.1-A.3 wherein the condition to be treated or controlled is cerebral edema consequent to Creutzfeldt-Jakob disease.
A.23 Method A or A.1-A.3 wherein the condition to be treated or controlled is cerebral edema consequent to lupus cerebritis.
A.24 Method A or A.1-A.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

A.25 Method A or A.1-A.3 wherein the condition to be treated or controlled is cerebral edema consequent to microgravity and/or radiation exposure, e.g., exposure from space flight or from working with radioactive materials or from working in radioactive areas.

A.26 Method A or A.1-A.3 wherein the condition to be treated or controlled is cerebral edema consequent to an invasive central nervous system procedure, e.g., neurosurgery, endovascular clot removal, spinal tap, aneurysm repair, or deep brain stimulation.

A.27 Method A.25 or A.26 wherein the patient is at elevated risk of edema, e.g., due to microgravity and/or radiation exposure, neurosurgery, endovascular clot removal, spinal tap, aneurysm repair, or deep brain stimulation.

A.28 Method A.25 or A.26 wherein the patient already has edema.

A.29 Method A or A.1-A.28 wherein the edema is cytotoxic cerebral edema or is primarily cytotoxic cerebral edema.

A.30 Method A, A.1-A.19, or A.24 wherein the edema is cytotoxic cerebral edema or is primarily cytotoxic cerebral edema.

A.31 Method A, A.1, or A.2 wherein the condition to be treated or controlled is spinal cord edema, e.g., spinal cord edema consequent to a spinal cord trauma, e.g., spinal cord compression.

A.32 Method A.31 wherein the condition to be treated or controlled is spinal cord edema consequent to spinal cord compression.

A.33 Method A, A.1, or A.2 wherein the condition to be treated or controlled is optic nerve edema, e.g., optic nerve edema consequent to microgravity and/or radiation exposure, e.g., exposure from space flight or from working with radioactive materials or from working in radioactive areas.

A.34 Method A, A.1, or A.2 wherein the condition to be treated or controlled is retinal edema.

A.35 Method A, A.1, or A.2 wherein the condition to be treated or controlled is pulmonary edema.

A.36 Method A or A.1 wherein the condition to be treated or controlled is epilepsy.

A.37 Method A or A.1 wherein the condition to be treated or controlled is retinal ischemia or other diseases of the eye associated with abnormalities in intraocular pressure and/or tissue hydration.

A.38 Method A or A.1 wherein the condition to be treated or controlled is myocardial ischemia.

A.39 Method A or A.1, wherein the condition to be treated or controlled is myocardial ischemia/reperfusion injury.

A.40 Method A or A.1 wherein the condition to be treated or controlled is myocardial infarction.

A.41 Method A or A.1 wherein the condition to be treated or controlled is myocardial hypoxia.

A.42 Method A or A.1 wherein the condition to be treated or controlled is congestive heart failure.

A.43 Method A or A.1 wherein the condition to be treated or controlled is sepsis.

A.44 Method A or A.1 wherein the condition to be treated or controlled is a migraine.

A.45 Method A or A.1 wherein the condition to be treated or controlled is neuromyelitis optica.

A.46 Method A or A.1 wherein the condition to be treated or controlled is glioblastoma.

A.47 Method A or A.1 wherein the condition to be treated or controlled is fibromyalgia.

A.48 Method A or A.1 wherein the condition to be treated or controlled is multiple sclerosis.

A.49 Method A wherein the aquaporin is AQP2.

A.50 Method A or A.49 wherein the condition to be treated or controlled is hyponatremia or excessive fluid retention, e.g., consequent to heart failure (HF), for example congestive heart failure, liver cirrhosis, nephrotic disorder, syndrome of inappropriate antidiuretic hormone secretion (SIADH), or infertility treatment.

A.51 Method A, A.49, or A.50 wherein the condition to be treated or controlled is ovarian hyperstimulation syndrome.

A.52 Method A, A.49, or A.51 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

A.53 Method A or A.1-A.52 wherein the compound of Formula I, e.g., the compound of 1.1-1.52, or, e.g., the compound of Formula II, e.g., the compound of 2.1-2.26, is administered orally.

A.54 Method A or A.1-A.52 wherein the compound of Formula I, e.g., the compound of 1.1-1.52, or, e.g., the compound of Formula II, e.g., the compound of 2.1-2.26, is administered parenterally.

A.55 Method A.54 wherein the compound of Formula I, e.g., the compound of 1.1-1.52, or, e.g., the compound of Formula II, e.g., the compound of 2.1-2.26, is administered by injection, e.g., subcutaneously, intramuscularly, intravenously, or intrathecally, e.g., a bolus injected subcutaneously, intramuscularly, intravenously, or intrathecally.

A.56 Method A.55 wherein the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

A.57 Method A or A.1-A.56 wherein the patient is human.

A.58 Method A or A.1-A.57 wherein the onset of action after administration of the compound of Formula I, e.g., the compound of 1.1-1.52, or, e.g., the compound of Formula II, e.g., the compound of 2.1-2.26, is fairly rapid.

In yet another embodiment, provided is a method (Method B) of treating or controlling edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, hypoxia, water intoxication, hepatic failure, hepatic encephalopathy, diabetic ketoacidosis, abscess, eclampsia, Creutzfeldt-Jakob disease, lupus cerebritis, cardiac arrest, microgravity and/or radiation exposure, or invasive central nervous system procedures, e.g., neurosurgery, endovascular clot removal, spinal tap, aneurysm repair, or deep brain stimulation or, e.g., optic nerve edema, e.g., optic nerve edema consequent to microgravity and/or radiation exposure or, e.g., retinal edema or, e.g., spinal cord edema, e.g., spinal cord edema consequent to spinal cord trauma, e.g., spinal cord compression, or, e.g., pulmonary edema, comprising administering a therapeutically effective amount of a prodrug salt of an inhibitor of AQP4, e.g., a compound of Formula I, e.g., a compound of 1.1-1.52, or, e.g., a compound of Formula II, e.g., a compound of 2.1-2.26, to a patient in need thereof.

Further provided is Method B as follows:

- B.1 Method B further comprising a treatment selected from one or more of the following: optimal head and neck positioning to facilitate venous outflow, e.g. head elevation 30°; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce cerebral metabolism ($CMO_2$); hemicraniectomy; administration of aspirin; administration of amantadine; intravenous thrombolysis (e.g. using rtPA); mechanical clot removal; angioplasty; and/or stents.
- B.2 Method B wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.
- B.3 Method B wherein the patient has suffered a stroke, head injury, or spinal injury.
- B.4 Method B.3 wherein the patient has suffered a stroke, head injury or spinal injury within 12 hours, e.g. within 6 hours, preferably within 3 hours of commencing treatment.
- B.5 Method B wherein the patient is at elevated risk of suffering a stroke, head injury or spinal injury, e.g., in combat or in an athletic competition.
- B.6 Method B or B.1-B.5 wherein the patient already has cerebral edema.
- B.7 Method B or B.1-B.6 wherein the condition to be treated or controlled is cerebral edema consequent to a stroke or a traumatic brain injury.
- B.8 Method B or B.1-B.7 wherein the condition to be treated or controlled is cerebral edema consequent to a middle cerebral artery stroke.
- B.9 Method B or B.1-B.7 wherein the condition to be treated or controlled is cerebral edema consequent to a closed head trauma.
- B.10 Method B, B.1, or B.2 wherein the condition to be treated or controlled is cerebral edema consequent to an epileptic seizure.
- B.11 Method B, B.1, or B.2 wherein the condition to be treated or controlled is cerebral edema consequent to an infection.
- B.12 Method B, B.1, or B.2 wherein the condition to be treated or controlled is cerebral edema consequent to a metabolic disorder.
- B.13 Method B, B.1, or B.2 wherein the condition to be treated or controlled is cerebral edema consequent to glioma.
- B.14 Method B, B.1, or B.2 wherein the condition to be treated or controlled is cerebral edema consequent to meningitis.
- B.15 Method B, B.1, or B.2 wherein the condition to be treated or controlled is cerebral edema consequent to acute mountain sickness.
- B.16 Method B, B.1, or B.2 wherein the condition to be treated or controlled is cerebral edema consequent to water intoxication.
- B.17 Method B, B.1, or B.2 wherein the condition to be treated or controlled is cerebral edema consequent to hepatic failure, hepatic encephalopathy, or diabetic ketoacidosis.
- B.18 Method B or B. 1 wherein the condition to be treated or controlled is cerebral edema consequent to an abscess.
- B.19 Method B or B. 1 wherein the condition to be treated or controlled is cerebral edema consequent to eclampsia.
- B.20 Method B or B. 1 wherein the condition to be treated or controlled is cerebral edema consequent to Creutzfeldt-Jakob disease.
- B.21 Method B or B.1 wherein the condition to be treated or controlled is cerebral edema consequent to lupus cerebritis.
- B.22 Method B or B.1 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.
- B.23 Method B or B. 1 wherein the condition to be treated or controlled is cerebral consequent to microgravity exposure, e.g., exposure from space flight or from working with radioactive materials or from working in radioactive areas.
- B.24 Method B or B.1 wherein the condition to be treated or controlled is cerebral edema consequent to invasive central nervous system procedures, e.g., neurosurgery, endovascular clot removal, spinal tap, aneurysm repair, or deep brain stimulation.
- B.25 Method B.23 or B.24 wherein the patient is at elevated risk of edema, e.g., due to microgravity and/or radiation exposure, neurosurgery, endovascular clot removal, spinal tap, aneurysm repair, or deep brain stimulation.
- B.26 Method B.23 or B.24 wherein the patient already has edema.
- B.27 Method B or B.1-B.26 wherein the edema is cytotoxic cerebral edema or is primarily cytotoxic cerebral edema.
- B.28 Method B, B.1-B. 17, or B.22 wherein the edema is cytotoxic cerebral edema or is primarily cytotoxic cerebral edema.
- B.29 Method B wherein the condition to be treated or controlled is spinal cord edema, e.g., spinal cord edema consequent to spinal cord trauma, e.g., spinal cord compression.
- B.30 Method B.29 wherein the condition to be treated or controlled is spinal cord edema consequent to spinal cord compression.
- B.31 Method B wherein the condition to be treated or controlled is optic nerve edema, e.g., optic nerve edema consequent to microgravity and/or radiation exposure, e.g., exposure from space flight or from working with radioactive materials or from working in radioactive areas.
- B.32 Method B wherein the condition to be treated or controlled is retinal edema.
- B.33 Method B wherein the condition to be treated or controlled is pulmonary edema.
- B.34 Method B or B. 1-B.33 wherein the duration of treatment with the prodrug salt of an AQP4 inhibitor, e.g., a compound of Formula I, e.g., a compound of 1.1-1.52, or, e.g., a compound of Formula II, e.g., a compound of 2.1-2.26, is less than 21 days, e.g., less than 2 weeks, e.g., one week or less.

B.35 Method B or B. 1-B.34 wherein the prodrug salt of an AQP4 inhibitor, e.g., the compound of Formula I, e.g., the compound of 1.1-1.52, or, e.g., the compound of Formula II, e.g., the compound of 2.1-2.26, is administered orally.

B.36 Method B or B.1-B.34 wherein the prodrug salt of an AQP4 inhibitor, e.g., the compound of Formula I, e.g., the compound of 1.1-1.52, or, e.g., the compound of Formula II, e.g., the compound of 2.1-2.26, is administered parenterally.

B.37 Method B.36 wherein the prodrug salt of an AQP4 inhibitor, e.g., the compound of Formula I, e.g., the compound of 1.1-1.52, or, e.g., the compound of Formula II, e.g., the compound of 2.1-2.26, is administered by injection, e.g., subcutaneously, intramuscularly, intravenously, or intrathecally, e.g., a bolus administered subcutaneously, intramuscularly, intravenously, or intrathecally.

B.38 Method B.37 wherein the prodrug salt of an AQP4 inhibitor, e.g., the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

B.39 Method B or B.1-B.38 wherein the patient is human.

B.40 Method B or B. 1-B.39 wherein the onset of action after administration of the prodrug salt of an AQP4 inhibitor, e.g., the compound of Formula I, e.g., the compound of 1.1-1.52, or, e.g., the compound of Formula II, e.g., the compound of 2.1-2.26, is fairly rapid.

B.41 Method B or B.1-B.40 wherein the AQP4 inhibitor binds to AQP4.

In yet another embodiment, provided is a method (Method C) of treating or controlling a condition selected from hyponatremia and excessive fluid retention, e.g., consequent to heart failure (HF), for example congestive heart failure, liver cirrhosis, nephrotic disorder, syndrome of inappropriate antidiuretic hormone secretion (SIADH), or infertility treatment, comprising administering a therapeutically effective amount of a prodrug salt of an inhibitor of AQP2, e.g., a compound of Formula I, e.g., a compound of 1.1-1.52, or, e.g., a compound of Formula II, e.g., a compound of 2.1-2.26, to a patient in need thereof.

Further provided is Method C as follows:

C.1 Method C further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

C.2 Method C or C.1 wherein the prodrug salt of an AQP2 inhibitor, the compound of Formula I, e.g., the compound of 1.1-1.52, or, e.g., the compound of Formula II, e.g., the compound of 2.1-2.26, is administered orally.

C.3 Method C or C.1 wherein the prodrug salt of an AQP2 inhibitor, e.g., the compound of Formula I, e.g., the compound of 1.1-1.52, or, e.g., the compound of Formula II, e.g., the compound of 2.1-2.26, is administered parenterally.

C.4 Method C.3 wherein the prodrug salt of an AQP2 inhibitor, e.g., the compound of Formula I, e.g., the compound of 1.1-1.52, or, e.g., the compound of Formula II, e.g., the compound of 2.1-2.26, is administered by injection, e.g., subcutaneously, intramuscularly, intravenously, or intrathecally, e.g., a bolus injected subcutaneously, intramuscularly, intravenously, or intrathecally.

C.5 Method C.4 wherein the prodrug salt of an AQP2 inhibitor, e.g., the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

C.6 Method C or C.1-C.5 wherein the patient is human.

C.7 Method C or C.1-C.6 wherein the onset of action after administration of the prodrug salt of an AQP2 inhibitor, e.g., the compound of Formula I, e.g., the compound of 1.1-1.52, or, e.g., the compound of Formula II, e.g., the compound of 2.1-2.26, is fairly rapid.

C.8 Method C or C.1-C.7 wherein the AQP2 inhibitor binds to AQP2.

In yet another embodiment, provided is a method (Method D) of treating or controlling a condition selected from epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, glioblastoma, fibromyalgia, multiple sclerosis, and a migraine comprising administering a therapeutically effective amount of a prodrug salt of an inhibitor of AQP4, e.g., a compound of Formula 1, e.g., a compound of 1.1-1.52, or, e.g., a compound of Formula II, e.g., the compound of 2.1-2.26, to a patient in need thereof.

Further provided is Method D as follows:

D.1 Method D wherein the condition to be treated or controlled is retinal ischemia or other diseases of the eye associated with abnormalities in intraocular pressure and/or tissue hydration.

D.2 Method D wherein the condition to be treated or controlled is myocardial ischemia.

D.3 Method D wherein the condition to be treated or controlled is myocardial ischemia/reperfusion injury.

D.4 Method D wherein the condition to be treated or controlled is myocardial infarction.

D.5 Method D wherein the condition to be treated or controlled is myocardial hypoxia.

D.6 Method D wherein the condition to be treated or controlled is congestive heart failure.

D.7 Method D wherein the condition to be treated or controlled is sepsis.

D.8 Method D wherein the condition to be treated or controlled is neuromyelitis optica.

D.9 Method D wherein the condition to be treated or controlled is glioblastoma.

D.10 Method D wherein the condition to be treated or controlled is fibromyalgia.

D.11 Method D wherein the condition to be treated or controlled is multiple sclerosis.

D.12 Method D wherein the condition to be treated or controlled is a migraine.

D.13 Method D or D.1-D. 12 wherein the prodrug salt of an AQP4 inhibitor, e.g., the compound of Formula I, e.g., the compound of 1.1-1.52, or, e.g., the compound of Formula II, e.g., the compound of 2.1-2.26, is administered orally.

D.14 Method D or D.1-D.12 wherein the prodrug salt of an AQP4 inhibitor, e.g., the compound of Formula I, e.g., the compound of 1.1-1.52, or, e.g., the compound of Formula II, e.g., the compound of 2.1-2.26, is administered parenterally.

D.15 Method D. 14 wherein the prodrug salt of an AQP4 inhibitor, e.g., the compound of Formula I, e.g., the compound of 1.1-1.52, or, e.g., the compound of Formula II, e.g., the compound of 2.1-2.26, is administered by injection, e.g., subcutaneously, intramuscularly, intravenously, or intrathecally, e.g., a bolus injected subcutaneously, intramuscularly, intravenously, or intrathecally.

D.16 Method D.15 wherein the prodrug salt of an AQP4 inhibitor, e.g., the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

D.17 Method D or D.1-D.16 wherein the patient is human.

D.18 Method D or D.1-D.17 wherein the onset of action after administration of the prodrug salt of an AQP4 inhibitor, e.g., the compound of Formula 1, e.g., the compound of 1.1-1.52, or, e.g., the compound of Formula II, e.g., the compound of 2.1-2.26, is fairly rapid.

D.19 Method D or D.1-D.18 wherein the AQP4 inhibitor binds to AQP4.

In yet another embodiment, provided is a method (Method E) of treating or controlling a disease or condition mediated by an aquaporin comprising administering to a patient in need thereof a prodrug salt of the aquaporin inhibitor, e.g., a compound of Formula I, e.g., a compound of 1.1-1.52, or, e.g., a compound of Formula II, e.g., a compound of 2.1-2.26, in an amount effective to inhibit the aquaporin.

Further provided is Method E as follows:

E.1 Method E wherein the aquaporin is AQP4.

E.2 Method E or E.1 wherein the condition to be treated or controlled is selected from edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, water intoxication, hepatic failure, hepatic encephalopathy, or diabetic ketoacidosis or, e.g., spinal cord edema, e.g., spinal cord edema consequent to spinal cord trauma, e.g., spinal cord compression.

E.3 Method E, E. 1, or E.2 further comprising a treatment selected from one or more of the following: optimal head and neck positioning to facilitate venous outflow, e.g. head elevation 300; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce of cerebral metabolism ($CMO_2$); hemicraniectomy; administration of aspirin; administration of amantadine; intravenous thrombolysis (e.g. using rtPA); mechanical clot removal; angioplasty; and/or stents.

E.4 Method E.2 wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.

E.5 Method E.2 wherein the patient has suffered a stroke, head injury, or spinal injury.

E.6 Method E.5 wherein the patient has suffered a stroke, head injury or spinal injury within 12 hours, e.g. within 6 hours, preferably within 3 hours of commencing treatment.

E.7 Method E.2 wherein the patient is at elevated risk of suffering a stroke, head injury or spinal injury, e.g., in combat or in an athletic competition.

E.8 Method E or E.1-E.7 wherein the patient already has cerebral edema.

E.9 Method E or E.1-E.8 wherein the condition to be treated or controlled is cerebral edema consequent to a stroke or a traumatic brain injury.

E.10 Method E or E.1-E.9 wherein the condition to be treated or controlled is cerebral edema consequent to a middle cerebral artery stroke.

E.11 Method E or E.1-E.9 wherein the condition to be treated or controlled is cerebral edema consequent to a closed head trauma.

E.12 Method E or E.1-E.4 wherein the condition to be treated or controlled is cerebral edema consequent to an epileptic seizure.

E.13 Method E or E.1-E.4 wherein the condition to be treated or controlled is cerebral edema consequent an infection.

E.14 Method E or E.1-E.4 wherein the condition to be treated or controlled is cerebral edema consequent to a metabolic disorder.

E.15 Method E or E.1-E.4 wherein the condition to be treated or controlled is cerebral edema consequent to glioma.

E.16 Method E or E.1-E.4 wherein the condition to be treated or controlled is cerebral edema consequent to meningitis.

E.17 Method E or E.1-E.4 wherein the condition to be treated or controlled is cerebral edema consequent to acute mountain sickness.

E.18 Method E or E.1-E.4 wherein the condition to be treated or controlled is cerebral edema consequent to water intoxication.

E.19 Method E or E.1-E.4 wherein the condition to be treated or controlled is cerebral edema consequent to hepatic failure, hepatic encephalopathy, or diabetic ketoacidosis.

E.20 Method E or E.1-E.3 wherein the condition to be treated or controlled is cerebral edema consequent to an abscess.

E.21 Method E or E.1-E.3 wherein the condition to be treated or controlled is cerebral edema consequent to eclampsia.

E.22 Method E or E.1-E.3 wherein the condition to be treated or controlled is cerebral edema consequent to Creutzfeldt-Jakob disease.

E.23 Method E or E.1-E.3 wherein the condition to be treated or controlled is cerebral edema consequent to lupus cerebritis.

E.24 Method E or E.1-E.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

E.25 Method E or E.1-E.3 wherein the condition to be treated or controlled is cerebral edema consequent to microgravity and/or radiation exposure, e.g., exposure from space flight or from working with radioactive materials or from working in radioactive areas.

E.26 Method E or E.1-E.3 wherein the condition to be treated or controlled is cerebral edema consequent to invasive central nervous system procedures, e.g., neurosurgery, endovascular clot removal, spinal tap, aneurysm repair, or deep brain stimulation.

E.27 Method E.25 or E.26 wherein the patient is at elevated risk of edema, e.g., due to microgravity and/or radiation exposure, neurosurgery, endovascular clot removal, spinal tap, aneurysm repair, or deep brain stimulation.

E.28 Method E.25 or E.26 wherein the patient already has edema.

E.29 Method E or E.1-E.28 wherein the edema is cytotoxic cerebral edema or is primarily cytotoxic cerebral edema.

E.30 Method E, E.1-E.19, or E.24 wherein the edema is cytotoxic cerebral edema or is primarily cytotoxic cerebral edema.

E.31 Method E, E.1, or E.2 wherein the condition to be treated or controlled is spinal cord edema, e.g., spinal cord edema consequent to spinal cord trauma, e.g., spinal cord compression.

E.32 Method E.31 wherein the condition to be treated or controlled is spinal cord edema consequent to spinal cord compression.

E.33 Method E, E.1, or E.2 wherein the condition to be treated or controlled is optic nerve edema, e.g., optic nerve edema consequent to microgravity and/or radiation exposure, e.g., exposure from space flight or from working with radioactive materials or from working in radioactive areas.

E.34 Method E, E. 1, or E.2 wherein the condition to be treated or controlled is retinal edema.

E.35 Method E, E.1, or E.2 wherein the condition to be treated or controlled is pulmonary edema.

E.36 Method E or E.1 wherein the condition to be treated or controlled is epilepsy.

E.37 Method E or E. 1 wherein the condition to be treated or controlled is retinal ischemia or other diseases of the eye associated with abnormalities in intraocular pressure and/or tissue hydration.

E.38 Method E or E.1 wherein the condition to be treated or controlled is myocardial ischemia.

E.39 Method E or E. 1 wherein the condition to be treated or controlled is myocardial ischemia/reperfusion injury.

E.40 Method E or E.1 wherein the condition to be treated or controlled is myocardial infarction.

E.41 Method E or E.1 wherein the condition to be treated or controlled is myocardial hypoxia.

E.42 Method E or E. 1 wherein the condition to be treated or controlled is congestive heart failure.

E.43 Method E or E. 1 wherein the condition to be treated or controlled is sepsis.

E.44 Method E or E. 1 wherein the condition to be treated or controlled is a migraine.

E.45 Method E or E.1 wherein the condition to be treated or controlled is neuromyelitis optica.

E.46 Method E or E.1 wherein the condition to be treated or controlled is glioblastoma.

E.47 Method E or E. 1 wherein the condition to be treated or controlled is fibromyalgia.

E.48 Method E or E. 1 wherein the condition to be treated or controlled is multiple sclerosis.

E.49 Method E wherein the aquaporin is AQP2.

E.50 Method E or E.49 wherein the condition to be treated is hyponatremia or excessive fluid retention, e.g., consequent to heart failure (HF), for example congestive heart failure, liver cirrhosis, nephrotic disorder, syndrome of inappropriate antidiuretic hormone secretion (SIADH), or infertility treatment.

E.51 Method E, E.49, or E.50 wherein the condition to be treated or controlled is ovarian hyperstimulation syndrome.

E.52 Method E, E.49, or E.50 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

E.53 Method E or E.1-E.52 wherein the duration of treatment with the prodrug salt of the aquaporin inhibitor, e.g., the compound of Formula I, e.g., the compound of 1.1-1.52, or, e.g., the compound of Formula II, e.g., the compound of 2.1-2.26, is less than 21 days, e.g., less than 2 weeks, e.g., one week or less.

E.54 Method E or E.1-E.53 wherein the prodrug salt of the aquaporin inhibitor, e.g., the compound of Formula 1, e.g., the compound of 1.1-1.52, or, e.g., the compound of Formula II, e.g., the compound of 2.1-2.26, is administered orally.

E.55 Method E or E.1-E.53 wherein the prodrug salt of the aquaporin inhibitor, e.g., the compound of Formula I, e.g., the compound of 1.1-1.52, or, e.g., the compound of Formula II, e.g., the compound of 2.1-2.26, is administered parenterally.

E.56 Method E.55 wherein the prodrug salt of the aquaporin inhibitor, e.g., the compound of Formula I, e.g., the compound of 1.1-1.52, or, e.g., the compound of Formula II, e.g., the compound of 2.1-2.26, is administered by injection, e.g., subcutaneously, intramuscularly, intravenously, or intrathecally, e.g., a bolus injected subcutaneously, intramuscularly, intravenously, or intrathecally.

E.57 Method E.56 wherein the prodrug salt of the aquaporin inhibitor, e.g., the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

E.58 Method E or E.1-E.57 wherein the patient is human.

E.59 Method E or E.1-E.58 wherein the onset of action after administration of the prodrug salt of the aquaporin inhibitor, e.g., the compound of Formula I, e.g., the compound of 1.1-1.52, or, e.g., the compound of Formula II, e.g., the compound of 2.1-2.26, is fairly rapid.

In a further embodiment, provided is a method (Method F) of inhibiting an aquaporin in vivo comprising administering a compound of Formula I, e.g., a compound of 1.1-1.52, or, e.g., a compound of Formula II, e.g., a compound of 2.1-2.26, in an amount effective to inhibit the aquaporin.

Further provided is Method F as follows:

F.1 Method F wherein the aquaporin is AQP4.

F.2 Method F wherein the aquaporin is AQP2.

F.3 Method F, F.1, or F.2 wherein the compound of Formula T, e.g., the compound of 1.1-1.52, or, e.g., the compound of Formula II, e.g., the compound of 2.1-2.26, is administered orally.

F.4 Method F, F.1, or F.2 wherein the compound of Formula I, e.g., the compound of 1.1-1.52, or, e.g., the compound of Formula II, e.g., the compound of 2.1-2.26, is administered parenterally.

F.5 Method of F.4 wherein the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

In a further embodiment, provided is a method (Method G) to inhibit an aquaporin in a patient suffering from a disease or condition mediated by an aquaporin comprising administering an effective amount of a prodrug salt of an inhibitor of the aquaporin, e.g., a compound of Formula I, e.g., a compound of 1.1-1.52, or, e.g., a compound of Formula II, e.g., a compound of 2.1-2.26, to inhibit the aquaporin.

Further provided is Method G as follows:

G.1 Method G wherein the aquaporin is AQP4.

G.2 Method G or G.1 wherein the condition to be treated or controlled is edema, e.g. edema of the brain or spinal cord, e.g., cerebral edema, e.g. cerebral edema consequent to head trauma, ischemic stroke, glioma, meningitis, acute mountain sickness, epileptic seizure, infection, metabolic disorder, water intoxication, hepatic failure, hepatic encephalopathy, or diabetic ketoacidosis or, e.g., spinal cord edema, e.g., spinal cord edema consequent to spinal cord trauma, e.g., spinal cord compression.

G.3 Method G, G.1, or G.2 further comprising a treatment selected from one or more of the following: optimal head and neck positioning to facilitate venous outflow, e.g. head elevation 300; avoidance of dehydration; systemic hypotension; maintenance of normothermia or hypothermia; aggressive measures; osmotherapy, e.g., using mannitol or hypertonic saline; hyperventilation; therapeutic pressor therapy to enhance cerebral perfusion; administration of barbiturates to reduce cerebral metabolism ($CMO_2$); hemicraniectomy; administration of aspirin; administration of amantadine; intravenous thrombolysis (e.g. using rtPA); mechanical clot removal; angioplasty; and/or stents.

G.4 Method G.2 wherein the patient is at elevated risk of cerebral edema, e.g., due to head trauma, ischemic stroke, glioma, meningitis, acute mountain sickness, epileptic seizure, infection, metabolic disorder, water intoxication, hepatic failure, hepatic encephalopathy, or diabetic ketoacidosis.

G.5 Method G.2 wherein the patient has suffered a stroke, head injury, or spinal injury.

G.6 Method G.5 wherein the patient has suffered a stroke, head injury or spinal injury within 12 hours, e.g. within 6 hours, preferably within 3 hours of commencing treatment.

G.7 Method G.2 wherein the patient is at elevated risk of suffering a stroke, head injury or spinal injury, e.g., in combat or in an athletic competition.

G.8 Method G or G.1-G.7 wherein the patient already has cerebral edema.

G.9 Method G or G.1-G.8 wherein the condition to be treated or controlled is cerebral edema consequent to a stroke or a traumatic brain injury.

G.10 Method G or G.1-G.9 wherein the condition to be treated or controlled is cerebral edema consequent to a middle cerebral artery stroke.

G.11 Method G or G.1-G.9 wherein the condition to be treated or controlled is cerebral edema consequent to closed head trauma.

G.12 Method G or G.1-G.4 wherein the condition to be treated or controlled is cerebral edema consequent to an epileptic seizure.

G.13 Method G or G.1-G.4 wherein the condition to be treated or controlled is cerebral edema consequent to an infection.

G.14 Method G or G.1-G.4 wherein the condition to be treated or controlled is cerebral edema consequent to a metabolic disorder.

G.15 Method G or G.1-G.4 wherein the condition to be treated or controlled is cerebral edema consequent to glioma.

G.16 Method G or G.1-G.4 wherein the condition to be treated or controlled is cerebral edema consequent to meningitis.

G.17 Method G or G.1-G.4 wherein the condition to be treated or controlled is cerebral edema consequent to acute mountain sickness.

G.18 Method G or G.1-G.4 wherein the condition to be treated or controlled is cerebral edema consequent to water intoxication.

G.19 Method G or G.1-G.4 wherein the condition to be treated or controlled is cerebral edema consequent to hepatic failure, hepatic encephalopathy, or diabetic ketoacidosis.

G.20 Method G or G.1-G.3 wherein the condition to be treated or controlled is cerebral edema consequent to an abscess.

G.21 Method G or G.1-G.3 wherein the condition to be treated or controlled is cerebral edema consequent to eclampsia.

G.22 Method G or G.1-G.3 wherein the condition to be treated or controlled is cerebral edema consequent to Creutzfeldt-Jakob disease.

G.23 Method G or G.1-G.3 wherein the condition to be treated or controlled is cerebral edema consequent to lupus cerebritis.

G.24 Method G or G.1-G.3 wherein the condition to be treated or controlled is edema consequent to hypoxia, e.g., general systemic hypoxia, e.g., hypoxia caused by an interruption of blood perfusion, for example wherein the edema is cerebral edema consequent to hypoxia caused by cardiac arrest, stroke, or other interruption of blood perfusion to the brain, or wherein the edema is cardiac edema consequent to cardiac ischemia or other interruption of blood flow to the heart.

G.25 Method G or G.1-G.3 wherein the condition to be treated or controlled is cerebral edema consequent to microgravity and/or radiation exposure, e.g., exposure from space flight or from working with radioactive materials or from working in radioactive areas.

G.26 Method G or G.1-G.3 wherein the condition to be treated or controlled is cerebral edema consequent to an invasive central nervous system procedure, e.g., neurosurgery, endovascular clot removal, spinal tap, aneurysm repair, or deep brain stimulation.

G.27 Method G.25 or G.26 wherein the patient is at elevated risk of edema, e.g., due to microgravity and/or radiation exposure, neurosurgery, endovascular clot removal, spinal tap, aneurysm repair, or deep brain stimulation.

G.28 Method G.25 or G.26 wherein the patient already has edema.

G.29 Method G or G.1-G.28 wherein the edema is cytotoxic cerebral edema or is primarily cytotoxic cerebral edema.

G.30 Method G, G.1-G.19, or G.24 wherein the edema is cytotoxic cerebral edema or is primarily cytotoxic cerebral edema.

G.31 Method G, G.1, or G.2 wherein the condition to be treated or controlled is spinal cord edema, e.g., spinal cord edema consequent to a spinal cord trauma, e.g., spinal cord compression.

G.32 Method G.31 wherein the condition to be treated or controlled is spinal cord edema consequent to spinal cord compression.

G.33 Method G, G.1, or G.2 wherein the condition to be treated or controlled is optic nerve edema, e.g., optic nerve edema consequent to microgravity and/or radiation exposure, e.g., exposure from space flight or from working with radioactive materials or from working in radioactive areas.

G.34 Method G, G.1, or G.2 wherein the condition to be treated or controlled is retinal edema.

G.35 Method G, G.1, or G.2 wherein the condition to be treated or controlled is pulmonary edema.

G.36 Method G or G.1 wherein the condition to be treated or controlled is epilepsy.

G.37 Method G or G.1 wherein the condition to be treated or controlled is retinal ischemia or other diseases of the eye associated with abnormalities in intraocular pressure and/or tissue hydration.

G.38 Method G or G.1 wherein the condition to be treated or controlled is myocardial ischemia.

G.39 Method G or G.1 wherein the condition to be treated or controlled is myocardial ischemia/reperfusion injury.

G.40 Method G or G.1 wherein the condition to be treated or controlled is myocardial infarction.

G.41 Method G or G.1 wherein the condition to be treated or controlled is myocardial hypoxia.

G.42 Method G or G.1 wherein the condition to be treated or controlled is congestive heart failure.

G.43 Method G or G.1 wherein the condition to be treated or controlled is sepsis.

G.44 Method G or G.1 wherein the condition to be treated or controlled is a migraine.

G.45 Method G or G.1 wherein the condition to be treated or controlled is neuromyelitis optica.

G.46 Method G or G.1 wherein the condition to be treated or controlled is glioblastoma.

G.47 Method G or G.1 wherein the condition to be treated or controlled is fibromyalgia.

G.48 Method G or G.1 wherein the condition to be treated or controlled is multiple sclerosis.

G.49 Method G wherein the aquaporin is AQP2.

G.50 Method G or G.49 wherein the condition to be treated or controlled is hyponatremia or excessive fluid retention, e.g., consequent to heart failure (HF), for example congestive heart failure, liver cirrhosis, nephrotic disorder, syndrome of inappropriate antidiuretic hormone secretion (SIADH), or infertility treatment.

G.51 Method G, G.49, or G.50 wherein the condition to be treated or controlled is ovarian hyperstimulation syndrome.

G.52 Method G, G.49, or G.50 further comprising one or more of restriction of dietary sodium, fluid and/or alcohol; and/or administration of one or more diuretics, vasopressin receptor antagonists, angiotensin converting enzyme (ACE) inhibitors, aldosterone inhibitors, angiotensin receptor blockers (ARBs), beta-adrenergic antagonists (beta-blockers), and/or digoxin.

G.53 Method G or G.1-G.52 wherein the prodrug salt of an inhibitor of the aquaporin, e.g., the compound of Formula I, e.g., the compound of 1.1-1.52, or, e.g., the compound of Formula II, e.g., the compound of 2.1-2.26, is administered orally.

G.54 Method G or G.1-G.52 wherein the prodrug salt of an inhibitor of the aquaporin, e.g., the compound of Formula I, e.g., the compound of 1.1-1.52, or, e.g., the compound of Formula II, e.g., the compound of 2.1-2.26, is administered parenterally.

G.55 Method G.54 wherein the prodrug salt of an inhibitor of the aquaporin, e.g., the compound of Formula I, e.g., the compound of 1.1-1.52, or, e.g., the compound of Formula II, e.g., the compound of 2.1-2.26, is administered by injection, e.g., subcutaneously, intramuscularly, intravenously, or intrathecally, e.g., a bolus injected subcutaneously, intramuscularly, intravenously, or intrathecally.

G.56 Method G.55 wherein the prodrug salt of an inhibitor of the aquaporin, e.g., the compound of Formula I, e.g., the compound of 1.1-1.52, or, e.g., the compound of Formula II, e.g., the compound of 2.1-2.26, is administered intravenously, e.g., IV bolus and/or IV infusion, e.g., IV bolus followed by IV infusion.

G.57 Method G or G.1-G.56 wherein the patient is human.

G.58 Method G or G.1-G.57 wherein the onset of action after administration of the prodrug salt of an inhibitor of the aquaporin, e.g., the compound of Formula 1, e.g., the compound of 1.1-1.52, or, e.g., the compound of Formula II, e.g., the compound of 2.1-2.26, is fairly rapid.

In yet another embodiment, provided is a compound of Formula I, e.g., a compound of 1.1-1.52, or, e.g., a compound of Formula II, e.g., a compound of 2.1-2.26, for use in treating or controlling a disease or condition mediated by an aquaporin.

In yet another embodiment, provided is a compound of Formula I, e.g., a compound of 1.1-1.52, or, e.g., a compound of Formula II, e.g., a compound of 2.1-2.26, for use in any of Methods A, e.g., A.1-A.58, any of Methods B, e.g., B.1-B.41, any of Methods C, e.g., C.1-C.8, any of Methods D, e.g., D.1-D.19, any of Methods E, e.g., E.1-E.59, any of Methods F, e.g., F.1-F.5, and any of Methods G, e.g., G.1-G.58.

In yet another embodiment, provided is a compound of Formula I, e.g., a compound of 1.1-1.52, or, e.g., a compound of Formula II, e.g., a compound of 2.1-2.26, in the manufacture of a medicament for treating or controlling a disease or condition mediated by an aquaporin.

In yet another embodiment, provided is a compound of Formula I, e.g., a compound of 1.1-1.52, or, e.g., a compound of Formula II, e.g., a compound of 2.1-2.26, in the manufacture of a medicament for use in any of Methods A, e.g., A.1-A.58, any of Methods B, e.g., B.1-B.41, any of Methods C, e.g., C.1-C.8, any of Methods D, e.g., D.1-D.19, any of Methods E, e.g., E.1-E.59, any of Methods F, e.g., F.1-F.5, and any of Methods G, e.g., G.1-G.58.

In yet another embodiment, provided is a pharmaceutical composition comprising a compound of Formula I, e.g., a compound of 1.1-1.52, or, e.g., a compound of Formula II, e.g., a compound of 2.1-2.26, in combination with a pharmaceutically acceptable excipient for use in treating or controlling a disease or condition mediated by an aquaporin.

In yet another embodiment, provided is a pharmaceutical composition comprising a compound of Formula I, e.g., a compound of 1.1-1.52, or, e.g., a compound of Formula II, e.g., a compound of 2.1-2.26, in combination with a pharmaceutically acceptable excipient for use in any of Methods A, e.g., A.1-A.58, any of Methods B, e.g., B.1-B.41, any of Methods C, e.g., C.1-C.8, any of Methods D, e.g., D.1-D.19, any of Methods E, e.g., E.1-E.59, any of Methods F, e.g., F.1-F.5, and any of Methods G, e.g., G.1-G.58.

Compounds of Formula I, e.g., compounds of 1.1-1.52, or, e.g., compounds of Formula II, e.g., compounds of 2.1-2.26, as hereinbefore described for use in the methods of the invention may be used as a sole therapeutic agent, but may also be used in combination or for co-administration with other active agents, for example in conjunction with conventional therapies for cerebral edema, stroke, traumatic brain injury, glioma (e.g., glioblastoma), meningitis, acute mountain sickness, infection, metabolic disorder, hypoxia, water intoxication, hepatic failure, hepatic encephalopathy, diabetic ketoacidosis, abscess, eclampsia, Creutzfeldt-Jakob disease, lupus cerebritis, optic nerve edema, hyponatremia, fluid retention, ovarian hyperstimulation syndrome, epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or migraines.

A dose or method of administration of the dose of the present disclosure is not particularly limited. Dosages employed in practicing the present disclosure will of course vary depending, e.g. on the particular disease or condition to be treated, the particular compound used, the mode of administration, and the therapy desired. The compounds may be administered by any suitable route, including orally, parenterally, transdermally, or by inhalation. In stroke or other severely debilitating diseases or conditions, for example where the patient may be unconscious or unable to swallow, an IV infusion and/or IV bolus may be preferred. In general, satisfactory results, e.g. for the treatment of diseases as hereinbefore set forth are indicated to be obtained on oral administration at dosages of the order from about 0.01 to 15.0 mg/kg. In larger mammals, for example humans, an indicated daily dosage for oral administration will accordingly be in the range of from about 0.75 to 1000 mg per day, conveniently administered once, or in divided doses 2 to 3 times, daily or in sustained release form. Unit dosage forms for oral administration thus for example may comprise from about 0.2 to 75 or 150 mg, e.g. from about 0.2 or 2.0 mg to 50, 75, 100, 125, 150 or 200 mg of a compound of Formula T, e.g., a compound of 1.1-1.52, or, e.g., a compound of Formula II, e.g., a compound of 2.1-2.26, together with a pharmaceutically acceptable diluent or carrier therefor. When the medicament is used via injection (subcutaneously, intramuscularly or intravenously) the dose may be 0.1 or 0.25 mg to 500 mg per day, e.g., from about 0.25 to 75 or 150 mg, e.g., from about 0.1 or 0.25 or 2.0 mg to 50, 75, 100, 125, 150, 200, 300, 400, or 500 mg, by bolus or if IV by bolus or infusion.

In yet another embodiment, provided is a pharmaceutical composition (Composition I) comprising a compound of Formula I, e.g., a compound of 1.1-1.52, or, e.g., a compound of Formula II, e.g., a compound of 2.1-2.26, and a pharmaceutically acceptable excipient.

Further provided is Composition I as follows:

1.1 Composition I wherein the composition comprises 0.1 or 0.25 mg to 2.0 g of the compound of Formula I, e.g., the compound of 1.1-1.52, or, e.g., the compound of Formula II, e.g., the compound of 2.1-2.26, e.g., from about 0.1 or 0.25 mg to 75 mg or 600 mg, e.g., from about 0.1 or 0.25 or 1 or 2 mg or 5 or 10 or 15 or 20 to 50, 75, 100, 125, 150, 200, 300, 400, 500, or 600 mg, or 1 g, 1.5 g, or 2.0 g, e.g., from about 5 to 50, 75, 100, 125, 150, 200, 300, 400, 500, or 600 mg, or 1 g, 1.5 g, or 2 g, e.g., from about 5 to 500 mg, e.g., from about 5 to 300 mg, e.g., from about 5 to 200 mg, e.g., from about 25 to 500 mg, e.g., from about 25 to 300 mg, e.g., from about 25 to 200 mg, e.g., from about 0.5 or 1 mg to 50 mg, e.g., from about 0.5 or 1 mg to 20 mg, e.g., from about 0.5 or 1 mg to 10 mg, e.g., from about 1 or 2 or 5 mg to 10 or 20 mg, e.g., from about 1 or 2 or 3 or 4 to 5 mg or wherein the composition comprises the compound of Formula I, e.g., the compound of 1.1-1.52, or, e.g., the compound of Formula II, e.g., the compound of 2.1-2.26 in an amount sufficient to provide 0.1 or 0.25 mg to 2.0 g of N-[3,5-bis(trifluoromethyl)phenyl]-5-chloro-2-hydroxybenzamide, e.g., from about 0.1 or 0.25 mg to 75 or 600 mg, e.g., from about 0.1 or 0.25 or 1 or 2 or 5 or 10 or 15 or 20 mg to 50, 75, 100, 125, 150, 200, 300, 400, 500, or 600 mg, or 1 g, 1.5 g, or 2.0 g, e.g., from about 5 to 50, 75, 100, 125, 150, 200, 300, 400, 500, or 600 mg, or 1 g, 1.5 g, or 2 g, e.g., from about 5 to 500 mg, e.g., from about 5 to 300 mg, e.g., from about 5 to 200 mg, e.g., from about 25 to 500 mg, e.g., from about 25 to 300 mg, e.g., from about 25 to 200 mg, e.g., from about 0.5 or 1 mg to 50 mg, e.g., from about 0.5 or 1 mg to 20 mg, e.g., from about 0.5 or 1 mg to 10 mg, e.g., from about 1 or 2 or 5 mg to 10 or 20 mg, e.g., from about 1 or 2 or 3 or 4 to 5 mg.

1.2 Composition I wherein the composition comprises 2-{[3,5-bis(trifluoromethyl)phenyl]carbamoyl}-4-chlorophenyl dihydrogen phosphate in an amount sufficient to provide a dose of 0.01 or 0.1 or 0.5 mg/kg to 1 or 5 or 10 or 15 mg/kg of N-[3,5-bis(trifluoromethyl)phenyl]-5-chloro-2-hydroxybenzamide, e.g., a dose of about 0.05 to 1 or 5 mg/kg, e.g., a dose of about 0.05 to 0.1, 0.2, 0.3, 0.4, 0.5, 1, 5, 10 or 20 mg/kg, e.g., a dose of about 0.5 to 1, 2, 3, 4, 5 or 10 or 20 mg/kg, e.g., a dose of about 1 to 2, 3, 4, 5, 10, 20 or 50 mg/kg.

1.3 Composition I, 1.1, or 1.2 wherein the pharmaceutically acceptable excipient comprises one or more buffering agents which may control pH, e.g., one or more of sodium citrate, potassium citrate, sodium phosphate (e.g., $NaH_2PO_4$ and/or $Na_2HPO_4$), potassium phosphate (e.g., $KH_2PO_4$ and/or $K_2HPO_4$), tris(hydroxymethyl)aminomethane (also known as tris base), tris(hydroxymethyl)aminomethane acetate (also known as tris acetate), zinc chloride, meglumine, sodium acetate, potassium acetate, sodium hydroxide, and arginine, e.g., one or more of sodium citrate, $Na_2HPO_4$, tris(hydroxymethyl)aminomethane, tris(hydroxymethyl) aminomethane acetate e.g., $Na_2HPO_4$, e.g., tris(hydroxymethyl)aminomethane, e.g., tris(hydroxymethyl) aminomethane acetate.

1.4 Composition I or 1.1-1.3 wherein the composition comprises 1 or 5 mg to 200 or 500 mg of one or more buffering agents, e.g., from about 1 or 5 or 10 mg to 50, 100, 150, 200, 250, 300, 350, 400, 450, or 500 mg.

1.5 Composition I or 1.1-1.4 wherein the composition comprises one or more of sodium citrate and sodium phosphate, e.g., $Na_2HPO_4$.

1.6 Composition I or 1.1-1.5 wherein the composition comprises sodium citrate.

1.7 Composition 1.6 wherein the composition comprises 1 or 5 mg to 200 or 500 mg sodium citrate, e.g., from about 1 or 5 or 10 mg to 50, 100, 150, 200, 250, 300, 350, 400, 450, or 500 mg sodium citrate.

1.8 Composition I or 1.1-1.7 wherein the composition comprises sodium phosphate, e.g., Na$_2$HPO$_4$.

1.9 Composition 1.8 wherein the composition comprises 1 or 5 mg to 200 or 500 mg sodium phosphate, e.g., from about 1 or 5 or 10 mg to 50, 100, 150, 200, 250, 300, 350, 400, 450, or 500 mg sodium phosphate, e.g., Na$_2$HPO$_4$.

1.10 Composition I or 1.1-1.9 wherein the composition comprises Na$_2$HPO$_4$.

1.11 Composition 1.10 wherein the composition comprises 1 or 5 mg to 200 mg or 500 mg Na$_2$HPO$_4$, e.g., from about 1 or 5 or 10 mg to 50, 100, 150, 200, 250, 300, 350, 400, 450, or 500 mg Na$_2$HPO$_4$.

1.12 Composition I or 1.1-1.11 wherein the composition comprises one or more bulking agents which may provide an adequate structure to the lyophilized cake, e.g., one or more of mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40).

1.13 Composition I or 1.1-1.12 wherein the composition comprises 5 or 10 or 50 mg to 2 or 5 g of one or more bulking agents, e.g., from about 50 or 100 mg to 200, 300, 500, or 800 mg, or 1, 1.5, 2, 3, 4, or 5 g of one or more bulking agents.

1.14 Composition I or 1.1-1.13 wherein the composition comprises dextran (e.g., dextran 40).

1.15 Composition 1.14 wherein the composition comprises 5 or 10 or 50 mg to 2 or 5 g dextran (e.g., dextran 40), e.g., from about 50 or 100 mg to 200, 300, 500, or 800 mg, or 1, 1.5, 2, 3, 4, or 5 g dextran (e.g., dextran 40).

1.16 Composition I or 1.1-1.15 wherein the composition comprises one or more solubilizing agents, e.g., ethylenediamine tetraacetic acid (EDTA) or a salt thereof (e.g., calcium disodium EDTA, disodium EDTA, sodium EDTA), alpha cyclodextrin, hydroxypropyl-β-cyclodextrin, polysorbate 80, tert-butanol, isopropanol, dichloromethane, ethanol, acetone, and glycerol; one or more collapse temperature modifiers which may shift the overall collapse temperature higher, e.g., one or more of dextran, Ficoll®, gelatin, and hydroxyethyl starch; one or more tonicity modifiers, e.g., one or more of sodium chloride, potassium chloride, sucrose, mannitol, glucose, and lactose; and one or more antimicrobial agents, e.g., one or more of benzyl alcohol, phenol, 2-phenoxyethanol, m-cresol, chlorobutanol, parabens (e.g., methyl paraben, ethyl paraben, propyl paraben), benzalkonium chloride, benzethonium chloride, myristyl gamma-picolinium salt (e.g., myristyl gamma-picolinium chloride), and organomercury compounds and salts (e.g., phenyl mercuric acetate, phenyl mercuric borate, phenyl mercuric nitrate, and thimerosal).

1.17 Composition I or 1.1-1.16 wherein the composition is a solid.

1.18 Composition I or 1.1-1.17 wherein the composition is lyophilized.

1.19 Composition I or 1.1-1.18 wherein the compound of Formula I, e.g., the compound of 1.1-1.52, or, e.g., the compound of Formula II, e.g., the compound of 2.1-2.26, is lyophilized, e.g., by freezing, primary drying, and secondary drying.

1.20 Composition 1.19 wherein the compound of Formula 1, e.g., the compound of 1.1-1.52, or, e.g., the compound of Formula II, e.g., the compound of 2.1-2.26, is lyophilized, e.g., by freezing, primary drying, and secondary drying, prior to admixture with the pharmaceutically acceptable excipient.

1.21 Composition I or 1.1-1.20 wherein the compound of Formula I, e.g., the compound of 1.1-1.52, or, e.g., the compound of Formula II, e.g., the compound of 2.1-2.26, is crystalline.

1.22 Composition I or 1.1-1.20 wherein the compound of Formula I, e.g., the compound of 1.1-1.52, or, e.g., the compound of Formula II, e.g., the compound of 2.1-2.26, is amorphous.

1.23 Composition I or 1.1-1.22 which is suitable for constitution, or reconstitution if lyophilized, with a solvent into a pharmaceutically acceptable liquid (e.g., a solution or suspension, e.g., a solution).

1.24 Composition I or 1.1-1.23 wherein the composition is admixed with a solvent, e.g., a sterile solution, e.g., sterile water for injection, a sterile solution comprising dextrose (e.g., dextrose injection 5%), a sterile solution comprising sodium chloride (e.g., 0.9% sodium chloride injection), a sterile solution comprising benzyl alcohol (e.g., bacteriostatic water for injection with benzyl alcohol or bacteriostatic sodium chloride for injection with benzyl alcohol), or Lactated Ringer's.

1.25 Composition I or 1.1-1.24 wherein the composition is admixed with 0.5 to 500 mL solvent, e.g., from about 1 or 2 mL to 500 mL, e.g., from about 1 or 2 mL to 5, 10, 25, 50, 75, 100, 150, 200, 300 or 500 mL, e.g., from about 1 or 2 mL to 5, 10, 25, 50, 75, 100, or 200 mL, e.g., from about 5 to 10, 25, 50, or 100 mL.

1.26 Composition I or 1.1-1.25 wherein the composition is admixed with 0.5 to 500 mL sterile solution, e.g., sterile water for injection, a sterile solution comprising dextrose (e.g., dextrose injection 5%), a sterile solution comprising sodium chloride (e.g., 0.9% sodium chloride injection), a sterile solution comprising benzyl alcohol (e.g., bacteriostatic water for injection with benzyl alcohol or bacteriostatic sodium chloride for injection with benzyl alcohol), or Lactated Ringer's, e.g., from about 1 or 2 mL to 500 mL, e.g., from about 1 or 2 mL to 5, 10, 25, 50, 75, 100, 150, 200, 300 or 500 mL, e.g., from about 1 or 2 mL to 5, 10, 25, 50, 75, 100, or 200 mL, e.g., from about 5 to 10, 25, 50, or 100 mL.

1.27 Composition I or 1.1-1.26 wherein the composition is admixed with sterile water for injection or a sterile solution comprising sodium chloride (e.g., 0.9% sodium chloride injection).

1.28 Composition I or 1.1-1.27 wherein the composition is admixed with sterile water for injection.

1.29 Composition 1.28 wherein the composition is admixed with 0.5 to 500 mL sterile water for injection, e.g., from about 1 or 2 mL to 500 mL, e.g., from about 1 or 2 mL to 5, 10, 25, 50, 75, 100, 150, 200, 300 or 500 mL, e.g., from about 1 or 2 to 5, 10, 25, 50, 75, 100, or 200 mL, e.g., from about 5 to 10, 25, 50, or 100 mL.

1.30 Composition I or 1.1-1.29 wherein the composition is admixed with a sterile solution comprising sodium chloride (e.g., 0.9% sodium chloride injection).

1.31 Composition 1.30 wherein the composition is admixed with 0.5 to 500 mL a sterile solution comprising sodium chloride (e.g., 0.9% sodium chloride injection), e.g., from about 1 of 2 mL to 500 mL, e.g., from about 1 or 2 mL to 5, 10, 25, 50, 75, 100, 150, 200, 300 or 500 mL, e.g., from about 1 or 2 to 5, 10, 25, 50, 75, 100, or 200 mL, e.g., from about 5 to 10, 25, 50, or 100 mL.
1.32 Composition 1.24-1.31 wherein the solvent, e.g., the sterile solution, comprises a buffering agent, e.g., one or more of sodium citrate, potassium citrate, sodium phosphate (e.g., $NaH_2PO_4$ and/or $Na_2HPO_4$), potassium phosphate (e.g., $KH_2PO_4$ and/or $K_2HPO_4$), tris base (also known as tris(hydroxymethyl)aminomethane), tris acetate (also known as tris(hydroxymethyl) aminomethane acetate), zinc chloride, meglumine, sodium acetate, potassium acetate, sodium hydroxide, and arginine, e.g., one or more of sodium citrate and $Na_2HPO_4$, e.g., $Na_2HPO_4$.
1.33 Composition 1.32 wherein the solvent, e.g., the sterile solution, comprises 1 or 5 mg to 200 or 500 mg of one or more buffering agents, e.g., from about 1 or 5 or 10 mg to 50, 100, 150, 200, 250, 300, 350, 400, 450, or 500 mg.
1.34 Composition 1.32 or 1.33 wherein the solvent, e.g. the sterile solution, comprises one or more of sodium citrate and sodium phosphate, e.g., $Na_2HPO_4$.
1.35 Composition 1.32-1.34 wherein the solvent, e.g. the sterile solution comprises sodium citrate.
1.36 Composition 1.35 wherein the solvent, e.g., the sterile solution, comprises 1 or 5 mg to 200 or 500 mg sodium citrate, e.g., from about 1 or 5 or 10 mg to 50, 100, 150, 200, 250, 300, 350, 400, 450, or 500 mg sodium citrate.
1.37 Composition 1.31-1.36 wherein the solvent, e.g., the sterile solution, comprises sodium phosphate, e.g., $Na_2HPO_4$.
1.38 Composition 1.37 wherein the solvent, e.g., the sterile solution, comprises 1 or 5 mg to 200 mg or 500 mg sodium phosphate, e.g., from about 1 or 5 or 10 mg to 50, 100, 150, 200, 250, 300, 350, 400, 450, or 500 mg sodium phosphate, e.g., $Na_2HPO_4$.
1.39 Composition 1.24-1.38 wherein the solvent, e.g., the sterile solution comprises one or more bulking agents, e.g., one or more of maltose, mannose, ribose, cyclodextrin, mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40).
1.40 Composition 1.24-1.39 wherein the solvent, e.g., the sterile solution, comprises 5 or 10 or 50 mg to 2 or 5 g of one or more bulking agents, e.g., from about 50 or 100 mg to 200, 300, 500, or 800 mg, or 1, 1.5, 2, 3, 4, or 5 g of one or more bulking agents.
1.41 Composition 1.24-1.40 wherein the solvent, e.g., the sterile solution, comprises dextran (e.g., dextran 40).
1.42 Composition 1.41 wherein the solvent, e.g. the sterile solution, comprises 5 or 10 or 50 mg to 2 or 5 g dextran (e.g., dextran 40), e.g., from about 50 or 100 mg to 200, 300, 500, or 800 mg, or 1, 1.5, 2, 3, 4, or 5 dextran (e.g., dextran 40).
1.43 Composition 1.24-1.42 wherein the solvent, e.g., the sterile solution, comprises one or more solubilizing agents, e.g., ethylenediamine tetraacetic acid (EDTA) or a salt thereof (e.g., calcium disodium EDTA, disodium EDTA, sodium EDTA), alpha cyclodextrin, hydroxypropyl-β-cyclodextrin, polysorbate 80, tert-butanol, isopropanol, dichloromethane, ethanol, acetone, and glycerol; one or more collapse temperature modifiers which may shift the overall collapse temperature higher, e.g., one or more of dextran, Ficoll®, gelatin, and hydroxyethyl starch; one or more tonicity modifiers, e.g., one or more of sodium chloride, potassium chloride, sucrose, mannitol, and glucose; and one or more antimicrobial agents, e.g., one or more of benzyl alcohol, phenol, 2-phenoxyethanol, m-cresol, chlorobutanol, parabens (e.g., methyl paraben, ethyl paraben, propyl paraben), benzalkonium chloride, benzethonium chloride, myristyl gamma-picolinium salt (e.g., myristyl gamma-picolinium chloride), and organomercury compounds and salts (e.g., phenyl mercuric acetate, phenyl mercuric borate, phenyl mercuric nitrate, and thimerosal).
1.44 Composition 1.24-1.43 wherein the pH is between pH 7 and pH 10.5, e.g., between pH 7 and pH 9.5, e.g., between pH 7 and pH 8.
1.45 Composition 1.24-1.44 wherein the composition is filtered to remove particles and microbes, e.g., filtered prior to injection.
1.46 Composition 1.24-1.45 wherein the compositions is administered about 24 hours, 12 hours, 10 hours, 8 hours, 2 hours, 1 hour, 30 minutes, 20 minutes, 15 minutes, 10 minutes, 5 minutes, 3 minutes, 2 minutes or 1 minute or less after admixture.
1.47 Composition I or 1.1-1.46 wherein the composition is for injection, e.g., subcutaneously, intramuscularly, intravenously, or intrathecally, e.g., intramuscularly or intravenously, e.g., a bolus injected subcutaneously, intramuscularly, intravenously, or intrathecally.
1.48 Composition 1.47 wherein the composition is for injection intravenously, e.g., IV bolus and/or IV infusion, e.g., IV bolus followed by IV infusion.
1.49 Composition 1.47 wherein the composition is for injection intramuscularly, e.g., IM bolus and/or IM infusion, e.g., IM bolus followed by IM infusion.
1.50 Composition 1.48 or 1.49 wherein the infusion, e.g., IV or IM, is administered over about 10 or 30 minutes to 72 hours, e.g., about 30 minutes to 24 hours, e.g., about 30 minutes to 12 hours, e.g., about 30 minutes to 8 hours, e.g., about 30 minutes to 6 hours, e.g., about 30 minutes to 4 hours, e.g., about 30 minutes to 2 hours, e.g., about 30 minutes to 1 hour, e.g., about 72 hours.
1.51 Composition I wherein the composition is formulated for oral administration.
1.52 Composition 1.51 wherein the composition is a tablet, capsule, solution, suspension, or the like.
1.53 Composition I or 1.1-1.52 wherein the composition comprises one or more additional therapeutic agents, e.g., one or more additional therapeutic agents for cerebral edema, stroke, traumatic brain injury, glioma (e.g., glioblastoma), meningitis, acute mountain sickness, infection, metabolic disorder, hypoxia, water intoxication, hepatic failure, hepatic encephalopathy, diabetic ketoacidosis, abscess, eclampsia, Creutzfeldt-Jakob disease, lupus cerebritis, optic nerve edema, hyponatremia, fluid retention, ovarian hyperstimulation syndrome, epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or migraines.
1.54 Composition I or 1.1-1.53 wherein the composition comprises one or more additional therapeutic agents, e.g., one or more additional therapeutic agents for pulmonary edema, fibromyalgia, or multiple sclerosis.

1.55 Composition I or 1.1-1.54 wherein the composition is administered concurrently or sequentially, in either order, with one or more additional therapeutic agents, e.g., one or more additional therapeutic agents for cerebral edema, stroke, traumatic brain injury, glioma (e.g., glioblastoma), meningitis, acute mountain sickness, infection, metabolic disorder, hypoxia, water intoxication, hepatic failure, hepatic encephalopathy, diabetic ketoacidosis, abscess, eclampsia, Creutzfeldt-Jakob disease, lupus cerebritis, optic nerve edema, hyponatremia, fluid retention, ovarian hyperstimulation syndrome, epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or migraines.

1.56 Composition I or 1.1-1.55 wherein the composition is administered concurrently or sequentially, in either order, with one or more additional therapeutic agents, e.g., one or more additional therapeutic agents for pulmonary edema, fibromyalgia, or multiple sclerosis.

1.57 Composition I or 1.1-1.57 wherein the composition for use in any of the methods described herein, e.g., for use in Method A, e.g., Method A.1-A.58, for use in Method B, e.g., Method B.1-B.41, e.g., for use in Method C, e.g., C.1-C.8, e.g., for use in Method D, e.g., D.1-D.19, e.g., for use in Method E, e.g., E.1-E.59, e.g., for use in Method F, e.g., F.1-F.5, e.g., for use in Method G, e.g., G.1-G.58.

In some embodiments, when the compound of Formula I, e.g., the compound of 1.1-1.52, or, e.g., the compound of Formula II, e.g., the compound of 2.1-2.26, is provided as a solid that is to be admixed with a solvent, e.g., a sterile solution, to provide a pharmaceutically acceptable liquid, it is typically provided as a powder and admixed immediately or shortly before administration to the patient. In some embodiments, the powdered compound of Formula I, e.g., the compound of 1.1-1.52, or, e.g., the compound of Formula II, e.g., the compound of 2.1-2.26, may be packaged in a container, for example, in a vial to which is added the solvent. Alternatively, the contents of the vial may be added to the solvent in a separate container. In some embodiments, the powdered compound of Formula I, e.g., the compound of 1.1-1.52, or, e.g., the compound of Formula II, e.g., the compound of 2.1-2.26, is packaged in a sachet, such as a foil package, that can be opened and the contents added to the solvent. In some embodiments, the powdered compound of Formula I, e.g., the compound of 1.1-1.52, or, e.g., the compound of Formula II, e.g., the compound of 2.1-2.26, is formulated as a tablet that dissolves when it is added to the solvent.

In yet another embodiment, a pharmaceutical composition comprising a compound of Formula I, e.g., a compound of 1.1-1.52, or, e.g., a compound of Formula II, e.g., a compound of 2.1-2.26, e.g., Composition I, e.g., composition 1.1-1.52, is prepared by admixing the compound of Formula I, e.g., the compound of 1.1-1.52, or, e.g., the compound of Formula II, e.g., the compound of 2.1-2.26, with a pharmaceutically acceptable excipient. In some embodiments, the compound of Formula 1, e.g., the compound of 1.1-1.52, or, e.g., the compound of Formula II, e.g., the compound of 2.1-2.26, is crystalline. In some embodiments, the compound of Formula I, e.g., the compound of 1.1-1.52, or, e.g., the compound of Formula II, e.g., the compound of 2.1-2.26, is amorphous. In some embodiments, the compound of Formula I, e.g., the compound of 1.1-1.52, or, e.g., the compound of Formula II, e.g., the compound of 2.1-2.26, is lyophilized. In some embodiments, the compound of Formula I, e.g., the compound of 1.1-1.52, or, e.g., the compound of Formula II, e.g., the compound of 2.1-2.26, and the pharmaceutically acceptable excipient, e.g., Composition I, e.g., composition 1.1-1.57, is lyophilized.

In yet another embodiment, a pharmaceutical composition comprising a compound of Formula I, e.g., a compound of 1.1-1.52, or, e.g., a compound of Formula II, e.g., a compound of 2.1-2.26, e.g., Composition I, e.g., composition 1.1-1.57, is prepared by admixing the compound of Formula I, e.g., the compound of 1.1-1.52, or, e.g., the compound of Formula II, e.g., the compound of 2.1-2.26, with a sterile solution, e.g., sterile water for injection or a sterile solution comprising sodium chloride (e.g., 0.9% sodium chloride injection), to form a pharmaceutically acceptable liquid. In some embodiments, the compound of Formula I, e.g., the compound of 1.1-1.52, or, e.g., the compound of Formula II, e.g., the compound of 2.1-2.26, is admixed with the sterile solution immediately or shortly before administration. In some embodiments, the compound of Formula I, e.g., the compound of 1.1-1.52, or, e.g., the compound of Formula II, e.g., the compound of 2.1-2.26, is admixed with a buffering agent, e.g., sodium citrate and/or sodium phosphate (e.g., $Na_2HPO_4$), prior to admixture with the sterile solution, e.g., sterile water for injection or a sterile solution comprising sodium chloride (e.g., 0.9% sodium chloride injection). In some embodiments, the compound of Formula I, e.g., the compound of 1.1-1.52, or, e.g., the compound of Formula II, e.g., the compound of 2.1-2.26, is admixed with a buffering agent, e.g., sodium citrate and/or sodium phosphate (e.g., $Na_2HPO_4$), and/or a bulking agent, e.g., dextran (e.g., dextran 40), prior to admixture with the sterile solution, e.g., sterile water for injection or a sterile solution comprising sodium chloride (e.g., 0.9% sodium chloride injection). In some embodiments, the compound of Formula I, e.g., the compound of 1.1-1.52, or, e.g., the compound of Formula II, e.g., the compound of 2.1-2.26, admixed with the buffering agent and/or the bulking agent is lyophilized. In some embodiments, the compound of Formula I, e.g., the compound of 1.1-1.52, or, e.g., the compound of Formula II, e.g., the compound of 2.1-2.26, is admixed with a sterile solution comprising a buffering agent, e.g., sodium citrate and/or sodium phosphate (e.g., $Na_2HPO_4$). In some embodiments, the compound of Formula I, e.g., the compound of 1.1-1.52, or, e.g., the compound of Formula II, e.g., the compound of 2.1-2.26, is admixed with a sterile solution comprising a buffering agent, e.g., sodium citrate and/or sodium phosphate (e.g., $Na_2HPO_4$) and/or a bulking agent. In some embodiments, the admixture of the compound of Formula I, e.g., the compound of 1.1-1.52, or, e.g., the compound of Formula II, e.g., the compound of 2.1-2.26, and the sterile solution is agitated, e.g., any mode of agitation that results in a clear liquid, e.g., mechanical agitation, sonication, conventional mixing, conventional stirring and the combinations thereof. In some embodiments, the compound of Formula I, e.g., the compound of 1.1-1.52, or, e.g., the compound of Formula II, e.g., the compound of 2.1-2.26, admixed with the sterile solution is lyophilized. In some embodiments, the compound of Formula I, e.g., the compound of 1.1-1.52, or, e.g., the compound of Formula II, e.g., the compound of 2.1-2.26, admixed with the sterile solution is crystalline. In some embodiments, the compound of Formula 1, e.g., the compound of 1.1-1.52, or, e.g., the compound of Formula II, e.g., the compound of 2.1-2.26, admixed with the sterile solution is amorphous.

In one embodiment, Composition I, e.g., composition 1.1-1.57, is prepared by admixing the compound of Formula I, e.g., the compound of 1.1-1.52, or, e.g., the compound of Formula II, e.g., the compound of 2.1-2.26, with a solvent, e.g., a sterile water for injection or a sterile solution comprising sodium chloride (e.g., 0.9% sodium chloride injection). In some embodiments, the compound of Formula I, e.g., the compound of 1.1-1.52, or, e.g., the compound of Formula II, e.g., the compound of 2.1-2.26, is admixed with a buffering agent, e.g., sodium citrate and/or sodium phosphate (e.g., $Na_2HPO_4$), and/or a bulking agent, e.g., dextran (e.g., dextran 40), prior to admixture with the solvent. In some embodiments, the solvent comprises a buffering agent, e.g., sodium citrate and/or sodium phosphate (e.g., $Na_2HPO_4$) and/or a bulking agent, e.g., dextran (e.g., dextran 40). In some embodiments, the admixture of the compound of Formula I, e.g., the compound of 1.1-1.52, or, e.g., the compound of Formula II, e.g., the compound of 2.1-2.26, and the solvent is agitated after admixture, e.g., by any mode of agitation that results in a clear liquid, e.g., mechanical agitation, sonication, conventional mixing, conventional stirring and the combinations thereof. In some embodiments, the compound of Formula 1, e.g., the compound of 1.1-1.52, or, e.g., the compound of Formula II, e.g., the compound of 2.1-2.26, is lyophilized. In some embodiments, the admixture of the compound of Formula I, e.g., the compound of 1.1-1.52, or, e.g., the compound of Formula II, e.g., the compound of 2.1-2.26, and the buffering agent and/or bulking agent is lyophilized. In some embodiments, the compound of Formula I, e.g., the compound of 1.1-1.52, or, e.g., the compound of Formula II, e.g., the compound of 2.1-2.26, is admixed with the solvent, e.g., the sterile solution, immediately or shortly before administration.

Pharmaceutical compositions disclosed herein, e.g., Composition I, e.g., composition 1.1-1.57, may be contained in a sterilized vessel such as syringes, vials or ampoules of various sizes and capacities.

In yet another embodiment, provided is a kit (Kit I) comprising a compound of Formula I, e.g., a compound of 1.1-1.52, or, e.g., a compound of Formula II, e.g., a compound of 2.1-2.26.

Further provided is Kit I as follows:

1.1 Kit I wherein the kit comprises 0.1 or 0.25 mg to 2.0 g of the compound of Formula 1, e.g., the compound of 1.1-1.52, or, e.g., the compound of Formula II, e.g., the compound of 2.1-2.26, e.g., from about 0.1 or 0.25 mg to 75 or 600 mg, e.g., from about 0.1 or 0.25 or 1 or 2 or 5 or 10 or 15 or 20 mg to 50, 75, 100, 125, 150, 200, 300, 400, 500, or 600 mg, or 1, 1.5, or 2.0 g, e.g., from about 5 to 50, 75, 100, 125, 150, 200, 300, 400, 500, or 600 mg, or 1 g, 1.5 g, or 2 g, e.g., from about 5 to 500 mg, e.g., from about 5 to 300 mg, e.g., from about 5 to 200 mg, e.g., from about 25 to 500 mg, e.g., from about 25 to 300 mg, e.g., from about 25 to 200 mg, e.g., from about 0.5 or 1 mg to 50 mg, e.g., from about 0.5 or 1 mg to 20 mg, e.g., from about 0.5 or 1 mg to 10 mg, e.g., from about 1 or 2 or 5 mg to 10 or 20 mg, e.g., from about 1 or 2 or 3 or 4 to 5 mg or wherein the composition comprises the compound of Formula I, e.g., the compound of 1.1-1.52, or, e.g., the compound of Formula II, e.g., the compound of 2.1-2.26 in an amount sufficient to provide 0.1 or 0.25 mg to 2.0 g of N-[3,5-bis(trifluoromethyl)phenyl]-5-chloro-2-hydroxybenzamide, e.g., from about 0.1 or 0.25 mg to 75 or 600 mg, e.g., from about 0.1 or 0.25 or 1 or 2 or 5 or 10 or 15 or 20 mg to 50, 75, 100, 125, 150, 200, 300, 400, 500, or 600 mg, or 1 g, 1.5 g, or 2.0 g, e.g., from about 5 to 50, 75, 100, 125, 150, 200, 300, 400, 500, or 600 mg, or 1 g, 1.5 g, or 2 g, e.g., from about 5 to 500 mg, e.g., from about 5 to 300 mg, e.g., from about 5 to 200 mg, e.g., from about 25 to 500 mg, e.g., from about 25 to 300 mg, e.g., from about 25 to 200 mg, e.g., from about 0.5 or 1 mg to 50 mg, e.g., from about 0.5 or 1 mg to 20 mg, e.g., from about 0.5 or 1 mg to 10 mg, e.g., from about 1 or 2 or 5 mg to 10 or 20 mg, e.g., from about 1 or 2 or 3 or 4 to 5 mg.

1.2 Kit I or 1.1 wherein the kit comprises 2-{[3,5-bis(trifluoromethyl)phenyl]carbamoyl}-4-chlorophenyl dihydrogen phosphate in an amount sufficient to provide a dose of 0.01 or 0.1 or 0.5 mg/kg to 1 or 5 or 10 or 15 mg/kg of N-[3,5-bis(trifluoromethyl)phenyl]-5-chloro-2-hydroxybenzamide, e.g., a dose of about 0.05 to 1 or 5 mg/kg, e.g., a dose of about 0.05 to 0.1, 0.2, 0.3, 0.4, 0.5, 1, 5, 10 or 20 mg/kg, e.g., a dose of about 0.5 to 1, 2, 3, 4, 5 or 10 or 20 mg/kg, e.g., a dose of about 1 to 2, 3, 4, 5, 10, 20 or 50 mg/kg.

1.3 Kit I, 1.1, or 1.2 wherein the kit comprises one or more pharmaceutically acceptable excipients.

1.4 Kit 1.3 wherein the one or more pharmaceutically acceptable excipients are selected from the group consisting of buffering agents, bulking agents, solubilizing agents, collapse temperature modifiers and.

1.5 Kit 1.3 or 1.4 wherein the kit comprises one or more buffering agents which may control pH, e.g., one or more of sodium citrate, potassium citrate, sodium phosphate (e.g., $NaH_2PO_4$ and/or $Na_2HPO_4$), potassium phosphate (e.g., $KH_2PO_4$ and/or $K_2HPO_4$), tris(hydroxymethyl)aminomethane (also known as tris base), tris(hydroxymethyl)aminomethane acetate (also known as tris acetate), zinc chloride, meglumine, sodium acetate, potassium acetate, sodium hydroxide, and arginine, e.g., one or more of sodium citrate, $Na_2HPO_4$, tris(hydroxymethyl)aminomethane, and tris(hydroxymethyl)aminomethane acetate, e.g., $Na_2HPO_4$, e.g., tris(hydroxymethyl)aminomethane, e.g., tris(hydroxymethyl)aminomethane acetate.

1.6 Kit 1.5 wherein the kit comprises 1 or 5 mg to 200 mg or 500 mg of one or more buffering agents, e.g., from about 1 or 5 or 10 mg to 50, 100, 150, 200, 250, 300, 350, 400, 450, or 500 mg.

1.7 Kit 1.5 or 1.6 wherein the kit comprises one or more of sodium citrate and sodium phosphate, e.g., $Na_2HPO_4$.

1.8 Kit 1.3-1.7 wherein the kit comprises sodium citrate.

1.9 Kit 1.8 wherein the kit comprises 1 or 5 mg to 200 or 500 mg sodium citrate, e.g., from about 1 or 5 or 10 mg to 50, 100, 150, 200, 250, 300, 350, 400, 450, or 500 mg sodium citrate.

1.10 Kit 1.3-1.9 wherein the kit comprises sodium phosphate, e.g., $Na_2HPO_4$.

1.11 Kit 1.9 wherein the kit comprises 1 or 5 mg to 200 or 500 mg sodium phosphate, e.g., from about 1 or 5 or 10 mg to 50, 100, 150, 200, 250, 300, 350, 400, 450, or 500 mg sodium phosphate, e.g., $Na_2HPO_4$.

1.12 Kit 1.3-1.10 wherein the kit comprises $Na_2HPO_4$.

1.13 Kit 1.12 wherein the kit comprises 1 or 5 mg to 200 or 500 mg $Na_2HPO_4$, e.g., from about 1 or 5 or 10 mg to 50, 100, 150, 200, 250, 300, 350, 400, 450, or 500 mg $Na_2HPO_4$.

1.14 Kit 1.3-1.13 wherein the kit comprises one or more bulking agents which may provide an adequate structure to the lyophilized cake, e.g., one or more of mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40).

1.15 Kit 1.14 the kit comprises 5 or 10 or 50 mg to 2 or 5 g of one or more bulking agents, e.g., from about 50 or 100 mg to 200, 300, 500, or 800 mg, or 1, 1.5, 2, 3, 4, or 5 g of one or more bulking agents.

1.16 Kit 1.3-1.15 wherein the kit comprises dextran (e.g., dextran 40).

1.17 Kit 1.16 wherein the kit comprises 5 or 10 or 50 mg to 2 or 5 g dextran (e.g., dextran 40), e.g., from about 50 or 100 mg to 200, 300, 500, or 800 mg, or 1, 1.5, 2, 3, 4, or 5 g dextran (e.g., dextran 40).

1.18 Kit 1.3-1.17 wherein the composition comprises one or more solubilizing agents, e.g., ethylenediamine tetraacetic acid (EDTA) or a slat thereof (e.g., calcium disodium EDTA, disodium EDTA, sodium EDTA), alpha cyclodextrin, hydroxypropyl-β-cyclodextrin, polysorbate 80, tert-butanol, isopropanol, dichloromethane, ethanol, acetone, and glycerol; one or more collapse temperature modifiers which may shift the overall collapse temperature higher, e.g., one or more of dextran, Ficoll®, gelatin, and hydroxyethyl starch; one or more tonicity modifiers, e.g., one or more of sodium chloride, potassium chloride, sucrose, mannitol, glucose, and lactose; and one or more antimicrobial agents, e.g., one or more of benzyl alcohol, phenol, 2-phenoxyethanol, m-cresol, parabens (e.g., methyl paraben, ethyl paraben, propyl paraben), benzalkonium chloride, benzethonium chloride, myristyl gamma-picolinium salt (e.g., myristyl gamma-picolinium chloride), and organomercury compounds and salts (e.g., phenyl mercuric acetate, phenyl mercuric borate, phenyl mercuric nitrate, and thimerosal).

1.19 Kit 1.3-1.18 wherein the compound of Formula I, e.g., the compound of 1.1-1.52, or, e.g., the compound of Formula II, e.g., the compound of 2.1-2.26, and the one pharmaceutically acceptable excipients are in the same container or in one or more different containers.

1.20 Kit 1.19 wherein the kit comprises one or more buffering agents, e.g., sodium citrate, potassium citrate, sodium phosphate (e.g., $NaH_2PO_4$ and/or $Na_2HPO_4$), potassium phosphate (e.g., $KH_2PO_4$ and/or $K_2HPO_4$), tris(hydroxymethyl)aminomethane (also known as tris base), tris(hydroxymethyl)aminomethane acetate (also known as tris acetate), zinc chloride, meglumine, sodium acetate, potassium acetate, sodium hydroxide, and arginine, e.g., one or more of sodium citrate, $Na_2HPO_4$, tris(hydroxymethyl)aminomethane, and tris acetate, e.g., $Na_2HPO_4$, e.g., tris(hydroxymethyl)aminomethane, e.g., tris(hydroxymethyl)aminomethane acetate, wherein the one or more buffering agents are in the same container as the compound of Formula I, e.g., the compound of 1.1-1.52, or, e.g., the compound of Formula II, e.g., the compound of 2.1-2.26, or in one or more different containers.

1.21 Kit 1.20 wherein the compound of Formula I, e.g., the compound of 1.1-1.52, or, e.g., the compound of Formula II, e.g., the compound of 2.1-2.26, and one or more of sodium citrate and sodium phosphate (e.g., $Na_2HPO_4$) are in the same container or in one or more different containers.

1.22 Kit 1.20 wherein the compound of Formula 1, e.g., the compound of 1.1-1.52, or, e.g., the compound of Formula II, e.g., the compound of 2.1-2.26, and sodium citrate are in the same container or in different containers.

1.23 Kit 1.20 wherein the compound of Formula I, e.g., the compound of 1.1-1.52, or, e.g., the compound of Formula II, e.g., the compound of 2.1-2.26, and sodium phosphate (e.g., $Na_2HPO_4$) are in the same container or in different containers.

1.24 Kit 1.19-1.23 wherein the kit comprises one or more bulking agents, e.g., one or more of mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40), wherein the one or more bulking agents are in the same container as the compound of Formula I, e.g., the compound of 1.1-1.52, or, e.g., the compound of Formula II, e.g., the compound of 2.1-2.26, or any other component of the kit, or in one or more different containers, e.g., in any combination in any number of different containers.

1.25 Kit 1.24 wherein the compound of Formula I, e.g., the compound of 1.1-1.52, or, e.g., the compound of Formula II, e.g., the compound of 2.1-2.26, and dextran (e.g., dextran 40) are in the same container or in different containers.

1.26 Kit 1.19-1.25 wherein the kit comprises one or more solubilizing agents, e.g., ethylenediamine tetraacetic acid (EDTA) or a salt thereof (e.g., calcium disodium EDTA, disodium EDTA, sodium EDTA), alpha cyclodextrin, hydroxypropyl-β-cyclodextrin, polysorbate 80, tert-butanol, isopropanol, dichloromethane, ethanol, acetone, and glycerol; one or more collapse temperature modifiers, e.g., one or more of dextran, Ficoll®, gelatin, and hydroxyethyl starch; one or more tonicity modifiers, e.g., one or more of sodium chloride, potassium chloride, sucrose, mannitol, glucose, and lactose; and one or more antimicrobial agents, e.g., one or more of benzyl alcohol, phenol, 2-phenoxyethanol, m-cresol, chlorobutanol, parabens (e.g., methyl paraben, ethyl paraben, and propyl paraben), benzalkonium chloride, benzethonium chloride, myristyl gamma-picolinium salt (e.g., myristyl gamma-picolinium chloride), and organomercury compounds and salts (e.g., phenyl mercuric acetate, phenyl mercuric borate, phenyl mercuric nitrate, and thimerosal), wherein the one or more solubilizing agents, collapse temperature modifiers, tonicity modifiers, and antimicrobial agents are in the same container as the compound of Formula I, e.g., the compound of 1.1-1.52, or, e.g., the compound of Formula II, e.g., the compound of 2.1-2.26, or any other component of the kit, or in one or more different containers, e.g., in any combination in any number of different containers.

1.27 Kit I or 1.1-1.26 wherein the compound of Formula I, e.g., the compound of 1.1-1.52, or, e.g., the compound of Formula II, e.g., the compound of 2.1-2.26, is crystalline.

1.28 Kit I or 1.1-1.26 wherein the compound of Formula I, e.g., the compound of 1.1-1.52, or, e.g., the compound of Formula II, e.g., the compound of 2.1-2.26, is amorphous.

1.29 Kit I or 1.1-1.28 wherein the compound of Formula I, e.g., the compound of 1.1-1.52, or, e.g., the compound of Formula II, e.g., the compound of 2.1-2.26, is lyophilized, e.g., by freezing, primary drying, and secondary drying.
1.30 Kit 1.2-1.29 wherein the compound of Formula I, e.g., the compound of 1.1-1.52, or, e.g., the compound of Formula II, e.g., the compound of 2.1-2.26, and the one or more pharmaceutically acceptable excipients are lyophilized.
1.31 Kit I or 1.1-1.30 wherein the compound of Formula 1, e.g., the compound of 1.1-1.52, or, e.g., the compound of Formula II, e.g., the compound of 2.1-2.26, is suitable for constitution, or reconstitution if lyophilized, with a solvent into a pharmaceutically acceptable liquid (e.g., a solution or suspension, e.g., a solution).
1.32 Kit I or 1.1-1.31 wherein the kit comprises a solvent, e.g., a sterile solution, e.g., sterile water for injection, a sterile solution comprising dextrose (e.g., dextrose injection 5%), a sterile solution comprising sodium chloride (e.g., 0.9% sodium chloride injection), a sterile solution comprising benzyl alcohol (e.g., bacteriostatic water for injection with benzyl alcohol or bacteriostatic sodium chloride for injection with benzyl alcohol), or Lactated Ringer's.
1.33 Kit I or 1.1-1.32 wherein the kit comprises 0.5 to 500 mL solvent, e.g., from about 1 to 2 or 500 mL, e.g., from about 1 or 2 to 5, 10, 25, 50, 75, 100, 150, 200, 300 or 500 mL, e.g., from about 1 or 2 to 5, 10, 25, 50, 75, 100, or 200 mL, e.g., from about 5 to 10, 25, 50, or 100 mL.
1.34 Kit I or 1.1-1.33 wherein the kit comprises 0.5 to 500 mL sterile solution, e.g., sterile water for injection, a sterile solution comprising dextrose (e.g., dextrose injection 5%), a sterile solution comprising sodium chloride (e.g., 0.9% sodium chloride injection), a sterile solution comprising benzyl alcohol (e.g., bacteriostatic water for injection with benzyl alcohol or bacteriostatic sodium chloride for injection with benzyl alcohol), or Lactated Ringer's, e.g., from about 1 or 2 mL to 500 mL, e.g., from about 1 or 2 mL to 5, 10, 25, 50, 75, 100, 150, 200, 300 or 500 mL, e.g., from about 1 or 2 mL to 5, 10, 25, 50, 75, 100, or 200 mL, e.g., from about 5 to 10, 25, 50, or 100 mL.
1.35 Kit I or 1.1-1.34 wherein the kit comprises sterile water for injection or a sterile solution comprising sodium chloride (e.g., 0.9% sodium chloride injection).
1.36 Kit 1.35 wherein the kit comprises 0.5 to 500 mL sterile water for injection, e.g., from about 1 or 2 mL to 500 mL, e.g., from about 1 or 2 mL to 5, 10, 25, 50, 75, 100, 150, 200, 300 or 500 mL, e.g., from about 1 or 2 mL to 5, 10, 25, 50, 75, 100, or 200 mL, e.g., from about 5 to 10, 25, 50, or 100 mL.
1.37 Kit I or 1.1-1.36 wherein the kit comprises sterile solution comprising sodium chloride (e.g., 0.9% sodium chloride injection).
1.38 Kit 1.37 wherein the kit comprises 0.5 to 500 mL of a sterile solution comprising sodium chloride (e.g., 0.9% sodium chloride injection), e.g., from about 1 or 2 mL to 500 mL, e.g., from about 1 or 2 mL to 5, 10, 25, 50, 75, 100, 150, 200, 300 or 500 mL, e.g., from about 1 or 2 mL to 5, 10, 25, 50, 75, 100, or 200 mL, e.g., from about 5 to 10, 25, 50, or 100 mL.
1.39 Kit 1.31-1.38 wherein the solvent, e.g., the sterile solution, comprises a buffering agent, e.g., one or more of sodium citrate, potassium citrate, sodium phosphate (e.g., $NaH_2PO_4$ and/or $Na_2HPO_4$), potassium phosphate (e.g., $KH_2PO_4$ and/or $K_2HPO_4$), tris(hydroxymethyl)aminomethane (also known as tris base), tris (hydroxymethyl)aminomethane acetate (also known as tris acetate), zinc chloride, meglumine, sodium acetate, potassium acetate, sodium hydroxide, and arginine, e.g., one or more of sodium citrate, $Na_2HPO_4$, tris (hydroxymethyl)aminomethane, and tris(hydroxymethyl)aminomethane acetate, e.g., $Na_2HPO_4$, e.g., tris (hydroxymethyl)aminomethane, e.g., tris (hydroxymethyl)aminomethane acetate.
1.40 Kit 1.39 wherein the solvent, e.g., the sterile solution, comprises 1 or 5 mg to 200 or 500 mg of one or more buffering agents, e.g., from about 1 or 5 or 10 mg to 50, 100, 150, 200, 250, 300, 350, 400, 450, or 500 mg.
1.41 Kit 1.39 or 1.40 wherein the solvent, e.g. the sterile solution, comprises one or more of sodium citrate and sodium phosphate, e.g., $Na_2HPO_4$.
1.42 Kit 1.39-1.41 wherein the solvent, e.g. the sterile solution, comprises sodium citrate.
1.43 Kit 1.42 wherein the solvent, e.g., the sterile solution, comprises 1 or 5 mg to 200 or 500 mg sodium citrate, e.g., from about 1 or 5 or 10 mg to 50, 100, 150, 200, 250, 300, 350, 400, 450, or 500 mg sodium citrate.
1.44 Kit 1.39-1.43 wherein the solvent, e.g., the sterile solution, comprises sodium phosphate, e.g., $Na_2HPO_4$.
1.45 Kit 1.44 wherein the solvent, e.g., the sterile solution, comprises 1 or 5 mg to 200 or 500 mg sodium phosphate, e.g., from about 1 or 5 or 10 mg to 50, 100, 150, 200, 250, 300, 350, 400, 450, or 500 mg sodium phosphate, e.g., $Na_2HPO_4$.
1.46 Kit 1.32-1.45 wherein the solvent, e.g., the sterile solution, comprises one or more bulking agents, e.g., one or more of maltose, mannose, ribose, cyclodextrin, mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40).
1.47 Kit 1.32-1.46 wherein the solvent, e.g., the sterile solution, comprises 5 or 10 or 50 mg to 2 or 5 g of one or more bulking agents, e.g., from about 50 or 100 mg to 200, 300, 500, or 800 mg, or 1, 1.5, 2, 3, 4, or 5 g of one or more bulking agents.
1.48 Kit 1.32-1.47 wherein the solvent, e.g., the sterile solution, comprises dextran (e.g., dextran 40).
1.49 Kit 1.48 wherein the solvent, e.g. the sterile solution, comprises 5 or 10 or 50 mg to 2 or 5 g dextran (e.g., dextran 40), e.g., from about 50 or 100 mg to 200, 300, 500, or 800 mg, or 1, 1.5, 2, 3, 4, or 5 g dextran (e.g., dextran 40).
1.50 Kit 1.32-1.49 wherein the solvent, e.g., the sterile solution, comprises one or more solubilizing agents, e.g., ethylenediamine tetraacetic acid (EDTA) or a salt thereof (e.g., calcium disodium EDTA, disodium EDTA, sodium EDTA), alpha cyclodextrin, hydroxypropyl-β-cyclodextrin, polysorbate 80, tert-butanol, isopropanol, dichloromethane, ethanol, acetone, and glycerol; one or more collapse temperature modifiers which may shift the overall collapse temperature higher, e.g., one or more of dextran, Ficoll®, gelatin, and hydroxyethyl starch; one or more tonicity modifiers, e.g., one or more of sodium chloride, potassium chloride, sucrose, mannitol, and glucose; and one or more antimicrobial agents, e.g., one or more of benzyl alcohol, phenol, 2-phenoxyethanol, m-cresol, chlorobutanol, parabens (e.g., methyl paraben, ethyl paraben, propyl paraben), benzalkonium chloride, benzethonium chloride, myristyl gamma-picolinium salt (e.g., myristyl gamma-picolinium chloride), and organomercury compounds and salts (e.g., phenyl mercuric acetate, phenyl mercuric borate, phenyl mercuric nitrate, and thimerosal).

1.51 Kit 1.32-1.50 wherein the compound of Formula I, e.g., the compound of 1.1-1.52, or, e.g., the compound of Formula II, e.g., the compound of 2.1-2.26, is admixed with the solvent to form a solution wherein the pH is between pH 7 and pH 10.5, e.g., between pH 7 and pH 9.5, e.g., between pH 7 and pH 8.

1.52 Kit 1.51 wherein the solution is filtered to remove particles and microbes, e.g., filtered prior to injection.

1.53 Kit 1.51 or 1.52 wherein the solution is administered about 24 hours, 12 hours, 10 hours, 8 hours, 2 hours, 1 hour, 30 minutes, 20 minutes, 15 minutes, 10 minutes, 5 minutes, 3 minutes, 2 minutes or 1 minute or less after admixture.

1.54 Kit I or 1.1-1.53 wherein the kit comprises one or more additional therapeutic agents, e.g., one or more additional therapeutic agents for cerebral edema, stroke, traumatic brain injury, glioma (e.g., glioblastoma), meningitis, acute mountain sickness, infection, metabolic disorder, hypoxia, water intoxication, hepatic failure, hepatic encephalopathy, diabetic ketoacidosis, abscess, eclampsia, Creutzfeldt-Jakob disease, lupus cerebritis, optic nerve edema, hyponatremia, fluid retention, ovarian hyperstimulation syndrome, epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or migraines.

1.55 Kit I or 1.1-1.128 wherein the kit comprises one or more additional therapeutic agents, e.g., one or more additional therapeutic agents for pulmonary edema, fibromyalgia, or multiple sclerosis.

1.56 Kit I or 1.1-1.55 wherein the kit comprises instructions for using the compound of Formula 1, e.g., the compound of 1.1-1.52, or, e.g., the compound of Formula II, e.g., the compound of 2.1-2.26, to treat or control a disease or condition mediated by an aquaporin, e.g., diseases or conditions of water imbalance and other diseases, for example, edema of the brain or spinal cord, e.g., cerebral edema, e.g. cerebral edema consequent to head trauma, ischemic stroke, glioma, meningitis, acute mountain sickness, epileptic seizure, infection, metabolic disorder, hypoxia (including general systemic hypoxia and hypoxia due to cardiac arrest), water intoxication, hepatic failure, hepatic encephalopathy, diabetic ketoacidosis, abscess, eclampsia, Creutzfeldt-Jakob disease, lupus cerebritis, cardiac arrest, microgravity and/or radiation exposure, or an invasive central nervous system procedure, e.g., neurosurgery, endovascular clot removal, spinal tap, aneurysm repair, or deep brain stimulation or, e.g., spinal cord edema consequent to spinal cord trauma, e.g., spinal cord compression; or optic nerve edema, e.g., optic nerve edema consequent to microgravity and/or radiation exposure; or retinal edema; or hyponatremia or excessive fluid retention, e.g., consequent to heart failure (HF), liver cirrhosis, nephrotic disorder, syndrome of inappropriate antidiuretic hormone secretion (SIADH), or infertility treatment; or ovarian hyperstimulation syndrome; or epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or glioblastoma; or migraines.

1.57 Kit I or 1.1-1.56 wherein the kit comprises instructions for using 2-{[3,5-bis(trifluoromethyl)phenyl]carbamoyl}-4-chlorophenyl dihydrogen phosphate to treat or control a disease or condition mediated by an aquaporin, e.g., diseases or conditions of water imbalance and other diseases, for example, pulmonary edema, fibromyalgia, or multiple sclerosis.

1.58 Kit I or 1.1-1.57 wherein the kit comprises instructions for administering the compound of Formula I, e.g., the compound of 1.1-1.52, or, e.g., the compound of Formula II, e.g., the compound of 2.1-2.26, to a patient in need thereof.

1.59 Kit I or 1.1-1.57 wherein the kit comprises instructions for mixing the compound of Formula I, e.g., the compound of 1.1-1.52, or, e.g., the compound of Formula II, e.g., the compound of 2.1-2.26, and one or more pharmaceutically acceptable excipients.

1.60 Kit I wherein the kit comprises a pharmaceutical composition comprising a compound of Formula I, e.g., a compound of 1.1-1.52, or, e.g., a compound of Formula II, e.g., a compound of 2.1-2.26, e.g., Composition I, e.g., a composition of 1.1-1.57.

1.61 Kit 1.60 wherein the kit comprises instructions for using the pharmaceutical composition to treat or control a disease or condition mediated by an aquaporin, e.g., diseases or conditions of water imbalance and other diseases, for example, edema of the brain or spinal cord, e.g., cerebral edema, e.g. cerebral edema consequent to head trauma, ischemic stroke, glioma, meningitis, acute mountain sickness, epileptic seizure, infection, metabolic disorder, hypoxia (including general systemic hypoxia and hypoxia due to cardiac arrest), water intoxication, hepatic failure, hepatic encephalopathy, diabetic ketoacidosis, abscess, eclampsia, Creutzfeldt-Jakob disease, lupus cerebritis, cardiac arrest, microgravity and/or radiation exposure, or an invasive central nervous system procedure, e.g., neurosurgery, endovascular clot removal, spinal tap, aneurysm repair, or deep brain stimulation or, e.g., spinal cord edema consequent to spinal cord trauma, e.g., spinal cord compression; or optic nerve edema, e.g., optic nerve edema consequent to microgravity and/or radiation exposure; or retinal edema; or hyponatremia or excessive fluid retention, e.g., consequent to heart failure (HF), liver cirrhosis, nephrotic disorder, syndrome of inappropriate antidiuretic hormone secretion (SIADH), or infertility treatment; or ovarian hyperstimulation syndrome; or epilepsy, retinal ischemia or other diseases of the eye associated with abnormalities in intraocular pressure and/or tissue hydration, myocardial ischemia, myocardial ischemia/reperfusion injury, myocardial infarction, myocardial hypoxia, congestive heart failure, sepsis, neuromyelitis optica, or glioblastoma; or migraines.

1.62 Kit 1.60 wherein the kit comprises instructions for using the pharmaceutical composition to treat or control a disease or condition mediated by an aquaporin, e.g., diseases or conditions of water imbalance and other diseases, for example, pulmonary edema, fibromyalgia, or multiple sclerosis.

1.63 Kit 1.60 wherein the kit comprises instructions for administering the pharmaceutical composition to a patient in need thereof.

1.64 Kit 1.60 wherein the kit comprises instructions for preparing the pharmaceutical composition.

1.65 Kit I or 1.1-1.64 wherein the kit is for use in any of the methods described herein, e.g., for use in Method A, e.g., Method A.1-A.58, for use in Method B, e.g., Method B.1-B.41, e.g., for use in Method C, e.g., C.1-C.8, e.g., for use in Method D, e.g., D.1-D.19, e.g., for use in Method E, e.g., E.1-E.5, e.g., for use in Method F, e.g., F.1-F.5, e.g., for use in Method G, e.g., G.1-G.58.

In some embodiments, the kit is prepared by transferring a liquid comprising a compound of Formula I, e.g., a compound of 1.1-1.52, or, e.g., the compound of Formula II, e.g., the compound of 2.1-2.26, to a container, e.g., a vial, in a predetermined volume first and then subjecting the liquid to a lyophilization process. Alternatively, liquid can be lyophilized in a large volume and then a predetermined amount of the lyophilized preparation can be placed in a container.

In yet another embodiment, provided is a compound of Formula III

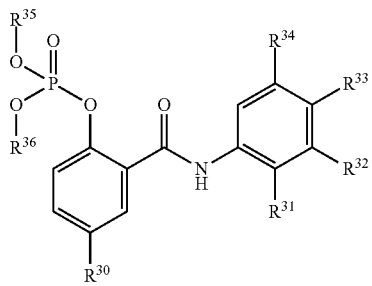

wherein:
$R^{30}$, $R^{31}$, $R^{32}$, $R^{33}$, and $R^{34}$ are independently H, halogen (e.g., Cl or Br), $C_{1-4}$-alkyl, $C_{1-4}$-haloalkyl (e.g., —$CF_3$), or cyano; and
$R^{35}$ and $R^{36}$ are independently protecting groups, e.g., wherein $R^{35}$ and $R^{36}$ are independently a protecting group comprising Si, S, N, and/or O, e.g., wherein $R^{35}$ and $R^{36}$ are independently a protecting group comprising an optionally substituted cyclic or acyclic ether, an optionally substituted silyl (e.g., —Si($C_{1-6}$-alkyl)$_3$, e.g., —Si($C_{1-4}$-alkyl)$_3$, e.g., —Si($CH_3$)$_3$), an optionally substituted silyl ether, an optionally substituted ester, an optionally substituted ketone, or an optionally substituted thioether, e.g., wherein $R^{35}$ and $R^{36}$ are independently —$CH_2OR'$, —$CH_2SR'$,

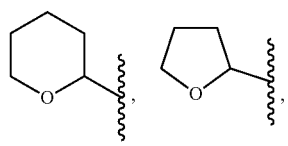

—C(O$C_{1-6}$-alkyl)(R')$_2$, —CH(R')OR', —C(R')$_3$, —Si(R")$_3$, —C(O)R", or —C(O)OR", wherein each R' is independently H, $C_{1-6}$-alkyl (e.g., $C_{1-4}$-alkyl), —$CH_2Si(R")_3$, —$CH_2$-Aryl (e.g., phenyl), —$C_{1-6}$-alkenyl, —$CH_2OSi(R")_3$, alkoxyalkyl, or —$CH_2CH_2Si(R")_3$ and each R" is independently $C_{1-6}$-alkyl (e.g., $C_{1-4}$-alkyl) or aryl optionally substituted with alkoxy (e.g., —$C_{1-6}$-alkoxy, e.g., —$C_{1-4}$-alkoxy), halogen, cyano, or aryl (e.g., phenyl), wherein each $R^1$ is optionally substituted with alkyl, alkoxyalkyl, or aryl, e.g., —($CH_2CH_2$)$_n$—Si($R^{37}$)$_3$), wherein each $R^{37}$ is independently $C_{1-6}$-alkyl, e.g., $C_{1-4}$-alkyl and n is 0 or 1,
and wherein $R^{35}$ and $R^{36}$ are not both —$CH_2$—$C_6H_5$.

Further provided is a compound of Formula III as follows:
3.1 Formula III wherein $R^{30}$, $R^{31}$, $R^{32}$, $R^{33}$, and $R^{34}$ are independently selected from H, halogen (e.g., Cl or Br), $C_{1-4}$-haloalkyl (e.g., —$CF_3$), and cyano.

3.2 Formula III or 3.1 wherein $R^{30}$, $R^{31}$, $R^{32}$, $R^{33}$, and $R^{34}$ are independently selected from H, halogen (e.g., Cl or Br), and $C_{1-4}$-haloalkyl (e.g., —$CF_3$).

3.3 Formula III, 3.1, or 3.2 wherein $R^{30}$, $R^{32}$, and $R^{34}$ are independently selected from halogen (e.g., Cl or Br) and $C_{1-4}$-haloalkyl (e.g., —$CF_3$) and $R^{31}$ and $R^{33}$ are H.

3.4 Formula III or 3.1-3.3 wherein $R^{30}$, $R^{32}$, and $R^{34}$ are independently halogen (e.g., Cl or Br) and $R^{31}$ and $R^{33}$ are H.

3.5 Formula III or 3.1-3.4 wherein $R^{30}$, $R^{32}$, and $R^{34}$ are Cl and $R^{31}$ and $R^{33}$ are H.

3.6 Formula III or 3.1-3.3 wherein $R^{30}$, $R^{32}$, and $R^{34}$ are independently $C_{1-4}$-haloalkyl (e.g., —$CF_3$) and $R^{31}$ and $R^{33}$ are H.

3.7 Formula III, 3.1-3.3, or 3.6 wherein $R^{30}$, $R^{32}$, and $R^{34}$ are —$CF_3$.

3.8 Formula III or 3.1-3.3 wherein $R^{30}$, $R^{32}$, and $R^{34}$ are independently F, Cl, Br, or —$CF_3$ and $R^{31}$ and $R^{33}$ are H.

3.9 Formula III or 3.1-3.3 wherein $R^{30}$ is halogen (e.g., Cl or Br), $R^{31}$ and $R^{33}$ are H, and $R^{32}$ and $R^{34}$ are independently $C_{1-4}$-haloalkyl (e.g., —$CF_3$).

3.10 Formula 3.8 or 3.9 wherein $R^{30}$ is Cl or Br and $R^{32}$ and $R^{34}$ are —$CF_3$.

3.11 Formula 3.10 wherein $R^{30}$ is Cl.

3.12 Formula 3.10 wherein $R^{30}$ is Br.

3.13 Formula III or 3.1 wherein $R^{30}$, $R^{31}$, $R^{32}$, $R^{33}$, and $R^{34}$ are independently H, halogen (e.g., Cl or Br), or cyano.

3.14 Formula 3.13 wherein $R^{30}$ and $R^{31}$ are independently halogen (e.g., Cl or Br), $R^{32}$ and $R^{34}$ are H, and $R^{33}$ is cyano.

3.15 Formula 3.14 wherein $R^{30}$ and $R^{31}$ are Cl.

3.16 Formula III or 3.1-3.15 wherein $R^{35}$ and $R^{36}$ are independently selected from a protecting group comprising Si.

3.17 Formula III or 3.1-3.15 wherein $R^{35}$ and $R^{36}$ are independently selected from —($CH_2CH_2$)$_n$—Si($R^{37}$)$_3$, wherein each $R^{37}$ is independently $C_{1-6}$-alkyl, e.g., $C_{1-4}$-alkyl, e.g., —$CH_3$, and n is 0 or 1, e.g., 0, e.g., 1.

3.18 Formula 3.17 wherein n is 1.

3.19 Formula III or 3.1-3.18 wherein $R^{35}$ and $R^{36}$ are the same.

3.20 Formula III or 3.1-3.19 wherein $R^{35}$ and $R^{36}$ are —$CH_2$—$CH_2$—Si($CH_3$)$_3$.

3.21 Formula III wherein the compound is

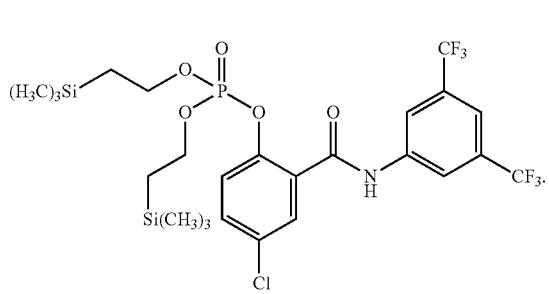

In yet another embodiment, provided is a compound of Formula XX

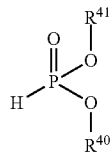

wherein:

$R^{40}$ and $R^{41}$ are independently protecting groups, e.g., wherein $R^{40}$ and $R^{41}$ are independently a protecting group comprising Si, S, N, and/or O, e.g., wherein $R^{40}$ and $R^{41}$ are independently a protecting group comprising an optionally substituted cyclic or acyclic ether, an optionally substituted silyl (e.g., —Si($C_{1-6}$-alkyl)$_3$, e.g., —Si($C_{1-4}$-alkyl)$_3$, e.g., —Si($CH_3$)$_3$), an optionally substituted silyl ether, an optionally substituted ester, an optionally substituted ketone, or an optionally substituted thioether, e.g., wherein $R^{40}$ and $R^{41}$ are independently —$CH_2OR'$, —$CH_2SR'$,

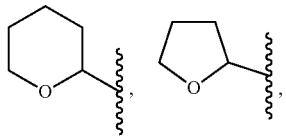

—C(OC$_{1-6}$-alkyl)(R')$_2$, —CH(R')OR', —C(R')$_3$, —Si(R'')$_3$, —C(O)R'', or —C(O)OR'', wherein each R' is independently H, $C_{1-6}$-alkyl (e.g., $C_{1-4}$-alkyl), —$CH_2Si(R'')_3$, —$CH_2$-Aryl (e.g., phenyl), —$C_{1-6}$-alkenyl, —$CH_2OSi(R'')_3$, alkoxyalkyl, or —$CH_2CH_2Si(R'')_3$ and each R'' is independently $C_{1-6}$-alkyl (e.g., $C_{1-4}$-alkyl) or aryl optionally substituted with alkoxy (e.g., —$C_{1-6}$-alkoxy, e.g., —$C_{1-4}$-alkoxy), halogen, cyano, or aryl (e.g., phenyl), wherein each $R^1$ is optionally substituted with alkyl, alkoxyalkyl, or aryl, e.g., —(CH$_2$CH$_2$)$_n$—Si(R$^{37}$)$_3$), wherein each $R^{37}$ is independently $C_{1-6}$-alkyl, e.g., $C_{1-4}$-alkyl and n is 0 or 1, and wherein $R^{41}$ and $R^{341}$ are not both —$CH_2$—$C_6H_5$.

Further provided is a compound of Formula XX as follows:

20.1 Formula XX wherein $R^{40}$ and $R^{41}$ are independently selected from a protecting group comprising Si.

20.2 Formula XX or 20.1, wherein $R^{40}$ and $R^{41}$ are independently selected from —(CH$_2$CH$_2$)$_n$—Si(R$^{37}$)$_3$, wherein each $R^{37}$ is independently $C_{1-4}$-alkyl, e.g., —CH$_3$, and n is 0 or 1.

20.3 Formula XX, 20.1, or 20.2, wherein is 1.

20.4 Formula XX or 20.1-20.3, wherein $R^{40}$ and $R^{41}$ are the same.

20.5 Formula XX or 20.1-20.4 wherein each $R^{37}$ is —CH$_3$.

20.6 Formula XX or 320.1-20.5 wherein $R^{35}$ and $R^{36}$ are —CH$_2$—CH$_2$—Si(CH$_3$)$_3$.

Compounds of Formula I, e.g., compounds of 1.1-1.52, or, e.g., compounds of Formula II, e.g., compounds of 2.1-2.26, compounds Formula III, e.g., compounds of 3.1-3.21, or compounds of Formula XX, e.g., 20.1-20.5, include their polymorphs, hydrates, solvates and complexes.

Some individual compounds within the scope of this disclosure may contain double bonds. Representations of double bonds herein are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that compounds of Formula I, e.g., compounds of formula 1.1-1.52, or, e.g., compounds of Formula II, e.g., compounds of formula 2.1-2.26, and compounds Formula III, e.g., compounds of formula 3.1-3.21, encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on a compound of Formula I, e.g., a compound of 1.1-1.52, or, e.g., a compound of Formula II, e.g., a compound of 2.1-2.26, or a compound of Formula III, e.g., a compound of formula 3.1-3.21, may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of, C, and F. Another example of a useful isotope of a compound of Formula I, e.g., a compound of 1.1-1.52, or, e.g., a compound of Formula II, e.g., a compound of 2.1-2.26, or a compound of Formula III, e.g., a compound of formula 3.1-3.21, is the $^{11}C$ isotope. These radio isotopes may be useful for radio-imaging and/or pharmacokinetic studies of compounds of Formula I, e.g., compounds of 1.1-1.52, or, e.g., compounds of Formula II, e.g., compounds of 2.1-2.26.

Compounds of Formula I, e.g., compounds of formula 1.1-1.52, or, e.g., compounds of Formula II, e.g., compounds of formula 2.1-2.26, and compounds of Formula III, e.g., 3.1-3.21, may be made using the methods as described and exemplified herein and by methods similar thereto and by methods known in the chemical art. Such methods include, but not limited to, those described below. If not commercially available, starting materials for these processes may be made by procedures which are selected from the chemical art using techniques which are similar or analogous to the synthesis of known compounds.

In yet another embodiment, provided are novel processes for the synthesis compounds of Formula I, e.g., compounds of formula 1.1-1.52, or, e.g., compounds of Formula II, e.g., compounds of formula 2.1-2.26. Novel intermediates of Formula III, e.g., compounds of formula 3.1-3.21, may be used in the synthesis of compounds of Formula I, e.g., compounds of formula 1.1-1.52 and in the synthesis of compounds of Formula II, e.g., compounds of formula 2.1-2.26.

U.S. Pat. No. 7,626,042 reports a process for preparing 2-{[3,5-bis(trifluoromethyl)phenyl]carbamoyl}-4-chlorophenyl dihydrogen phosphate from Compound No. 50:

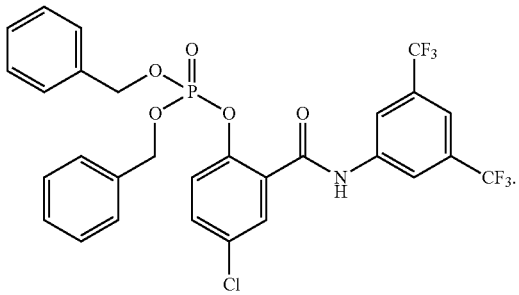 [SMILES: O=C(Nc1cc(C(F)(F)F)cc(C(F)(F)F)c1)c1cc(Cl)ccc1OP(=O)(OCc1ccccc1)OCc1ccccc1]

U.S. Pat. No. 7,626,042 describes that palladium hydroxide on carbon was added to Compound No. 50 in ethyl acetate and the mixture was stirred at room temperature for 1 hour under hydrogen atmosphere.

The inventors have found the process described in U.S. Pat. No. 7,626,042 results in dechlorination of Compound No. 50, which results in a contaminant that is difficult to remove.

Thus, in yet another embodiment, provided is a process (Process I) for synthesizing a compound of Formula I, e.g., a compound of formula 1.1-1.52, comprising deprotonating a compound of Formula IV Formula IV

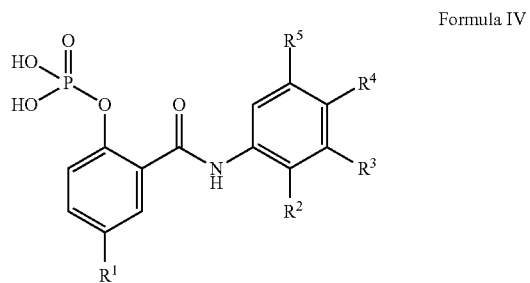

with Q or a salt thereof (e.g., NaOH or KOH), wherein $R^1$, $R^2$, $R^3$, $R^4$, $R^5$, and Q are as defined for Formula I.

Further provided is Process I as follows:
1.1 Process I wherein $R^1$, $R^2$, $R^3$, $R^4$, and $R^5$ are independently H, halogen (e.g., Cl or Br), $C_{1-4}$-haloalkyl (e.g., —$CF_3$), or cyano.
1.2 Process I or 1.1 wherein $R^1$, $R^2$, $R^3$, $R^4$, and $R^5$ are independently H, halogen (e.g., Cl or Br), or $C_{1-4}$-haloalkyl (e.g., —$CF_3$).
1.3 Process I, 1.1, or 1.2 wherein $R^1$, $R^3$, and $R^5$ are independently halogen (e.g., Cl or Br) or $C_{1-4}$-haloalkyl (e.g., —$CF_3$) and $R^2$ and $R^4$ are H.
1.4 Process I or 1.1-1.3 wherein $R^1$, $R^3$, and $R^5$ are independently halogen (e.g., Cl or Br) and $R^2$ and $R^4$ are H.
1.5 Process I or 1.1-1.4 wherein $R^1$, $R^3$, and $R^5$ are Cl and $R^2$ and $R^4$ are H.
1.6 Process I or 1.1-1.3 wherein $R^1$, $R^3$, and $R^5$ are independently $C_{1-4}$-haloalkyl (e.g., —$CF_3$) and $R^2$ and $R^4$ are H.
1.7 Process 1.6 wherein $R^1$, $R^3$, and $R^5$ are —$CF_3$.
1.8 Process I or 1.1-1.3 wherein $R^1$, $R^3$, and $R^5$ are independently F, Cl, Br, or —$CF_3$ and $R^2$ and $R^4$ are H.
1.9 Process I or 1.1-1.3 wherein $R^1$ is halogen (e.g., Cl or Br), $R^2$ and $R^4$ are H, and $R^3$ and $R^5$ are independently $C_{1-4}$-haloalkyl (e.g., —$CF_3$).
1.10 Process 1.8 or 1.9 wherein $R^1$ is Cl or Br and $R^3$ and $R^5$ are —$CF_3$.
1.11 Process 1.10 wherein $R^1$ is Cl.
1.12 Process 1.10 wherein $R^1$ is Br.
1.13 Process I or 1.1 wherein $R^1$, $R^2$, $R^3$, $R^4$, and $R^5$ are independently H, halogen (e.g., Cl or Br), or cyano.
1.14 Process 1.13 wherein $R^1$ and $R^2$ are independently halogen (e.g., Cl or Br), $R^3$ and $R^5$ are H, and $R^4$ is cyano.
1.15 Process 1.14 wherein $R^1$ and $R^2$ are Cl.
1.16 Process I or 1.1-1.15 wherein Q comprises N, e.g., Q is $HOR^8NH_2$, $(HOR^8)_2NH$, or $(HOR^8)_3N$.
1.17 Process I or 1.1-1.14 wherein Q is $HOR^8NH_2$.
1.18 Process I or 1.1-1.14 wherein Q is $(HOR^8)_2NH$.
1.19 Process I or 1.1-1.14 wherein Q is $(HOR^8)_3N$.
1.20 Process I or 1.1-1.19 wherein $R^8$ is —$CH_2$—$CH_2$—.
1.21 Process I or 1.1-1.15 wherein Q is a salt.
1.22 Process 1.21 wherein Q comprises sodium (e.g., NaOH, $NaHCO_3$, $Na_2CO_3$, NaOMe, NaOEt, or NaH).
1.23 Process 1.22 wherein Q is NaOH.
1.24 Process 1.21 wherein Q comprises potassium (e.g., KOH, $KHCO_3$, $K_2CO_3$, KOMe, KOEt, or KH).
1.25 Process 1.24 wherein Q is KOH.
1.26 Process I wherein $R^1$ is halogen (e.g., Cl or Br), $R^2$ and $R^4$ are H, and $R^3$ and $R^5$ are independently $C_{1-4}$-haloalkyl (e.g., —$CF_3$).
1.27 Process 1.26 wherein $R^1$ is Cl or Br and $R^3$ and $R^5$ are —$CF_3$.
1.28 Process 1.27 wherein $R^1$ is Cl.
1.29 Process 1.26-1.28 wherein Q is $HOR^8NH_2$.
1.30 Process 1.29 wherein $R^8$ is —$CH_2$—$CH_2$—.
1.31 Process 1.26-1.28 wherein Q is $(HOR^8)_2NH$.
1.32 Process 1.31 wherein $R^8$ is —$CH_2$—$CH_2$—.
1.33 Process 1.26-1.28 wherein Q is $(HOR^8)_3N$.
1.34 Process 1.33 wherein $R^8$ is —$CH_2$—$CH_2$—.
1.35 Process 1.26-1.28 wherein Q comprises sodium (e.g., NaOH, $NaHCO_3$, $Na_2CO_3$, NaOMe, NaOEt, NaH).
1.36 Process 1.35 wherein Q is NaOH.
1.37 Process 1.26-1.28 wherein Q comprises potassium (e.g., KOH, $KHCO_3$, $K_2CO_3$, KOMe, KOEt, KH).
1.38 Process 1.37 wherein Q is KOH.
1.39 Process I wherein the compound of Formula IV is:

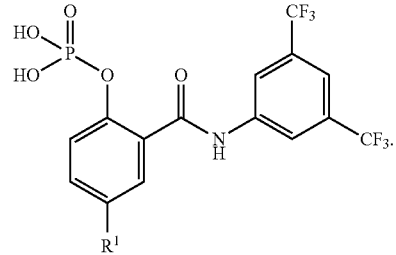

1.40 Process 1.39 wherein Q is $HOR^8NH_2$, $(HOR^8)_2NH$, or $(HOR^8)_3N$.
1.41 Process 1.40 wherein Q is $HOR^8NH_2$.
1.42 Process 1.41 wherein $R^8$ is —$CH_2$—$CH_2$—.
1.43 Process 1.40 wherein Q is $(HOR^8)_2NH$.
1.44 Process 1.43 wherein $R^8$ is —$CH_2$—$CH_2$—.
1.45 Process 1.40 wherein Q is $(HOR^8)_3N$.
1.46 Process 1.45 wherein $R^8$ is —$CH_2$—$CH_2$—.
1.47 Process 1.39 wherein Q is a salt.

1.48 Process 1.47 wherein Q comprises sodium (e.g., NaOH, NaHCO$_3$, Na$_2$CO$_3$, NaOMe, NaOEt, NaH).

1.49 Process 1.48 wherein Q is NaOH.

1.50 Process 1.47 wherein Q comprises potassium (e.g., KOH, KHCO$_3$, K$_2$CO$_3$, KOMe, KOEt, KH).

1.51 Process 1.50 wherein Q is KOH.

1.52 Process I or 1.1-1.51 wherein the reaction occurs in a solvent selected from one or more of H$_2$O and an alcohol (e.g., methanol, ethanol, isopropanol).

1.53 Process 1.52 wherein the solvent is H$_2$O.

1.54 Process 1.52 wherein the solvent is methanol.

1.55 Process I or 1.1-1.54 wherein the reaction is stirred at room temperature.

1.56 Process I or 1.1-1.55 wherein the reaction is stirred for about 2 hours.

1.57 Process I or 1.1-1.56 wherein the compound of Formula IV is mono-deprotonated.

1.58 Process I or 1.1-1.56 wherein the compound of Formula IV is di-deprotonated 1.59 Process I or 1.1-1.58 further comprising deprotecting a compound of Formula III

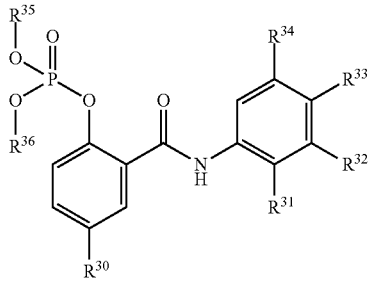

Formula III wherein R$^{30}$, R$^{31}$, R$^{32}$, R$^{33}$, R$^{34}$, R$^{35}$, and R$^{36}$ are as defined above, e.g., a compound of Formula III, e.g., a compound of formula 3.1-3.21, to form a compound of Formula IV.

1.60 Process 1.59 wherein the compound of Formula III is

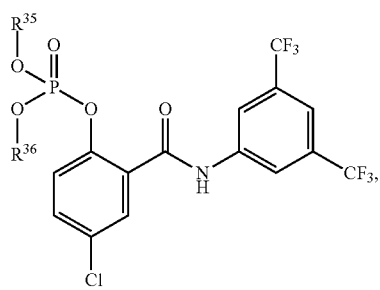

wherein R$^{35}$ and R$^{36}$ are as defined above, e.g., a compound of Formula III, e.g., a compound of formula 3.1-3.21.

1.61 Process 1.59 or 1.60 wherein the compound of Formula III is

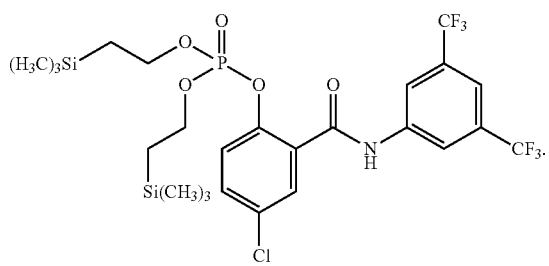

1.62 Process 1.59-1.62 wherein the compound of Formula III is deprotected with a deprotecting agent comprising F.

1.63 Process 1.62 wherein the deprotecting agent is tetra-n-butylammonium fluoride, MgBr$_2$-diethylether, or BBr3.

1.64 Process 1.59-1.62 wherein the deprotecting agent is an acid.

1.65 Process 1.64 wherein the acid is CF$_3$COOH (also known as TFA and trifluoroacetic acid).

1.66 Process 1.59-1.65 wherein the deprotection reaction is stirred at room temperature.

1.67 Process 1.59-1.66 wherein the deprotection reaction is stirred for about 2 hours.

1.68 Process I or 1.1-1.67 further comprising reacting a compound of Formula V

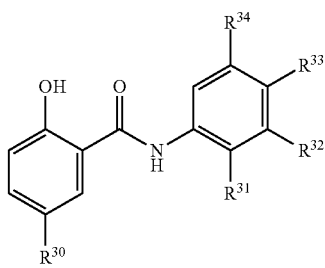

Formula V with a compound of Formula VI

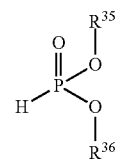

Formula VI to form a compound of Formula III, wherein R$^{30}$, R$^{31}$, R$^{32}$, R$^{33}$, R$^{34}$, R$^{35}$, and R$^{36}$ are as defined above for the compound of Formula III, e.g., the compound of formula 3.1-3.21, e.g., wherein the compound of Formula VI is a compound of Formula XX, e.g., 20.1-20.5.

1.69 Process 1.68 wherein the compound of Formula V is reacted with a compound of Formula XX, e.g., 20.1-20.5.

1.70 Process 1.68 or 1.69 wherein the compound of Formula V is reacted with

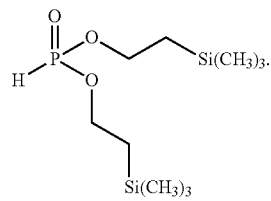

1.71 Process 1.68-1.70 wherein the reaction occurs in the presence of a base.
1.72 Process 1.71 wherein the base comprises nitrogen.
1.73 Process 1.72 wherein the base is a trialkylamine (e.g., $(C_{1-4}\text{-alkyl})_3N$).
1.74 Process 1.73 wherein the base is N,N-diisopropylethylamine (also known as Hünig's base).
1.75 Process 1.68-1.74 wherein the reaction occurs in the presence of a catalyst.
1.76 Process 1.75 wherein the catalyst comprises nitrogen.
1.77 Process 1.76 wherein the catalyst is 4-dimethylaminopyridine (also known as DMAP), 1,8-diazabicyclo[5.4.0]undec-7-ene (also known as DBU), or 1,5-diazabicyclo[4.3.0]non-5-ene (also known as DBN).
1.78 Process 1.68-1.77 wherein the reaction occurs in $CH_3CN$ and $CCl_4$.
1.79 Process 1.68-1.78 wherein the reaction is allowed to warm from about 0° C. to room temperature.
1.80 Process 1.68-1.79 wherein the reaction is stirred for about 20 hours.
1.81 Process I or 1.1-1.80 further comprising reacting a compound of Formula VII

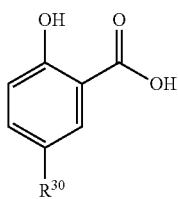

Formula VII to form a compound of Formula V, wherein $R^{30}$ is defined above for the compound of Formula III, e.g., the compound of formula 3.1-3.21.
1.82 Process 1.81 wherein the compound of Formula VII is reacted with a compound of Formula VIII

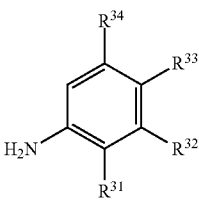

Formula VIII wherein $R^{31}$, $R^{32}$, $R^{33}$, and $R^{34}$ are as defined above for the compound of Formula III, e.g., 3.1-3.21.
1.83 Process 1.81 or 1.82 further comprising first converting the compound of Formula VII to a compound of Formula IX

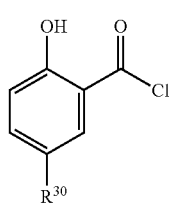

Formula IX wherein $R^{30}$ is as defined above.
1.84 Process 1.83 wherein Formula IX is formed by reaction with a compound comprising P or S.
1.85 Process 1.84 wherein Formula IX is formed by reaction with $PCl_3$, $PCl_5$, or $SOCl_2$.
1.86 Process 1.82-1.85 wherein the reaction occurs in a nonpolar solvent.
1.87 Process 1.86 wherein the nonpolar solvent is toluene.
1.88 Process 1.82-1.87 wherein the reaction is heated to reflux.
1.89 Process 1.82-1.88 wherein the reaction is stirred for about 12 hours.
1.90 Process I or 1.1-1.89 wherein the process is as depicted below:

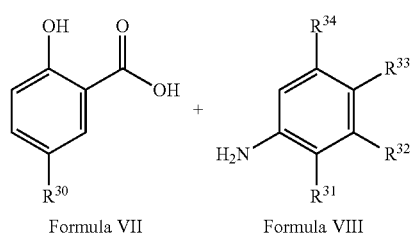
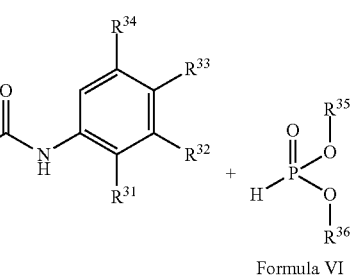
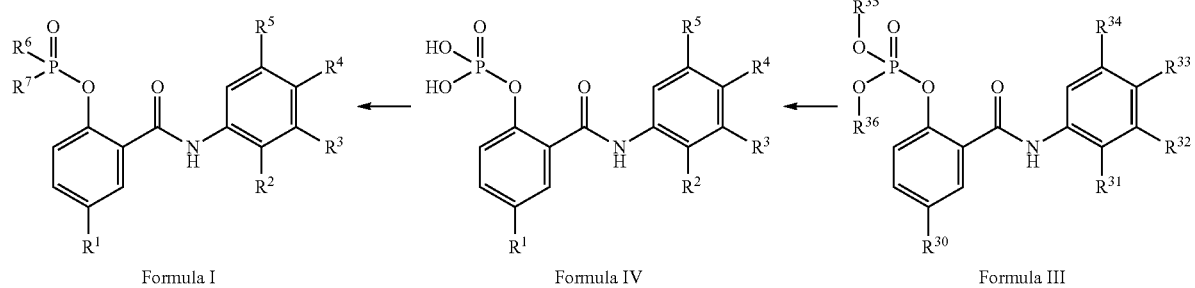

wherein $R^1$, $R^2$, $R^3$, $R^4$, $R^5$, $R^6$, $R^7$, $R^{30}$, $R^{31}$, $R^{32}$, $R^{33}$, $R^{34}$, $R^{35}$, and $R^{36}$ are as defined above.
1.91 Process I or 1.1-1.90 wherein the process is as depicted below:
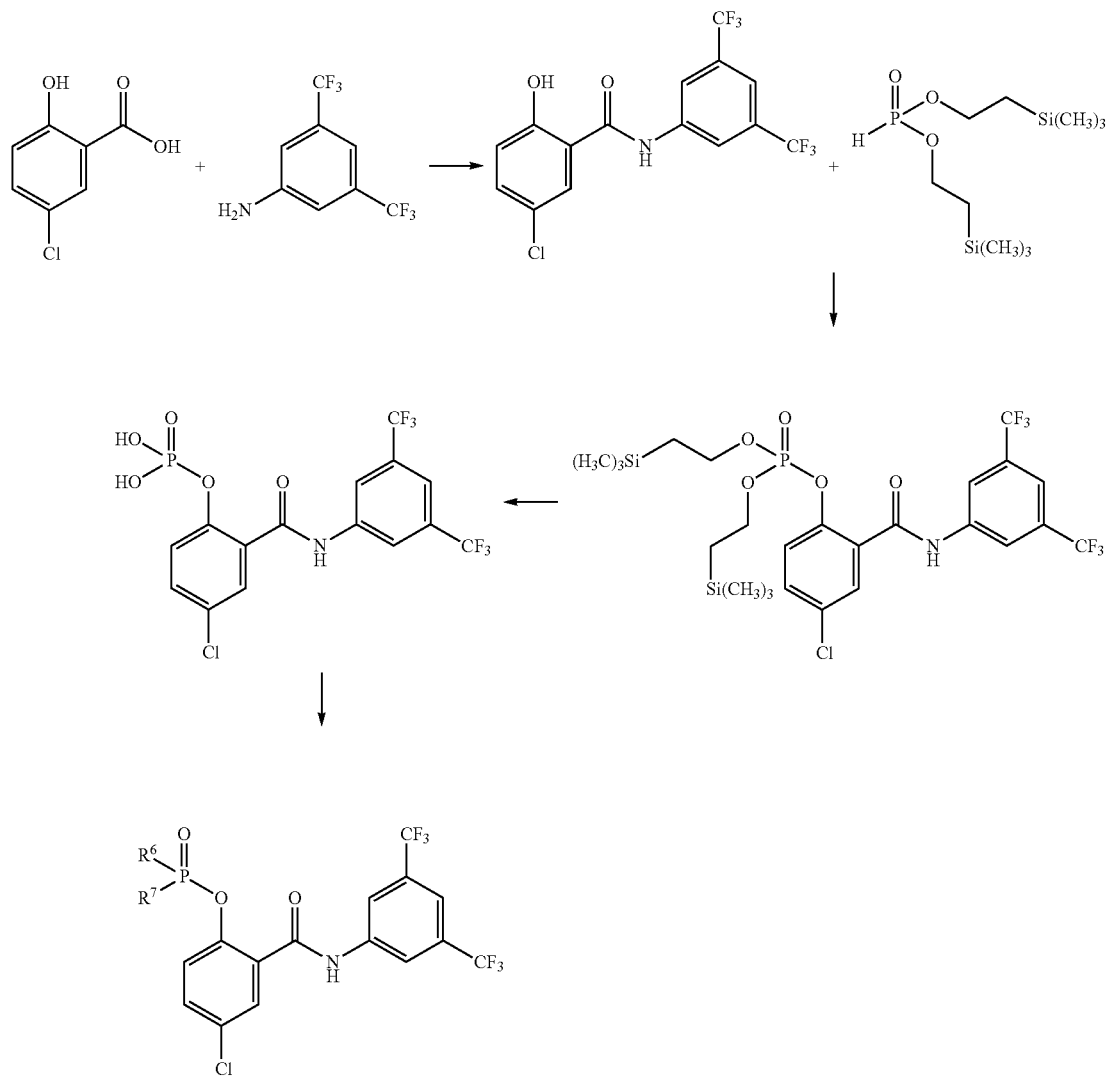
wherein $R^6$ and $R^7$ are as defined above.
1.92 Process I or 1.1-1.91 wherein the process is as depicted below:
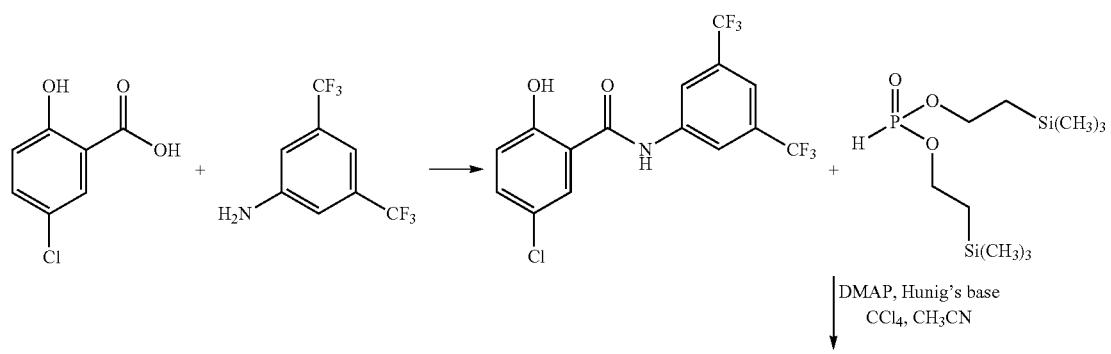

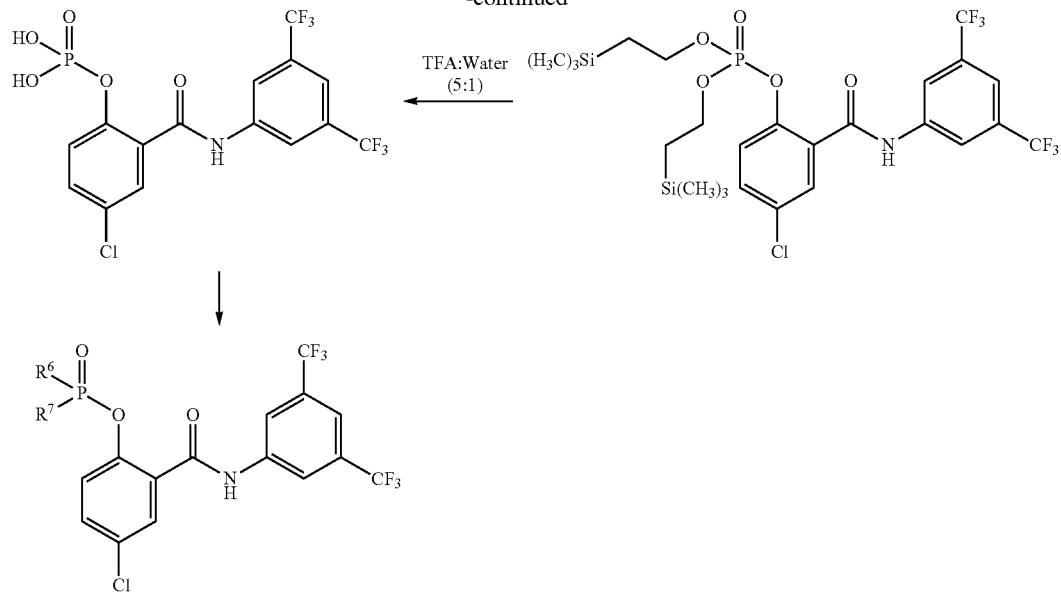

wherein $R^6$ and $R^7$ are as defined above.

1.93 Process I or 1.1-1.92 further comprising isolating the compound of Formula I, e.g., the compound of formula 1.1-1.52.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

EXAMPLES

The synthetic methods for various compounds of Formula I are illustrated below. The intermediates of compounds of Formula I as well as other compounds of Formula I may be made using the methods as similarly described below and/or by methods similar to those generally described in the detailed description and by methods known in the chemical art.

Terms and Abbreviations

DMAP=4-(dimethylamino)pyridine
Hünig's base=N,N-diisopropylethylamine
TFA=trifluoroacetic acid Example 1

2-{[3,5-Bis(trifluoromethyl)phenyl]carbamoyl}-4-chlorophenyl dihydrogen phosphate

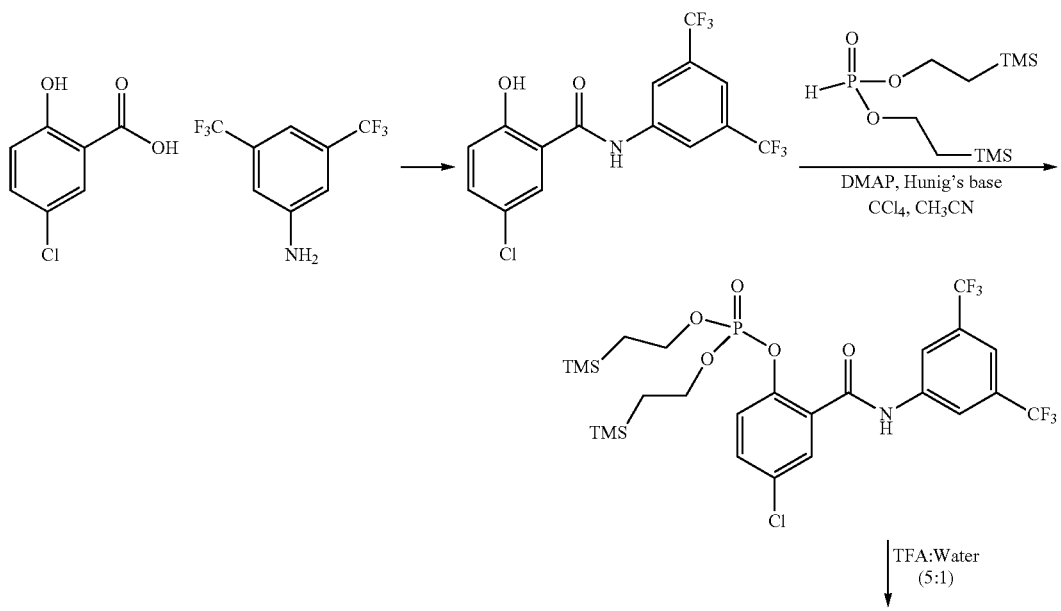

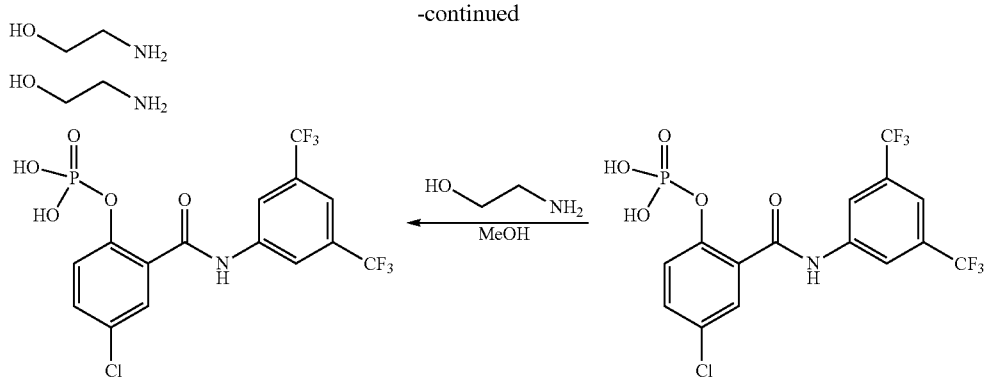

Step 1: N-(3,5-bis(trifluoromethyl)phenyl)-5-chloro-2-hydroxybenzamide (Compound 1)

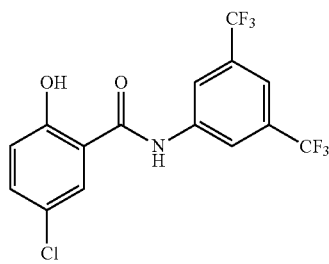 [SMILES: O=C(Nc1cc(C(F)(F)F)cc(C(F)(F)F)c1)c1cc(Cl)ccc1O]

5-chloro salicylic acid (8.75 g, 50 mmol, 1 eq) is dissolved in toluene (300 mL) under $N_2$ atmosphere then phosphorus trichloride (2.2 mL, 25 mmol, 0.5 eq) is added dropwise followed by 3,5-bis(trifluoromethyl)aniline (10 g, 43.7 mmol, 0.87 eq). The reaction mixture is stirred under reflux for 12 h then cooled to room temperature. The reaction mixture is quenched with $NaHCO_3$ saturated solution and stirred for 10 min. To this solution is added 1M HCl (100 mL) until the pH of the aqueous layer is 5 and the aqueous layer is extracted with ethyl acetate (2×300 mL). The combined organics are then dried over sodium sulfate and concentrated in vacuo to yield the crude product which is purified by flash chromatography (5-20% EtOAc/hex). The yield of pure product as a white solid is 16 g (yield 85%) which is >95% pure by $^1H$ NMR. $^1H$ NMR (400 MHz, $CDCl_3$): δ 11.35 (bs, 1H), 10.85 (bs, 1H), 8.40 (s, 2H), 7.80-7.79 (m, 2H), 7.50 (dd, 1H), 7.00 (d, 1H).

Step 2: 2-((3,5-bis(trifluoromethyl)phenyl)carbamoyl)-4-chlorophenyl bis(2-(trimethylsilyl)ethyl) phosphate

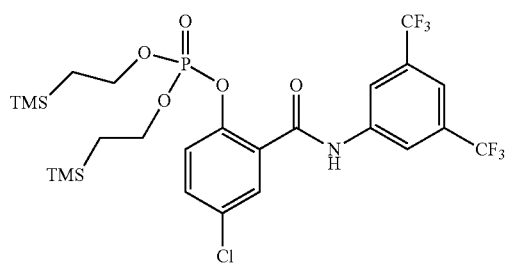 [SMILES: C[Si](C)(C)CCOP(=O)(OCC[Si](C)(C)C)Oc1ccc(Cl)cc1C(=O)Nc1cc(C(F)(F)F)cc(C(F)(F)F)c1]

N-(3,5-bis(trifluoromethyl)phenyl)-5-chloro-2-hydroxybenzamide (4.0 g, 0.01 mol, 1 eq) is dissolved in $CH_3CN$ (104 mL) then DMAP (0.08 g, 0.001 mol, 0.06 eq), Hunig's base (7.36 mL, 0.021 mol, 2 eq) and $CCl_4$ (8.02 g, 0.052 mol, 5 eq) are added in this order. The solution is cooled to 0° C. and the $HP(O)(OCH_2CH_2Si(CH_3)_3)_2$ (4.66 g, 0.016 mol, 1.5 eq) in $CH_3CN$ (5 mL) is added dropwise. The reaction mixture is stirred at room temperature for 20 h then water is added and extracted twice with EtOAc. The combined organic layers are washed with a saturated solution of NaCl, dried over $Na_2SO_4$, filtered and the solvent is concentrated in vacuo to give the crude material which is used as such for next step. $^1H$ NMR (200 MHz, $CDCl_3$): δ 10.20 (bs, 1H), 8.32 (s, 2H), 7.90 (s, 1H), 7.62 (s, 1H), 7.45-7.40 (m, 1H), 7.30-7.28 (m, 1H), 4.40-4.30 (m, 4H), 1.20-1.00 (m, 4H), 0.0 (s, 18H).

Step 3: 2-((3,5-bis(trifluoromethyl)phenyl)carbamoyl)-4-chlorophenyl Dihydrogen Phosphate

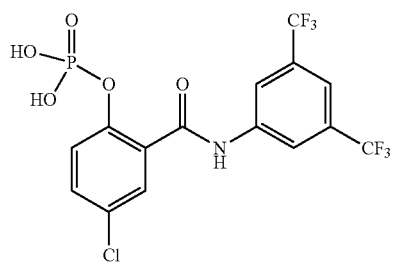 [SMILES: O=C(Nc1cc(C(F)(F)F)cc(C(F)(F)F)c1)c1cc(Cl)ccc1OP(=O)(O)O]

2-((3,5-bis(trifluoromethyl)phenyl)carbamoyl)-4-chlorophenyl bis(2-(trimethylsilyl)ethyl) phosphate (6.64 g, 0.01 mol, 1 eq) is dissolved in a mixture TFA:Water (5:1, 50 mL). The reaction mixture is stirred at room temperature for 2 h then solvent is concentrated in vacuo. The resulting white solid is dissolved in $Et_2O$ (20 mL) then concentrated in vacuo. This operation is repeated twice or until the compound becomes much less soluble in $Et_2O$. The resulting material is suspended in a mixture $Et_2O$:Hex (6:1, 50 mL) and filtered to give the desire material as light red solid. Finally, the solid is dissolved in water (100 mL), filtered and the resulting aqueous solution is freeze dried to give the desired product as a white solid (yield 76% over two steps, 97% pure by HPLC). $^1H$ NMR (400 MHz, $CD_3OD$): δ 8.38 (s, 2H), 7.78 (s, 1H), 7.70 (s, 1H), 7.55-7.50 (m, 1H), 7.45-7.43 (m, 1H).

Example 2

2-((3,5-bis(trifluoromethyl)phenyl)carbamoyl)-4-chlorophenyl Phosphate Bis Ethanolamine Salt

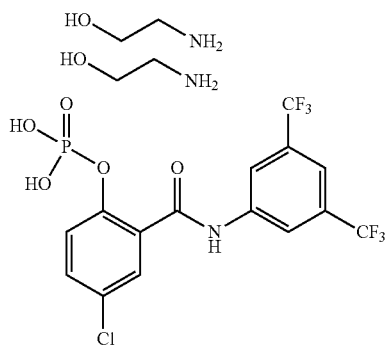

2-((3,5-bis(trifluoromethyl)phenyl)carbamoyl)-4-chlorophenyl dihydrogen phosphate (2.14 g, 0.005 mol, 1 eq) is dissolved in MeOH (46 mL) then ethanolamine (0.56 mL, 0.009 mol, 2 eq) is added. The reaction mixture is stirred at room temperature for 2 h then solvent is concentrated in vacuo to give the desired product as a white solid (yield 84%, 97% pure by HPLC). $^1$H NMR (300 MHz, D$_2$O): δ 8.15 (s, 2H), 7.85 (d, 2H), 7.37-7.34 (m, 2H), 3.62 (t, 4H), 2.95 (t, 4H).

Example 3

2-((3,5-bis(trifluoromethyl)phenyl)carbamoyl)-4-chlorophenyl Phosphate Bis Diethanolamine Salt

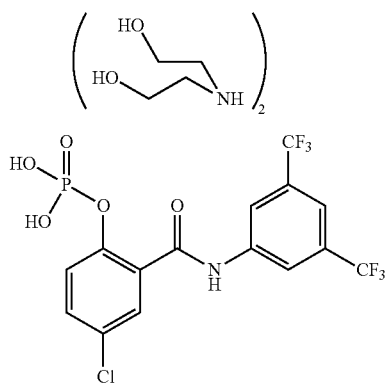

2-((3,5-bis(trifluoromethyl)phenyl)carbamoyl)-4-chlorophenyl dihydrogen phosphate (300 mg, 0.647 mmol, 1 eq) is dissolved in MeOH (3.2 mL) then diethanolamine (0.124 mL, 1.294 mmol, 2 eq) is added. The reaction mixture is stirred at room temperature for 2 h then solvent is concentrated in vacuo to give the desire product as a yellow foam (yield 100%, 95% pure by HPLC). $^1$H NMR (500 MHz, DMSO-d$_6$): δ 8.52 (s, 2H), 7.76 (s, 1H), 7.62 (s, 1H), 7.48 (d, 1H), 7.37 (d, 1H), 3.55 (s, 8H), 2.80 (s, 8H).

Example 4

2-((3,5-bis(trifluoromethyl)phenyl)carbamoyl)-4-chlorophenyl Phosphate Bis Triethanolamine Salt

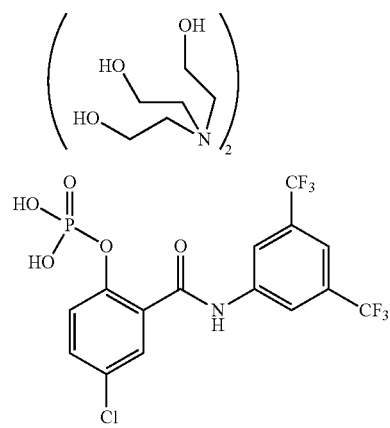

2-((3,5-bis(trifluoromethyl)phenyl)carbamoyl)-4-chlorophenyl dihydrogen phosphate (300 mg, 0.647 mmol, 1 eq) is dissolved in MeOH (3.2 mL) then triethanolamine (0.172 mL, 1.294 mmol, 2 eq) is added. The reaction mixture is stirred at room temperature for 2 h then solvent is concentrated in vacuo to give the desired product as a yellow oil (yield 100%, 98% pure by HPLC). $^1$H NMR (500 MHz, DMSO-d$_6$): δ 8.50 (s, 2H), 7.76 (s, 1H), 7.62 (s, 1H), 7.52 (d, 1H), 7.29 (d, 1H), 3.55 (s, 12H), 2.82 (s, 12H).

Example 5

2-((3,5-bis(trifluoromethyl)phenyl)carbamoyl)-4-chlorophenyl Phosphate Bis Sodium Salt

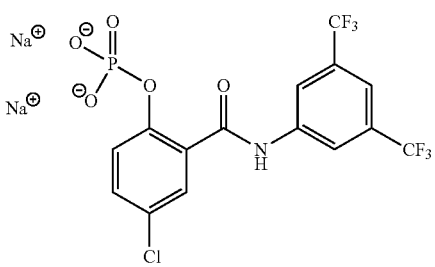 [SMILES: [Na+] ; [Na+] ; O=C(Nc1cc(C(F)(F)F)cc(C(F)(F)F)c1)c1cc(Cl)ccc1OP(=O)([O-])[O-]]

2-((3,5-bis(trifluoromethyl)phenyl)carbamoyl)-4-chlorophenyl dihydrogen phosphate (300 mg, 0.647 mmol, 1 eq) is suspended in water (6.4 mL) then NaOH (1M) (1.29 mL, 1.294 mmol, 2 eq) is added. The reaction mixture is stirred at room temperature for 2 h then the solution is filtered and freeze dried to give the desired product as a white solid (yield 100%, 93% pure by HPLC).

Example 6

2-((3,5-bis(trifluoromethyl)phenyl)carbamoyl)-4-chlorophenyl Phosphate Bis Potassium Salt

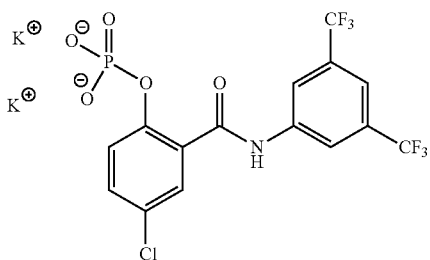 [SMILES: [K+] ; [K+] ; O=C(Nc1cc(C(F)(F)F)cc(C(F)(F)F)c1)c1cc(Cl)ccc1OP(=O)([O-])[O-]]

2-((3,5-bis(trifluoromethyl)phenyl)carbamoyl)-4-chlorophenyl dihydrogen phosphate (300 mg, 0.647 mmol, 1 eq) is suspended in water (6.4 mL) then KOH (1M) (1.29 mL, 1.294 mmol, 2 eq) is added. The reaction mixture is stirred at room temperature for 2 h then the solution is filtered and freeze dried to give the desired product as a white solid (yield 100%, 82% pure by HPLC).

Example 7

2-((3,5-bis(trifluoromethyl)phenyl)carbamoyl)-4-chlorophenyl Hydrogen Phosphate Mono Sodium Salt, 2-((3,5-bis(trifluoromethyl)phenyl)carbamoyl)-4-chlorophenyl Hydrogen Phosphate Bis Sodium Salt, and 2-((3,5-bis(trifluoromethyl)phenyl)carbamoyl)-4-chlorophenyl Hydrogen Phosphate Bis Ethanolamine Salt 2-((3,5-bis(trifluoromethyl)phenyl)carbamoyl)-4-chlorophenyl hydrogen phosphate mono sodium salt, 2-((3,5-bis(trifluoromethyl)phenyl)carbamoyl)-4-chlorophenyl phosphate bis sodium salt, and 2-((3,5-bis(trifluoromethyl)phenyl)carbamoyl)-4-chlorophenyl phosphate bis ethanolamine salt are made as follows: 2 mM of 2-((3,5-bis(trifluoromethyl)phenyl)carbamoyl)-4-chlorophenyl dihydrogen phosphate is dissolved in ethanol 50 ml and appropriate equivalents of each base are added. Evaporation gives salts which are dissolved in water and freeze dried.

Example 8

2-((3,5-bis(trifluoromethyl)phenyl)carbamoyl)-4-chlorophenyl Phosphate Mono Ethanolamine Salt (Compound 2.19)

2-((3,5-bis(trifluoromethyl)phenyl)carbamoyl)-4-chlorophenyl hydrogen phosphate mono ethanolamine salt is made as follows: 1 g of 2-((3,5-bis(trifluoromethyl)phenyl)carbamoyl)-4-chlorophenyl dihydrogen phosphate is dissolved in isopropanol and 1 eq ethanol amine is added. Evaporation gave 2-((3,5-bis(trifluoromethyl)phenyl)carbamoyl)-4-chlorophenyl hydrogen phosphate mono ethanolamine salt.

Example 9

Stability and Solubility

To understand the stability and solubility of the novel prodrug salts a 95% pure lot of 2-((3,5-bis(trifluoromethyl)phenyl)carbamoyl)-4-chlorophenyl dihydrogen phosphate is purified as follows. 15 g is dissolved in 1.2 L of water with 120 mM of sodium hydroxide and extracted with 500 ml ethyl acetate to remove phenol and non acid impurities. The aqueous layer is acidified with concentrated HCl to pH 1.2 and extracted with ethyl acetate 1 L followed by 600 ml. The ethyl acetate layer is dried MgSO$_4$ and sodium sulphate, filtered, and evaporated to give about 13 g of 98% pure 2-((3,5-bis(trifluoromethyl)phenyl)carbamoyl)-4-chlorophenyl dihydrogen phosphate. NMR showed 1 mole of ethyl acetate trapped in solid. Ethyl acetate is removed by adding 100 ml of methanol and evaporating. 2-((3,5-bis(trifluoromethyl)phenyl)carbamoyl)-4-chlorophenyl dihydrogen phosphate is stable at RT for a week or more. Sample kept at RT. It is soluble at 5 mg/mL in 1% Na$_2$HPO$_4$ giving pH of about 7. Dissolved in 2% Na$_2$HPO$_4$ at 5 mg/mL gives pH of 7.4

2-((3,5-bis(trifluoromethyl)phenyl)carbamoyl)-4-chlorophenyl hydrogen phosphate mono sodium salt ("mono sodium salt"), 2-((3,5-bis(trifluoromethyl)phenyl)carbamoyl)-4-chlorophenyl phosphate bis sodium salt ("bis sodium salt"), and 2-((3,5-bis(trifluoromethyl)phenyl)carbamoyl)-4-chlorophenyl phosphate bis ethanolamine salt ("bis ethanolamine salt") are made and freeze dried as in Example 7. In all cases stability studies show hydrolysis in the solid state at about 1% per day. Solubilities are about 5 mg/mL for mono sodium salt and 10 mg/mL for both bis sodium and bis ethanolamine salt in water.

Final pH of solutions are about 7.5 for the bis ethanolamine salt, pH 8.5 for mono sodium salt, and pH 9.5 for bis sodium salt in water. In all cases solutions of these salts show less than 1% phenol over 12 hrs. Longer term their stability is the same as the solid samples (about 1% per day at RT). Hydrolysis rate is expected to be faster at higher pH.

2-((3,5-bis(trifluoromethyl)phenyl)carbamoyl)-4-chlorophenyl phosphate mono ethanolamine salt ("mono ethanolamine salt") is made as in Example 8. Surprisingly, the mono ethanolamine salt only shows about 1% hydrolysis after 5 days at RT. Its solubility in water is about 5 mg/ml. Solubility is expected to be higher at higher pH.

Example 10—Phenylbenzamide-AQP Structure-Activity Relationship

Figure 1A:
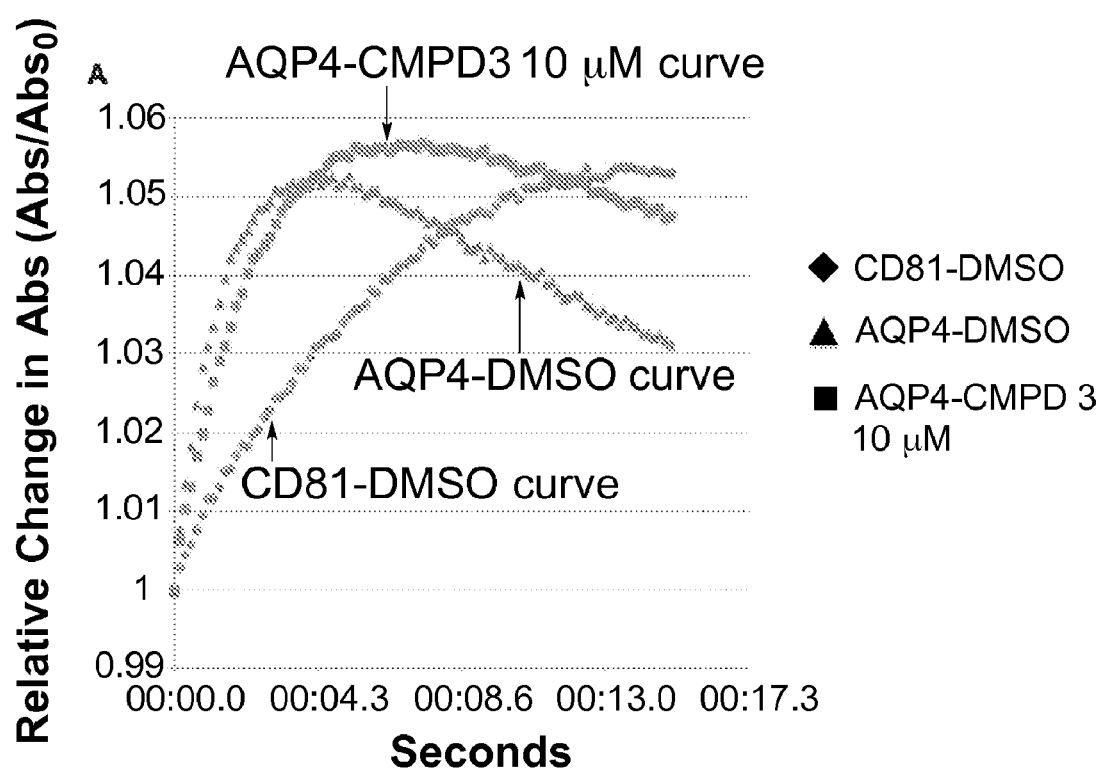
FIG. 1 depicts results of aquaporin-4 (FIG. 1A) and aquaporin-2 (FIG. 1B) mediated cell volume change assay, and the inhibitory effect of 5-chloro-N-(3,5-dichlorophenyl)-2-hydroxybenzamide (Compound 3) against these aquaporins.
Figure 1B:
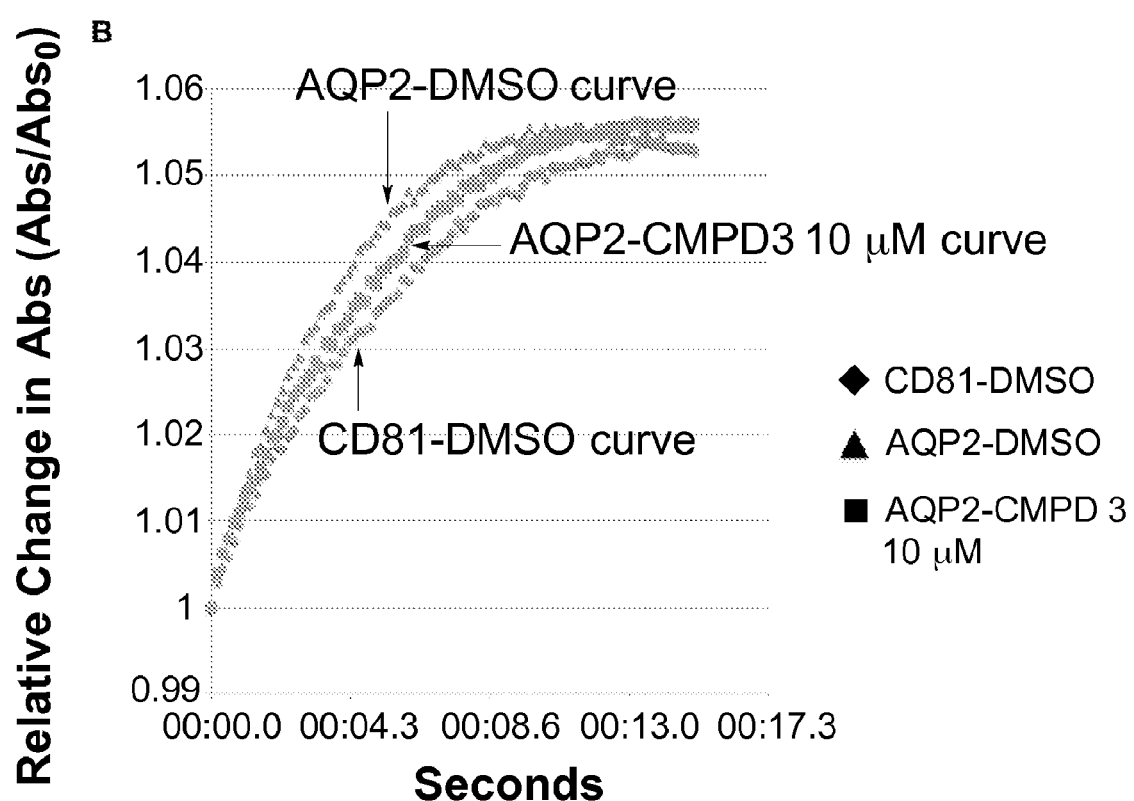

Structure activity relationships (SARs) are determined by assaying analogues of selected hits to guide chemistry for the preparation of new molecules to be tested for improved potency. For this iterative process we use a quantitative kinetic assay—the Aquaporin-Mediated Cell Volume Change Assa—in a 96-well multiplate reader. It detects changes in light scattering by a monolayer of CHO cells expressing the desired AQP as they shrink when exposed to hypertonic solution (300 mOsm→530 mOsm). FIG. 1 depicts the aquaporin-mediated cell volume change assay with AQP4 expressing cells (FIG. 1A) and AQP2 expressing cells (FIG. 1B). The cells expressing aquaporins shrink more rapidly than control cells, due to enhanced water flow, which shrinkage can be inhibited by a compound that inhibits the aquaporin.

In FIG. 1, aquaporin-expressing cells are shown in the presence of DMSO (triangles) or in the presence of the test compound (here, Compound 3) at 10 µM (squares), along with CHO-CD81 expressing control cells in the presence of DMSO (diamonds). Each curve represents an average of 16 wells in the 96-well plate.

In FIG. 1A, when the AQP4b cells treated with DMSO are exposed to hypertonic shock, the cells show rapid shrinking, giving a rise in light scattering (increasing relative change in absorbance, Abs/Abs$_0$) followed by a decay as cells detach from the plate. The CHO-AQP4b cell line shows a 4.5-fold increase in the rate of shrinking compared to CHO-CD81 control cells (fitted to a double exponential model). CHO-AQP4b cells treated with the Compound 3 analogue at 10 µM (squares) show a slower rate of shrinking (55% inhibition) as seen by characteristic 'unbending' of the light scattering curve. Similarly, FIG. 1B depicts an experiment comparing CHO-AQP2 treated with DMSO or with Compound 3 at 10 µM. Aquaporin-2 has a lower intrinsic water permeability than AQP4 as observed here. CHO-AQP2 cell lines treated with DMSO (FIG. 1B, triangles) show a 1.7-fold increase in the rate of shrinking compared to CHO-CD81 control cells (diamonds) also treated with DMSO (fitted to a double exponential model) (FIG. 1B). CHO-AQP2 cells treated with Compound 3 at 10 µM (squares) show a slower rate of shrinking (81% inhibition), when comparing the relative change in Abs (Abs/Abs$_0$) (FIG. 1B).

The data indicates that in this assay, Compound 3 is capable of significantly inhibiting AQP2 and AQP4 activity, e.g. by greater than 50%, at concentrations of 10 µM.

Example 11—Aquaporin Specificity of the Phenylbenzamide Compounds

Figure 2:
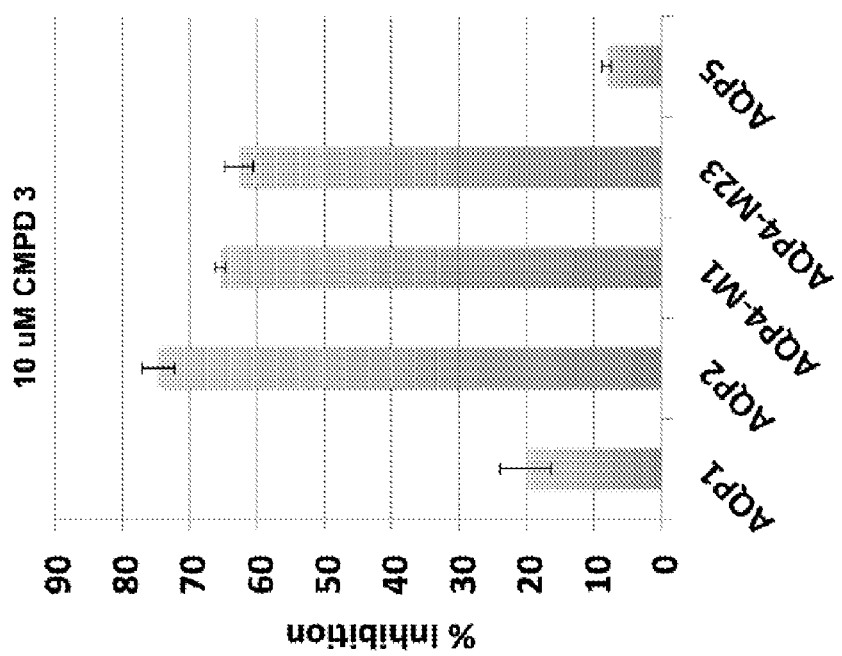
FIG. 2 depicts specificity of 5-chloro-N-(3,5-dichlorophenyl)-2-hydroxybenzamide (Compound 3) towards AQP-1, AQP-2, AQP-4-M1, AQP-4-M23, and AQP-5.

The specificity of the compounds is tested against the most closely related of the 13 known aquaporins: AQP1, AQP2, AQP5 and both splice variants of AQP4 (A and B). A stable CHO cell line is created for each of the above aquaporins and the inhibition of water permeability using the Aquaporin-Mediated Cell Volume Change Assay with 10 µM Compound 3 is tested. Compound 3 inhibits AQP2 and 4, while it poorly inhibits AQP1 and 5 (FIG. 2).

Example 12—Direct Drug-Target Interactions Between Phenylbenzamides and AQP4

Figure 3:
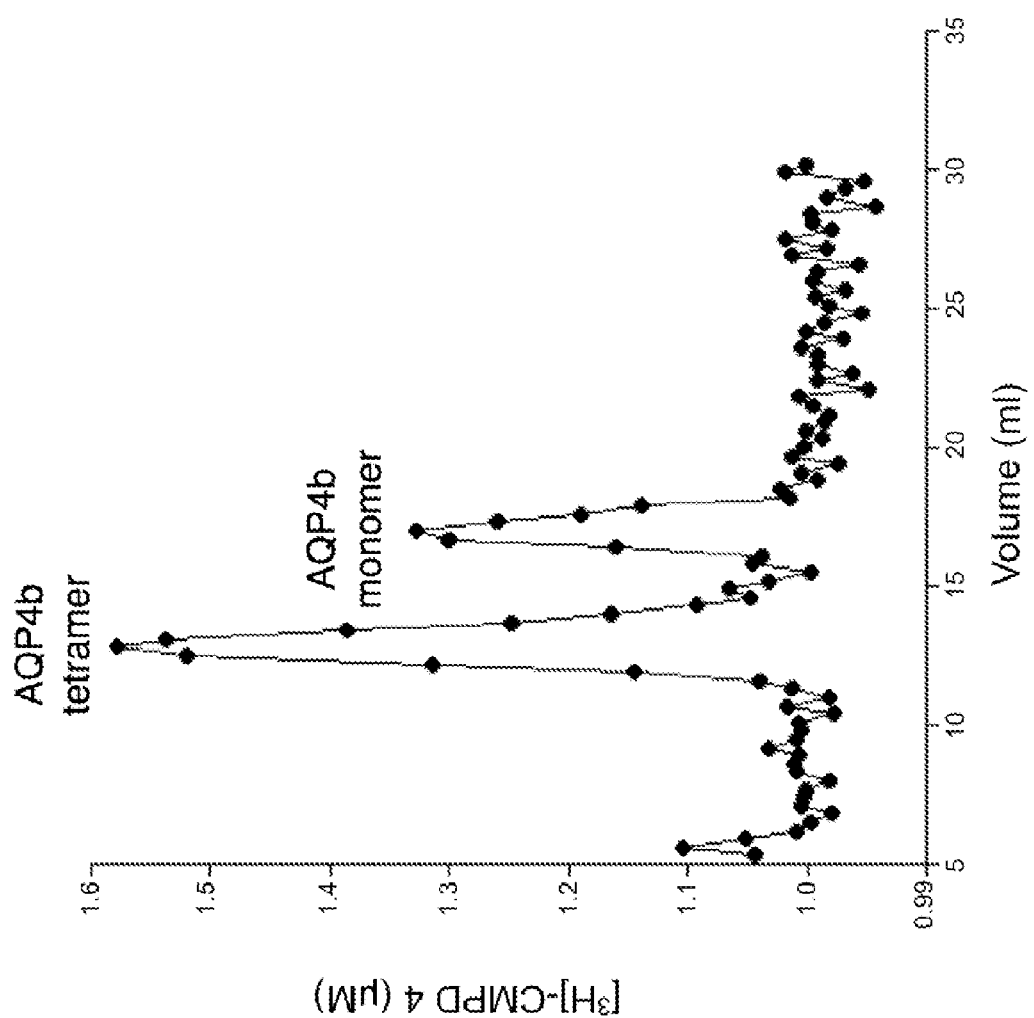
FIG. 3 depicts a Hummel-Dryer style assay for [3H]-labeled N-(3,5-bis(trifluoromethyl)phenyl)-2-hydroxy-5-(trifluoromethyl)benzamide (Compound 4) binding to purified AQP4b.

To support the mechanism of action by which phenylbenzamides directly block AQP4, we perform in vitro binding studies using purified AQP4b and Compound 4 radiolabeled with $^3$H. Using a Hummel-Dryer style assay, a gel filtration column is equilibratrated with buffer containing detergent, to maintain solubility of AQP4b, and 1 µM [$^3$H]-Compound 4. AQP4b is diluted to 250 µM in this column buffer and incubated at RT for 30 min. The sample is then applied to the column, fractions collected and the presence of [$^3$H]-Compound 4 detected by liquid scintillation counting. FIG. 3 shows the elution profile of [$^3$H]-Compound 4 from the gel filtration column with the elution positions of tetrameric and monomeric AQP4b indicated. The rise in [$^3$H]-Compound 4 from a baseline value of 1 µM represents binding to each of these proteins. Although no monomeric AQP4b can be readily detected in our highly purified AQP4b by conventional means, this assay reveals the presence of a small, albeit vanishing, amount of monomer. The relative affinities for Compound 4 are ~100 µM and less than 1 µM for tetramer and monomer, respectively. This assay shows relatively weak binding of Compound 4 to solubilized AQP4b; nevertheless, it clearly demonstrates that this phenylbenzamide directly interacts with AQP4b.

Example 13—Pharmacological Proof-of-Concept

Mouse Water Toxicity Model—Survival Curves: The in vivo efficacies of the compounds are tested using the mouse water toxicity model, where a mouse is injected with water at 20% of its body weight. Manley, G. T. et al. *Aquaporin-4 deletion in mice reduces brain edema after acute water intoxication and ischemic stroke*. Nat Med 6, 159-163 (2000); Gullans, S. R. & Verbalis, J. G. *Control of brain volume during hyperosmolar and hypoosmolar conditions*. Annual Review of Medicine 44, 289-301 (1993). The resulting euvolemic hyponatremia rapidly leads to CE, making this a practical model to test an inhibitor of the CNS aquaporin, AQP4b.

Figure 4:
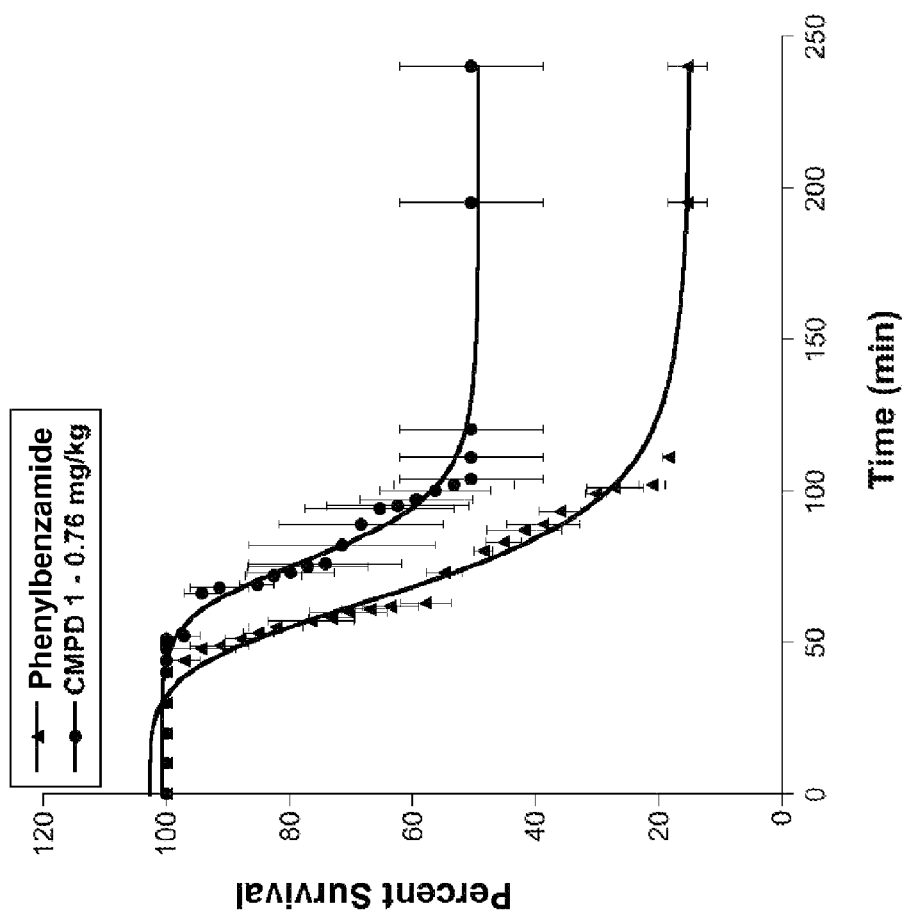
FIG. 4 depicts percent survival curves for the water toxicity mouse model using 0.76 mg/kg N-[3,5-bis(trifluoromethyl)phenyl]-5-chloro-2-hydroxybenzamide (Compound 1).

The ability of mice to survive H$_2$O toxicity is determined in three experiments using 10-12 mice each (16-19 weak old male/female). Deionized water is prepared for injection with either 0.39 mg/kg phenylbenzamide (placebo) or 0.76 mg/kg with test compound. FIG. 4 shows the combined results of these experiments (n=33 placebo, n=34 Compound 1). Percent survival of the Compound 1 cohorts improves 3.2 fold and the time to 50% survival for animals treated with Compound 1 is improved by roughly 52 min.

Mouse Water Toxicity Model—Brain Volume by Magnetic Resonance Imaging (MRI): MRI is used to measure changes in brain volume in response to water shock, using the water toxicity model. As described for the survival and brain water content studies above, mice are injected, IP, with a water bolus alone or water bolus and test compound at 0.76 mg/kg, and changes in brain volume as detected by MRI are monitored. Mouse brain volumes are assessed using MRI scans collected with a 9.4T Bruker Biospec MRI scanner at the Case Center for Imaging Research at Case Western Reserve University. This imaging method is found to provide sufficient contrast and resolution to sensitively detect changes in total brain volume in the mouse water toxicity model for cerebral edema. High resolution T2-weighted sagittal scans (resolution=0.1 mm×0.1 mm×0.7 mm) of the mouse head are obtained prior to water injection, 5.67 min post water injection, and then every 5.2 minutes until the animal expires from the water loading. Each scan contains twenty-five 0.7 mm contiguous imaging slices of which 14-15 slices contain a portion of the brain. The cross sectional area of the brain in each imaging slice is measured by manual region-of-interest selection using ImageJ. Brain volumes are then calculated for each scan by summing the individual cross sectional brain areas and multiplying by the slice thickness (0.7 mm).

Figure 5:
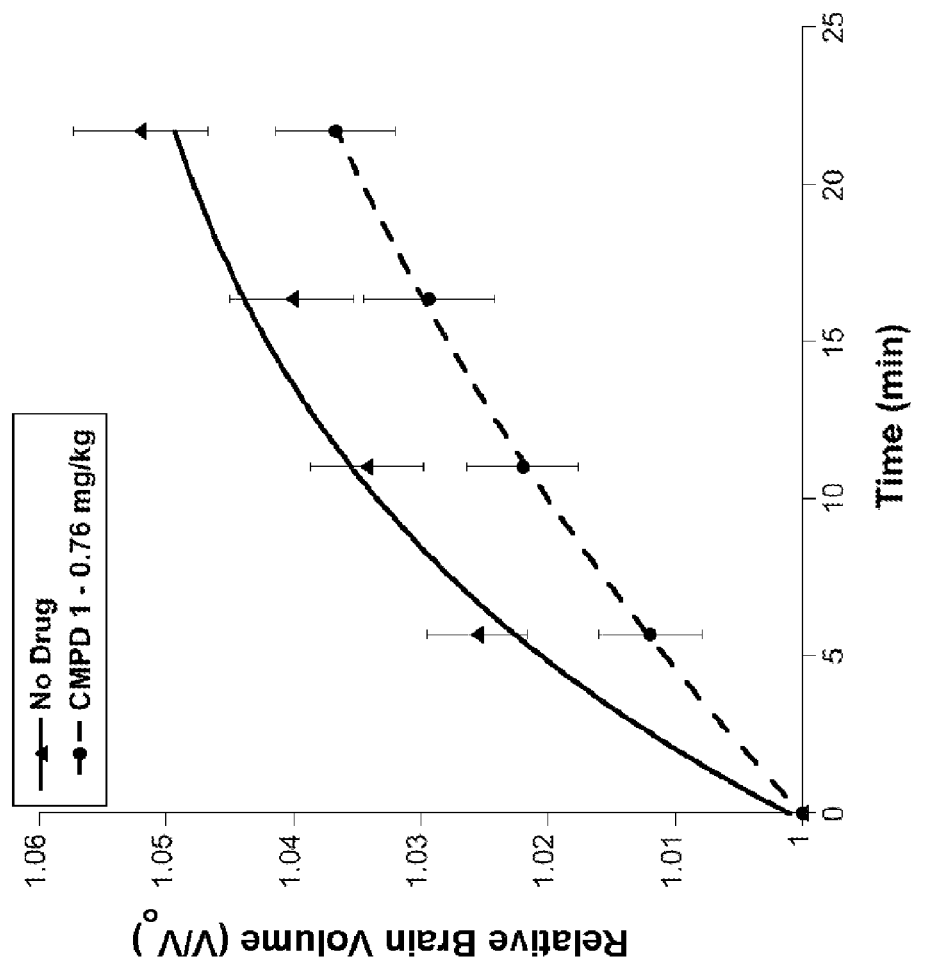
FIG. 5 depicts inhibition of cerebral edema formation by N-[3,5-bis(trifluoromethyl)phenyl]-5-chloro-2-hydroxybenzamide (Compound 1) in the mouse water toxicity model by MRI brain volume analysis, with n=14 mice/treatment. A time course of edema formation is shown comparing no drug vs. N-[3,5-bis(trifluoromethyl)phenyl]-5-chloro-2-hydroxybenzamide (Compound 1) at 0.76 mg/kg. The first time point at 5.67 min coincides with the scan slice at the middle of the brain during the first post-injection scan. Other time points are placed in a similar manner. The data is fitted to a single exponential equation.

Treatment with Compound 1 at 0.76 mg/kg reduces the rate of CE development from 0.081 to 0.032 min$^{-1}$ (or 2.5-fold) fit to a single exponential model (FIG. 5). Also, the extent of CE during the period of observation is reduced (FIG. 5). Moreover, plasma levels in the same assay are found to range between 0.03-0.06 µg as determined by LC-MS/MS (performed at Lerner Center, Cleveland Clinic, Cleveland, Ohio) and are sufficient to show efficacy in this model for CE.

The brain volume by magnetic resonance imaging experiment is also conducted with phenylbenzamide (0.39 mg/kg) and Compound 4 (0.83 mg/kg). Compound 4 reduces the rate of CE development from 0.081 to 0.022 min$^{-1}$ (Table 1). Phenylbenzamide fails to show reduction in the rate of CE in mice (Table 1).

TABLE 1

Efficacy of compounds on CE formation
in the mouse water toxicity model

| Compound | AQP Inhibition Cell-Based Assay (%) | Cerebral Edema Rate by MRI (min$^{-1}$) |
|---|---|---|
| No Drug | 0 | 0.081 |
| Compound 1 | 47.9 | 0.032 |
| Phenylbenzamide | 4.5 | 0.096 |
| Compound 4 | 38.9 | 0.022 |

For no drug and Compound 1, n=14 mice each. For phenylbenzamide and Compound 4, n=12 mice each.

Example 14—High Throughput Screening Assay

Under hypotonic shock, both untransfected cells and cells expressing an unrelated transmembrane protein (CD81, at levels equivalent to AQP4b) swell slowly but remain intact.

These observations are used to develop our high-throughput screening assay (HTS).

After hypotonic shock in a 384 well plate format, we return osmolality to normal (300 mOSM) by adding 2× concentrated phosphate buffered saline supplemented to 2 µM with a nonfluorescent acetoxymethyl derivative of calcein (calcein-AM) to each well. Intact cells take up calcein-AM and convert it to the fluorescent dye calcein giving a quantitative measure of the remaining intact cells. Burst cells do not convert the precursor to the dye. Water uptake by AQP4-expressing cells is relatively rapid, with most test cells bursting within 4 min of hypotonic shock, whereas most cells expressing CD81 remain viable after 8 min. Intracellular conversion of calcein-AM provides a strong and easily detectable signal at 535 nM in our assay (FIG. 6).

Calcein fluorescence end-point assay: Cells are seeded 24 hr before assay to reach 100% confluence. Culture medium is replaced with H$_2$O for 5:30 min (osmotic shock). Osmolality is then normalized with the addition of 2×PBS plus 2 µM calcein-AM. Cells are then incubated at 37° C. for an additional 30 min and fluorescence measured on a platereader. Rows 1-22 are seeded with CHO-AQP4 cells, and rows 23-24, with CHO-CD81 cells (384 well plate). Note, all plate edges are discarded. Relative Fluorescence Intensity is calculated as the fluorescence intensity (FI) of each well divided by the mean FI of AQP4 cells treated with DMSO (control). Criteria for a successful assay: coefficients of variation (CVs)<15%, and Z-factors >0.5. Statistical analysis shows that 5.5 min of osmotic shock provides the optimal signal-to-noise ratio.

TABLE 2

Statistics for endpoint 'calcein' assay
in FIG. 6; 5:30 min time point shown:

|  | Mean | StDev | CV | Z' | S/B |
|---|---|---|---|---|---|
| AQP4 | 581618 | 66311 | 11% | 0.629 | 5.0 |
| CD81 | 2910106 | 221240 | 8% | | |

As will be observed, the signal for the CD81 cells is ca. 5× higher than the signal for the APQ4 cells, because by 5.5 mins, most of the AQP4 cells have burst, while most of the CD81 cells remain intact. Inhibition of AQP4 would therefore be expected to provide a higher signal, more like the CD81 cells.

This assay is applied in a pilot screen of the MicroSource GenPlus 960 and the Maybridge Diversity™ 20 k libraries (approximately 21,000 compounds tested, each compound at 10-20 µM).

From this assay, a specific chemical series is identified, phenylbenzamides, which represents 3 out of the top 234 hits.

Hits from the HTS are validated using the same assay using a different plating arrangement. In FIG. 7, we show this validation assay used to examine Compound 3. Cells are seeded in a 96 well multiplate format with the plates edges omitted (lanes 1 and 24) and an entire column (n=16) is used to test the ability of a compound to block AQP4-mediated cell bursting upon H$_2$O shock. CHO cells expressing CD81 are seeded in lanes 2-3 as a control, and CHO cells expressing AQP4, in lanes 4-23. Cells are treated with 0.1% DMSO in 10% FBS, DMEM (even numbered columns) or 10 µM Compound 1 (odd number columns) in 0.1% DMSO, 10% FBS, DMEM for 30 minutes. The cells are shocked with H$_2$O for 5:30 minutes, then osmolality returned to 300 mOSM in the presence of 1 µM calcein-AM, as described above. The cells are incubated at 37° C. for 30 minutes and the relative fluorescence measured (ex 495/em 535 nM) on a fluorescence multiplate reader. The data in FIG. 7 represents the average relative fluoresence units (RFU±SEM, n=16).

Example 15—Water Toxicity Model for CE:
Intracranial Pressure (ICP)

ICP is monitored using a Samba 420 Sensor, pressure transducer, with a Samba 202 control unit (Harvard Apparatus, Holliston, Mass.). This ICP monitoring system consists of a 0.42 mm silicon sensor element mounted on an optical fiber. A 20-gauge syringe needle is implanted through the cisterna magna to a depth of ~1 cm. The needle then acts as a guide for insertion of the Samba Sensor and the site of implantation and the open end of the needle are sealed with 100% silicone sealant. A baseline ICP reading is established followed by a water bolus IP injection (20% weight of animal) with or without Compound 1. ICP is monitored until the animal expires from the water load.

Adjusting for the slight rise in ICP observed in the animals when they are monitored without the water bolus injection (FIG. 8, No Water Toxicity), Compound 1 at 0.76 mg/kg reduces the relative rate of ICP rise by 36%, from $3.6 \times 10^{-3}$ min$^{-1}$ to $2.3 \times 10^{-3}$ min$^{-1}$ (n=6 mice/treatment, mean±SEM).

Example 16—Conversion of 2-{[3,5-bis(trifluoromethyl)phenyl]carbamoyl}-4-chlorophenyl Phosphate Bis Ethanolamine Salt to Compound 1

Plasma or serum levels of Compound 1 are measured by LC-MS/MS at the Mass Spectrometry II Core facility at the Lerner Research Institute of the Cleveland Clinic Foundation. Measurements are taken at 15 minutes and 24 hours after a 10 mg/kg i.p. loading dose and 1 mg/ml at 8 µl/h maintenance dose (delivered by an Alzet i.p. osmotic pump, Durect Corp., Cupertino, Calif.) of 2-{[3,5-bis(trifluoromethyl)phenyl]carbamoyl}-4-chlorophenyl phosphate bis ethanolamine salt (n=5 mice/time point, mean±SEM) (FIG. 9). After initial processing to remove proteins (75% acetonitrile extraction), Compound 3 is introduced to improve quantitation using multiple reaction monitoring (MRM). Samples are analyzed by tandem LC-MS/MS using C18 reversed-phase chromatography and mass analysis with a triple-quadrapole mass spectrometer. The LC method is sufficient to separate Compound 1 from Compound 3 and subsequent MRM gave reliable quantitation with a linear response from 0.004-0.4 ng of Compound 1 for its most abundant daughter ion. The dashed line in FIG. 9 is the relative effective plasma concentration of Compound 1 observed in the mouse water toxicity model. Inclusion of an Alzet osmotic pump (Durect Corp., Cupertino, Calif.) containing 2-{[3,5-bis(trifluoromethyl)phenyl]carbamoyl}-4-chlorophenyl phosphate bis ethanolamine salt in the peritoneum is sufficient, in conjunction with an initial loading dose, to sustain Compound 1 above the expected efficacious plasma concentration of 20 ng/ml for 24 hours (FIG. 9).

The solubility of Compound 1 in water is 3.8 µg/ml. The solubility of Compound 5 in water is 1 mg/ml.

Initial experiments show rapid bioconversion of 2-{[3,5-bis(trifluoromethyl)phenyl]carbamoyl}-4-chlorophenyl phosphate bis ethanolamine to Compound 1 when added to mouse plasma in vitro. Less than 5 minutes at 20° C. is sufficient to render 2-{[3,5-bis(trifluoromethyl)phenyl]carbamoyl}-4-chlorophenyl phosphate bis ethanolamine undetectable. In addition, 2-{[3,5-bis(trifluoromethyl)phenyl]carbamoyl}-4-chlorophenyl phosphate bis ethanolamine salt is undetectable in plasma samples taken from mice injected IP with 2-{[3,5-bis(trifluoromethyl)phenyl]carbamoyl}-4-chlorophenyl phosphate mono ethanolamine. Instead, Compound 1 is detected at a concentration consistent with good bioavailability and near-complete conversion of 2-{([3,5-bis(trifluoromethyl)phenyl]carbamoyl}-4-chlorophenyl phosphate bis ethanolamine. With 2-{[3,5-bis(trifluoromethyl)phenyl]carbamoyl}-4-chlorophenyl phosphate bis ethanolamine, doses of 10 mg/kg and IP injection volumes in saline (0.5 ml for a 30 g mouse), that give serum concentrations of Compound 1 in excess of 400 ng/ml (FIG. 9) can be used. Key PK parameters for are: rate of absorption 0.12 min$^{-1}$; rate of elimination 0.017 min$^{-}$.

Example 17 Animal Stroke Model

Most ischemic strokes (~80%) occur in the region of the middle cerebral artery (MCA). To mimic this injury in mice, an intraluminal monofilament model of middle cerebral artery occlusion (MCAo) is used. Occlusion is achieved by inserting a surgical filament into the external carotid artery (ECA) and threading it forward into the internal carotid artery (ICA) until the tip blocks the origin of the MCA. The resulting cessation of blood flow gives rise to subsequent brain infarction in the MCA territory (Longa, E. Z. et al., *Reversible Middle Cerebral Artery Occlusion Without Craniectomy in Rats*, Stroke, 20, 84-91 (1989)). This technique is used to study a temporary occlusion in which the MCA is blocked for one hour. The filament is then removed allowing reperfusion to occur for 24 hours before the animals brain is imaged using T2-weighted scans in a 9.4T Bruker MRI scanner at the Case Center for Imaging Research (FIG. 10). FIG. 10 shows a single slice from a T2-weighted MR image depicting the center of the brain showing cerebral cortex, hippocampus, thalamus, amygdala and hypothalamus for a "Normal" mouse (left panels) and a mouse which receives MCAo for one hour followed by 24 hours of reperfusion (right panels). Dashed lines mark the midline of the brain and show a large shift in the MCAo brain due to cerebral edema. Solid line highlights the region of infarct in the MCAo brain.

Survival—Mice are treated with Compound 5 using a 2 mg/kg i.p. loading dose and 1 mg/ml at 8 µl/h maintenance dose (delivered by an i.p. osmotic pump) of Compound 5, or given saline (controls; n=17) using an identical approach. In this model, we observed a 29.4% improvement in overall survival at 24 h when animals are treated with Compound 5 ($X^2(1)$=4.26; P<0.05).

Cerebral Edema—Mice are given saline or treated with Compound 5 by multi-dosing at 5 mg/kg i.p. every three hours (n=8 per treatment). This dosing regimen is sufficient to maintain a plasma concentration of Compound 1>20 ng/ml for the duration of the study. Ipsilateral and contralateral hemispheric volume is measured from the T2-weighted MR images of mice 24 hours post-icus. Relative change in hemispheric volume is calculated as a percent of the difference between ipsilateral brain volume ($V_i$) and contralateral brain volume ($V_c$) relative to the contralateral brain volume (Percent Change in Hemispheric Brain Volume=$((V_i-V_c)/V_c)\times 100\%$.

Control animals show swelling in the ipsilateral hemisphere with a relative change in ipsilateral brain volume of 13.4%+1.9%, while animals given Compound 5 show a 4.2±1.7% change (P=0.003, ±SEM, see FIG. 11). This represents a 3.2-fold reduction in brain swelling after MCAo.

Neurological Outcome—In the same experiment as above, animals are scored for neurological outcome on a simple 5 point scale described in Manley, G. T. et al., *Aquaporin*-4 *Deletion in Mice Reduces Brain Edema After Acute Water Intoxication and Ischemic Stroke*, Nature Medicine, 6, 159-163 (2000). An improvement in neurological outcome is observed for animals given Compound 5. Control animals have an average neurological score of 2.77±0.66, while animals given Compound 5 have an average score of 0.88±0.31 (FIG. 12, inset, P=0.025, n=9 per treatment). Animals given Compound 5 did not progress into a state of severe paralysis or death.

The data from the MCAo stroke model together with the water toxicity (brain edema) model link the pharmacology of Compound 5/Compound 1 with improved outcomes in stroke.

The invention claimed is:

1. A process for synthesizing a compound of Formula IV

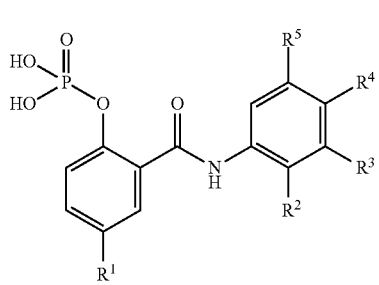

Formula IV wherein $R^1$, $R^2$, $R^3$, $R^4$, and $R^5$ are independently H, halogen, $C_{1-4}$-alkyl, $C_{1-4}$-haloalkyl, or cyano, wherein the process comprises reacting a compound of Formula VII and a compound of Formula VIII Formula VII

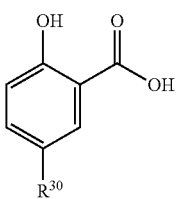

Formula VIII

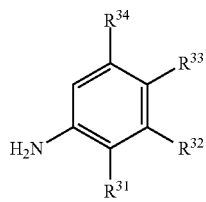

wherein $R^{30}$, $R^{31}$, $R^{32}$, $R^{33}$, and $R^{34}$ are independently H, halogen, $C_{1-4}$-alkyl, $C_{1-4}$-haloalkyl, or cyano to provide a compound of Formula V Formula V

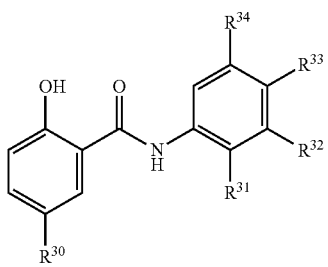

wherein $R^{30}$, $R^{31}$, $R^{32}$, $R^{33}$, and $R^{34}$ are independently H, halogen, $C_{1-4}$-alkyl, $C_{1-4}$-haloalkyl, or cyano, followed by reacting the compound of Formula V with a compound of Formula VI Formula VI

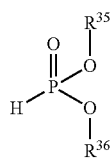

wherein $R^{35}$ and $R^{36}$ are independently —(CH$_2$CH$_2$)$_n$—Si(R$^{37}$)$_3$ and each $R^{37}$ is independently $C_{1-6}$-alkyl and n is 0 or 1 to provide a compound of Formula III Formula III

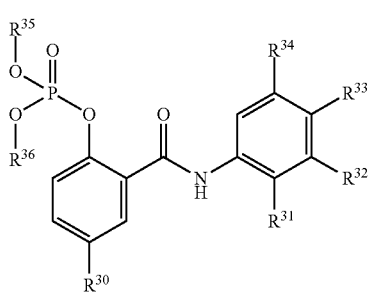

wherein $R^{30}$, $R^{31}$, $R^{32}$, $R^{33}$, and $R^{34}$ are independently H, halogen, $C_{1-4}$-alkyl, $C_{1-4}$-haloalkyl, or cyano, $R^{35}$ and $R^{36}$ are independently —(CH$_2$CH$_2$)$_n$—Si(R$^{37}$)$_3$, and each $R^{37}$ is independently $C_{1-6}$-alkyl and n is 0 or 1, followed by deprotecting the compound of Formula III to produce the compound of Formula IV.

2. The process of claim 1, wherein the process further comprises converting the compound of Formula VII to a compound of Formula IX Formula IX

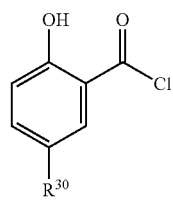

wherein $R^{30}$ is H, halogen, $C_{1-4}$-alkyl, $C_{1-4}$-haloalkyl, or cyano.

3. The process of claim 2, wherein the compound of Formula IX is formed by reaction with a compound comprising P or S.

4. The process of claim 3, wherein the compound of Formula IX is formed by reaction with PCl$_3$, PCl$_5$, or SOCl$_2$.

5. The process of claim 4, wherein the reaction occurs in a nonpolar solvent.

6. The process of claim 5, wherein the nonpolar solvent is toluene.

7. The process of claim 2, wherein $R^{30}$, $R^{32}$, and $R^{34}$ are independently halogen or $C_{1-4}$-haloalkyl and $R^{31}$ and $R^{33}$ are H.

8. The process of claim 2, wherein $R^{30}$, $R^{32}$, and $R^{34}$ are independently F, Cl, Br, or —CF$_3$ and $R^{31}$ and $R^{33}$ are H.

9. The process of claim 2, wherein $R^{30}$ is halogen, $R^{31}$ and $R^{33}$ are H, and $R^{32}$ and $R^{34}$ are independently $C_{1-4}$-haloalkyl.

10. The process of claim 9, wherein $R^{30}$ is Cl and $R^{32}$ and $R^{34}$ are —CF$_3$.

11. The process of claim 2, wherein each $R^{37}$ is independently $C_{1-4}$-alkyl.

12. The process of claim 2, wherein $R^{35}$ and $R^{36}$ are the same.

13. The process of claim 2, wherein n is 1.

14. The process of claim 10, wherein $R^{35}$ and $R^{36}$ are —CH$_2$—CH$_2$—Si(CH$_3$)$_3$.

15. The process of claim 14, wherein the compound of Formula V is

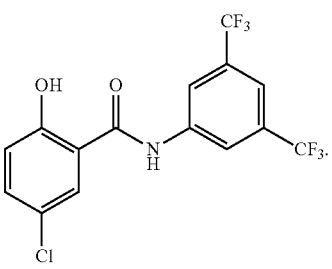 [SMILES: O=C(Nc1cc(C(F)(F)F)cc(C(F)(F)F)c1)c1cc(Cl)ccc1O]

16. The process of claim 15, wherein the compound of Formula VI is

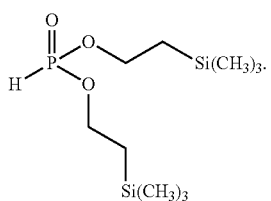
17. The process of claim 16, wherein the compound of Formula III is
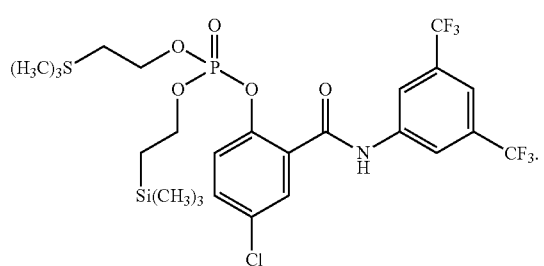
18. The process of claim 17, wherein the compound of Formula III is deprotected with a deprotecting agent comprising F.
19. The process of claim 18, wherein the deprotecting agent is $CF_3COOH$.
20. The process of claim 19, wherein the compound of Formula IV is
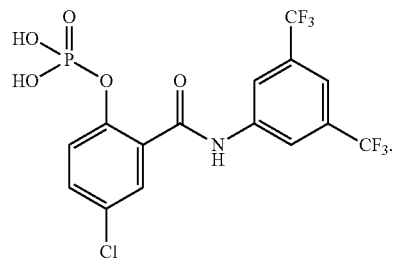 [SMILES: O=C(Nc1cc(C(F)(F)F)cc(C(F)(F)F)c1)c1cc(Cl)ccc1OP(=O)(O)O]
* * * * *